US011542305B2

(12) United States Patent
Gao et al.

(10) Patent No.: US 11,542,305 B2
(45) Date of Patent: Jan. 3, 2023

(54) SYNTHETIC PROTEIN CIRCUITS DETECTING SIGNAL TRANSDUCER ACTIVITY

(71) Applicant: California Institute of Technology, Pasadena, CA (US)

(72) Inventors: Xiaojing Gao, Los Angeles, CA (US); Michael B. Elowitz, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 377 days.

(21) Appl. No.: 16/556,063

(22) Filed: Aug. 29, 2019

(65) Prior Publication Data

US 2020/0071362 A1    Mar. 5, 2020

Related U.S. Application Data

(60) Provisional application No. 62/725,959, filed on Aug. 31, 2018.

(51) Int. Cl.
| | |
|---|---|
| *C12N 15/62* | (2006.01) |
| *C07K 19/00* | (2006.01) |
| *C07K 14/00* | (2006.01) |
| *G01N 33/68* | (2006.01) |
| *C12N 9/50* | (2006.01) |
| *C07K 14/47* | (2006.01) |
| *A61K 38/00* | (2006.01) |

(52) U.S. Cl.
CPC ............ *C07K 14/001* (2013.01); *C07K 14/47* (2013.01); *C12N 9/506* (2013.01); *C12Y 304/22044* (2013.01); *G01N 33/6803* (2013.01); *A61K 38/00* (2013.01); *C07K 2319/02* (2013.01); *C07K 2319/50* (2013.01)

(58) Field of Classification Search
CPC ............... C07K 19/00; C07K 2319/00; G01N 33/6845; G01N 2500/10; C12N 15/62; C12Q 1/37
See application file for complete search history.

(56) References Cited

U.S. PATENT DOCUMENTS

| | | | |
|---|---|---|---|
| 5,739,002 | A | 4/1998 | De Francesco et al. |
| 6,005,079 | A | 12/1999 | Casterman et al. |
| 6,348,584 | B1 | 2/2002 | Hodgson et al. |
| 6,673,901 | B2 | 1/2004 | Koide |
| 6,856,914 | B1 | 2/2005 | Pelech |
| 6,884,870 | B2 | 4/2005 | Hav et al. |
| 8,394,604 | B2 | 3/2013 | Liu et al. |
| 10,899,823 | B2 * | 1/2021 | Gao ............. C07K 14/81 |
| 2002/0132327 | A1 | 9/2002 | Hay et al. |
| 2005/0271647 | A1 | 12/2005 | Baltimore et al. |
| 2008/0227750 | A1 | 9/2008 | Dennis et al. |
| 2009/0162341 | A1 | 6/2009 | Foster et al. |
| 2013/0230863 | A1 | 9/2013 | Tang et al. |
| 2015/0315570 | A1 | 11/2015 | Zhao et al. |
| 2016/0223529 | A1 | 8/2016 | Stein et al. |
| 2017/0315114 | A1 | 11/2017 | Stein et al. |
| 2018/0118818 | A1 | 5/2018 | Tang et al. |
| 2019/0248873 | A1 | 8/2019 | Gao et al. |

FOREIGN PATENT DOCUMENTS

| | | | |
|---|---|---|---|
| WO | WO1994004678 | 3/1994 | |
| WO | WO1994025591 | 11/1994 | |
| WO | WO2014040129 | 3/2014 | |
| WO | WO-2014040129 A1 * | 3/2014 | ......... C07K 16/3069 |
| WO | WO2015017214 | 2/2015 | |
| WO | WO2015164594 | 10/2015 | |
| WO | WO2018069782 | 4/2018 | |
| WO | WO2019147478 | 8/2019 | |

OTHER PUBLICATIONS

Adams et al., "Overview and analysis of the polyprotein cleavage sites in the family Potyviridae," Molecular Plant Pathology 2005, 6(4), 471-487.
Angelici et al., "Synthetic Biology Platform for Sensing and Integrating Endogenous Transcriptional Inputs in Mammalian Cells," Cell Reports 2016, 16, 2525-2537.
Aronheim et al., "Membrane Targeting of the Nucleotide Exchange Factor Sos Is Sufficient for Activating the Ras Signaling Pathway," Cell 1994, 78 ,949-961.
Auslander et al., "Programmable single-cell mammalian biocomputers," Nature 2012, 487, 123-127.
Banaszynski et al., "A Rapid, Reversible, and Tunable Method to Regulate Protein Function in Living Cells Using Synthetic Small Molecules," Cell 2006, 126, 995-1004.
Barnea et al., "The genetic design of signaling cascades to record receptor activation," PNAS 2008, 105(1), 64-69.
Barrett et al., "Chimeric Antigen Receptor Therapy for Cancer," Annual Review of Medicine 2014, 65, 333-347.
Bartenschlager et al., "The NS3/4A proteinase of the hepatitis C virus: unravelling structure and function of an unusual enzyme and a prime target for antiviral therapy," Journal of Viral Hepatitis 1999, 6, 165-181.
Basu et al., "A synthetic multicellular system for programmed pattern formation," Nature 2005, 434, 1130-1134.
Basu et al., "Spatiotemporal control of gene expression with pulse-generating networks," PNAS 2004, 101(17), 6355-6360.
Bintu et al., "Dynamics of epigenetic regulation at the single-cell level," Science 2016, 351(6274), 720-724.

(Continued)

*Primary Examiner* — Karen Cochrane Carlson
(74) *Attorney, Agent, or Firm* — Sheppard, Mullin, Richter & Hampton LLP

(57) ABSTRACT

Disclosed herein include methods, compositions, and kits suitable for use in detecting the activation level of a signal transducer. In some embodiments, there are provided synthetic protein circuits wherein recruitment of synthetic protein circuit components to an association location upon activation of a signal transducer generates an active effector protein. The effector protein can be configured to carry out a variety of functions when in an active state, such as, for example, inducing cell death. Methods of treating a disease or disorder characterized by aberrant signaling are provided in some embodiments.

22 Claims, 22 Drawing Sheets

(56) References Cited

OTHER PUBLICATIONS

Boerger et al., "Retroviral vectors preloaded with a viral receptor-ligand bridge protein are targeted to specific cell types," PNAS 1999, 96, 9867-9872.
Bonnet et al., "Amplifying Genetic Logic Gates," Science 2013, 340, 599-602.
Budihardjo et al., "Biochemical Pathways of Caspase Activation During Apoptosis," Annual Review of Cellular Development and Biology 1999, 15, 269-290.
Butko et al., "Fluorescent and photo-oxidizing TimeSTAMP tags track protein fates in light and electron microscopy," Nature Neuroscience 2012, 15(12), 1742-1751.
Camacho-Soto et al., "Small Molecule Gated Split-Tyrosine Phosphatases and Orthogonal Split-Tyrosine Kinases," Journal of the American Chemical Society 2014, 136, 17078-17086.
Camacho-Soto et al., "Ligand-Gated Split-Kinases," Journal of the American Chemical Society 2014, 136, 3995-4002.
Carrington et al., "A viral cleavage site cassette: Identification of amino acid sequences required for tobacco etch virus polyprotein processing," PNAS 1988, 85, 3391-3395.
Chen et al., "Predicting PDZ domain-peptide interactions from primary sequences," Nature Biotechnology 2008, 26(9), 1041-1045.
Choi et al., "Selective viral vector transduction of ErbB4 expressing cortical interneurons in vivo with a viral receptor-ligand bridge protein," PNAS 2010, 107(38), 16703-16708.
Chung et al., "Tunable and reversible drug control of protein production via a self-excising degron," Nature Chemical Biology 2015, 11, 713-720.
Cox et al., "Drugging the undruggable Ras: mission possible?," Nature Reviews Drug Discovery 2014, 13(11), 828-851.
Dagliyan et al., "Computational design of chemogenetic and optogenetic split proteins," Nature Communications, 9(4042), 1-8.
Daringer et al., "Modular Extracellular Sensor Architecture for Engineering Mammalian Cell-based Devices," ACS Synthetic Biology 2014, 3, 892-902.
De Felipe, "Skipping the co-expression problem: the new 2A "CHYSEL" technology," Genetic Vaccines and Therapy 2004, 2(13).
De Felipe et al., "Targeting of Proteins Derived from Self-Processing Polyproteins Containing Multiple Signal Sequences," Traffic 2004, 5, 616-626.
Downward, "Targeting RAS Signaling Pathways in Cancer Therapy," Nature Publishing Group 2003, 3, 11-22.
Dueber et al., "Reprogramming Control of an Allosteric Signaling Switch Through Modular Recombination," Science 2003, 301, 1904-1908.
Elowitz et al., "A synthetic oscillatory network of transcriptional regulators," Nature 2000, 403, 335-338.
Fernandez-Rodriguez et al., "Post-translational control of genetic circuits using Potyvirus proteases," Nucleic Acids Research 2016, 44(13), 6493-6502.
Ferrell et al., "Ultrasensitivity Part II: Multisite phosphorylation, stoichiometric inhibitors, and positive feedback," Trends in Biochemical Sciences 2014, 39(11), 556-569.
Fink et al., "Design of fast proteolysis-based signaling and logic circuits in mammalian cells," Nature Chemical Biology 2018, 15, 115-122.
Gao et al., "Programmable protein circuits in living cells," Science 2018, 361, 1252-1258.
Gardner et al., "Construction of a genetic toggle switch in *Escherichia coli*," Nature, 403, 339-342.
Ghabrial et al., "Molecular genetic analyses of the soybean mosaic virus Nla proteinase," Journal of General Virology 1990, 71, 1921-1927.
Ghosh et al., "Antiparallel Leucine Zipper-Directed Protein Reassembly: Application to the Green Fluorescent Protein," Journal of the American Chemical Society 2000, 122, 5658-5659.

Gramespacher et al., "Intein Zymogens: Conditional Assembly and Splicing of Split Inteins via Targeted Proteolysis," Journal of the American Chemical Society 2017, 139, 8074-8077.
Gray et al., "Activation of Specific Apoptotic Caspases with an Engineered Small Molecule-Activated Protease," Cell 2010, 142(4), 637-646.
Greber et al., "An engineered mammalian band-pass network," Nucleic Acids Research 2010, 38(18), e174.
Hancock et al., "A CAAX or a CAAL motif and a second signal are sufficient for plasma membrane targeting of ras proteins," The EMBO Journal 1991, 10(13), 4033-4039.
Hart et al., "The Utility of Paradoxical Components in Biological Circuits," Molecular Cell 2013, 49, 213-221.
Herrmann et al., "Quantitative Analysis of the Complex between p21ras and the Ras-binding Domain of the Human Raf-1 Protein Kinase," Journal of Biological Chemistry 1995, 270(7), 2901-2905.
Howard et al., "Redirecting tyrosine kinase signaling to an apoptotic caspase pathway through chimeric adaptor proteins," PNAS 2003, 100(20), 11267-11272.
International Search Report and Written Opinion dated Aug. 12, 2019 in PCT Patent Application PCT/US2019/014078.
International Search Report and Written Opinion dated Dec. 19, 2019 in PCT Patent Application PCT/US2019/048914.
Iwamoto et al., "A General Chemical Method to Regulate Protein Stability in the Mammalian Central Nervous System," Chemistry & Biology 2010, 17, 981-988.
Jacobs et al., "StaPLs: versatile genetically encoded modules for engineering drug-inducible proteins," Nature Methods 2018, 15(7), 523-526.
Khalil et al., "A Synthetic Biology Framework for Programming Eukaryotic Transcription Functions," Cell 2012, 150, 647-658.
Kim et al., "Time-gated detection of protein-protein interactions with transcriptional readout," eLife 2017, 6, e30233.
Kipniss et al., "Engineering cell sensing and responses using a GPCR-coupled CRISPR-Cas system," Nature Communications 2017, 8, 2212.
Koch-Nolte et al., "Single domain antibodies from llama effectively and specifically block T cell ecto-ADP-ribosyltransferase ART2.2 in vivo," The FASEB Journal 2007, 21, 3490-3498.
Koh et al., "An Internal Ribosome Entry Site (IRES) Mutant Library for Tuning Expression Level of Multiple Genes in Mammalian Cells," PLOS One 2013, 8(12), e82100.
Kojima et al., "Toward a world of theranostic medication: Programming biological sentinel systems for therapeutic intervention," Advanced Drug Delivery Reviews 2016, 105, 66-76.
Lichty et al., "Vesicular stomatitis virus: re-inventing the bullet," TRENDS in Molecular Medicine 2004, 10(5), 210-216.
Lienert et al., "Synthetic biology in mammalian cells: Next generation research tools and therapeutics," Nature Reviews of Molecular Cell Biology 2014, 15(2), 95-107.
Lohmueller et al., "A tunable zinc finger-based framework for Boolean logic computation in mammalian cells," Nucleic Acids Research 2012, 40(11), 5180-5187.
Ma et al., "Defining Network Topologies that Can Achieve Biochemical Adaptation," Cell 2009, 138, 760-773.
Marchisio et al., "Computational design of synthetic gene circuits with composable parts," Bioinformatics 2008, 24(17), 1903-1910.
Morsut et al., "Engineering Customized Cell Sensing and Response Behaviors Using Synthetic Notch Receptors," Cell 2016, 164(4), 780-791.
Nakanishi et al., Development of Sendai Virus Vectors and their Potential Applications in Gene Therapy and Regenerative Medicine, Current Gene Therapy 2012, 12, 410-416.
Nallamsetty et al., "Efficient site-specific processing of fusion proteins by tobacco vein mottling virus protease in vivo and in vitro," Protein Expression and Purification 2004, 38, 108-115.
Nelson, "Antibody fragments," mAbs 2010, 2(1), 77-83.
Nielsen et al., "Genetic circuit design automation," Science 2016, 352(6281), aac7341.
Nissim et al., "A tunable dual-promoter integrator for targeting of cancer cells," Molecular Systems Biology 2010, 6(444), 1-9.
Oliveira et al., "An Improved Ras Sensor for Highly Sensitive and Quantitative FRET-FLIM Imaging," PLOS One 2013, 8(1), e52874.

(56) References Cited

OTHER PUBLICATIONS

Park et al., "Rewiring MAP Kinase Pathways Using Alternative Scaffold Assembly Mechanisms," Science 2003, 299, 1061-1064.
Porcher et al., "The Bicoid Morphogen System," Current Biology 2010, 20(5), R249-R254.
Pu et al., "Evolution of a split RNA polymerase as a versatile biosensor platform," Nature Chemical Biology 2017, 13(4), 432-438.
Reinke et al., "A synthetic coiled-coil interactome provides heterospecific modules for molecular engineering," Journal of the American Chemical Society 2010, 132(17), 6025-6031.
Restriction Requirement dated Dec. 9, 2019 in U.S. Appl. No. 16/250,314.
Riechmann et al., "Single domain antibodies: comparison of camel VH and camelised human VH domains," Journal of Immunological Methods 1999, 231, 25-38.
Rinaudo et al., "A universal RNAi-based logic evaluator that operates in mammalian cells," Nature Biotechnology 2007, 1-6.
Roquet et al., "Synthetic recombinase-based state machines in living cells," Science 2016, 353(6297), aad8559.
Rossi et al., "Monitoring protein-protein interactions in intact eukaryotic cells by b-galactosidase complementation," PNAS 1997, 94, 8405-8410.
Roybal et al., "Precision Tumor Recognition by T Cells With Combinatorial Antigen-Sensing Circuits," Cell 2016, 164, 770-779.
Russell et al., "Oncolytic Virotherapy," Nature Biotechnology 2012, 30(7).
Schnell et al., "Infectious rabies viruses from cloned cDNA," The EMBO Journal 1994, 13(18), 4195-4203.
Schwanhausser et al. "Global quantification of mammalian gene expression control" Nature 2011, 473, 337-342.
Snitkovsky et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," Journal of Virology 2000, 74(20), 9540-9545.
Stein et al., "Ultrasensitive Scaffold-Dependent Protease Sensors with Large Dynamic Range," ACS Synthetic Biology 2017, 6, 1337-1342.
Stein et al., "Protease-based synthetic sensing and signal amplification," PNAS 2014, 1-6.
Stevens et al., "Design of a Split Intein with Exceptional Protein Splicing Activity," Journal of the American Chemical Society 2016, 138, 2162-2165.
Stricker et al. "A fast, robust and tunable synthetic gene oscillator," Nature 2008, 456, 516-520.
Szymczak et al., "Correction of multi-gene deficiency in vivo using a single 'self-cleaving' 2A peptide-based retroviral vector," Nature Biotechnology 2004, 22, 589-594.
Tang et al., "Detection and manipulation of live antigen-expressing cells using conditionally stable nanobodies," eLIFE 2016, 5, e15312.
Taremi et al., "Construction, expression, and characterization of a novel fully activated recombinant single-chain hepatitis C virus protease," Protein Science 1998, 7, 2143-2149.
Taxis et al., "Efficient protein depletion by genetically controlled deprotection of a dormant N-degron," Molecular Systems Biology 2009, 5(267), 1-7.
To et al., "Rationally designed fluorogenic protease reporter visualizes spatiotemporal dynamics of apoptosis in vivo," PNAS 2015, 112(11), 3338-3343.
Tozser et al., "Comparison of the substrate specificity of two potyvirus proteases," The FEBS Journal 2005, 272, 514-523.
Truong et al., "Development of an intein-mediated split-Cas9 system for gene therapy," Nucleic Acids Research 2015, 43(13), 6450-6458.
Varshavsky, "The N-end rule: Functions, mysteries, uses," PNAS 1996, 93, 12142-12149.
Waugh, "An overview of enzymatic reagents for the removal of affinity tags," Protein Expression and Purification 2011.
Wehr et al., "Monitoring regulated protein-protein interactions using split TEV," Nature Methods 2006, 3(12), 985-993.
Weinberg et al., "Large-scale design of robust genetic circuits with multiple inputs and outputs for mammalian cells," Nature Biotechnology 2017, 35(5), 453-462.
Weinheimer et al., "Autoproteolysis of Herpes Simplex Virus Type 1 Protease Releases an Active Catalytic Domain Found in Intermediate Capsid Particles," Journal of Virology 1993, 67(10), 5813-5822.
Wikstrand et al., "The class III variant of the epidermal growth factor receptor (EGFRvIII): characterization and utilization as an immunotherapeutic target," Journal of NeuroVirology 1998, 4, 148-158.
Wroblewska et al., "Mammalian synthetic circuits with RNA binding proteins delivered by RNA," Nature Biotechnology 2015, 33(8), 839-841.
Xie et al., "Multi-Input RNAi-Based Logic Circuit for Identification of Specific Cancer Cells," Science 2011, 333, 1307-1311.
Yasuda et al., "Supersensitive Ras activation in dendrites and spines revealed by two-photon fluorescence lifetime imaging," Nature Neuroscience 2006, 9(2), 283-291.
Yeh et al., "Rewiring cellular morphology pathways with synthetic guanine nucleotide exchange factors," Nature 2007, 447, 596-600.
Zetche et al., "A Split Cas9 Architecture for Inducible Genome Editing and Transcription Modulation," Nature Biotechnology 2015, 33(2), 139-142.
Dissing et al., "Autoproteolysis and feedback in a protease cascade directing *Drosophila* dorsal-ventral cell fate," The EMBO Journal 2001, 20(10), 2387-2393.
Griesbeck et al., "Reducing the Environmental Sensitivity of Yellow Fluorescent Protein," The Journal of Biological Chemistry 2001, 276(31), 29188-29194. doi:10.1074/jbc.M102815200.
International Search Report and Written Opinion dated May 7, 2020 in PCT Patent Application PCT/US2020/012928.
Lonzaric et al., "Design and applications of synthetic information processing circuits in mammalian cells," Synthetic Biology 2018, 2, 1-34.
Partial European Search Report dated Nov. 19, 2021 in European Patent Application 19743690.0.
Restriction Requirement dated Dec. 7, 2021 in U.S. Appl. No. 16/738,664.
Stein et al., "Synthetic protein switches: design principles and applications," Trends in Biotechnology 2015, 33(2), 101-110.
Extended European Search Report dated Jun. 15, 2022 in European Patent Application No. 19854896.8.
Shekhawat et al., "An Autoinhibited Coiled-Coil Design Strategy for Split-Protein Protease Sensors," J. Am. Chem Soc. 2009, 131, 15284-15290.

* cited by examiner

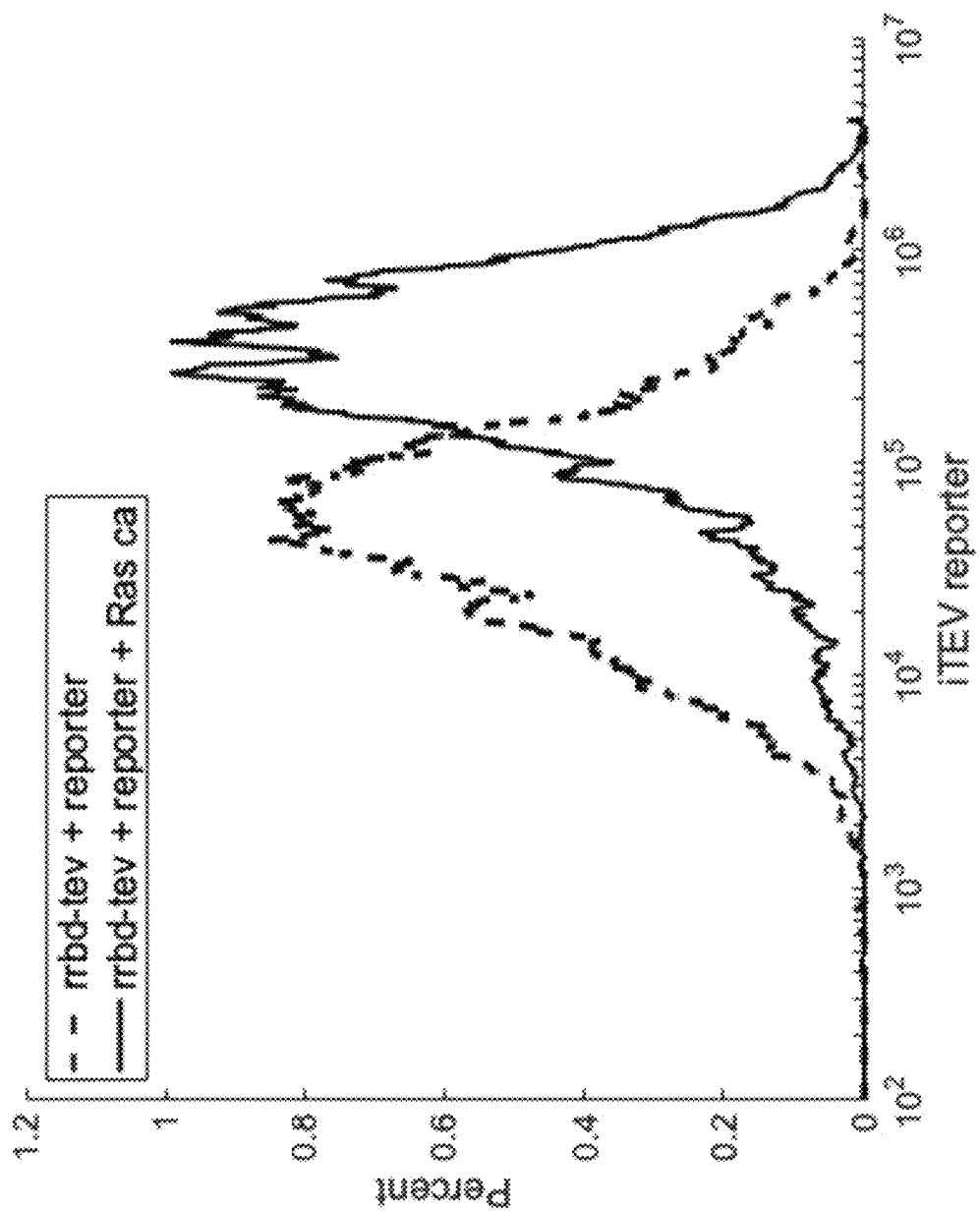

US 11,542,305 B2

SYNTHETIC PROTEIN CIRCUITS DETECTING SIGNAL TRANSDUCER ACTIVITY

RELATED APPLICATIONS

This application claims the benefit under 35 U.S.C. § 119(e) of U.S. Provisional Patent Application Ser. No. 62/725,959, filed Aug. 31, 2018, the content of this related application is incorporated herein by reference in its entirety for all purposes.

STATEMENT REGARDING FEDERALLY SPONSORED R&D

This invention was made with government support under Grant No. GM007616 awarded by the National Institutes of Health and under Grant No. HR0011-17-2-0008 awarded by DARPA. The government has certain rights in the invention.

BACKGROUND

Field

The present disclosure relates generally to the field of synthetic biology.

Description of the Related Art

Synthetic biology may enable design of new functions in living cells. Many natural cellular functions are implemented by protein-level circuits, in which proteins specifically modify each other's activity, localization, or stability. Synthetic protein circuits could provide advantages over gene regulation circuits in enabling the design of new functions in living cells. There is a need for synthetic protein circuits that can be configured to directly sense the activation level of signal transducers.

SUMMARY

Disclosed herein include synthetic protein circuits. In some embodiments, the synthetic protein circuit comprises: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting. In some embodiments, the first signal transducer binding domain of the first polypeptide and the second signal transducer binding domain of the second polypeptide are identical. In some embodiments, the first transducer and the second transducer are identical.

In some embodiments, the first signal transducer, the second signal transducer, or both, are capable of being localized at the association location. In some embodiments, the first signal transducer when in a first signal transducer active state, the second signal transducer when in a second signal transducer active state, or both, are capable of being localized at the association location. In some embodiments, the first signal transducer when in a first inactive state, the second signal transducer when in a second inactive state, or both, are capable of being localized at the association location. In some embodiments, the first signal transducer binding domain of the first polypeptide is capable of binding to the first signal transducer, wherein the second signal transducer binding domain of the second polypeptide is capable of binding to the second signal transducer, or both. In some embodiments, the first signal transducer binding domain of the first polypeptide is capable of binding to the first signal transducer in a first signal transducer active state, wherein the second signal transducer binding domain of the second polypeptide is capable of binding to the second signal transducer in a second signal transducer active state, or both. In some embodiments, the first signal transducer binding domain of the first polypeptide is capable of binding to the first signal transducer in a first inactive state, wherein the second signal transducer binding domain of the second polypeptide is capable of binding to the second signal transducer in a second inactive state, or both. In some embodiments, the signal transducer binding domain of the first polypeptide is capable of binding the first signal transducer to form the first signal transducer-bound polypeptide at the association location, wherein the signal transducer binding domain of the first polypeptide is capable of binding the first signal transducer to form the first signal transducer-bound polypeptide at the association location, or both. In some embodiments, the signal transducer binding domain of the first polypeptide is capable of binding the first signal transducer to form the first signal transducer-bound polypeptide at a first cellular location other than the association location, wherein the signal transducer binding domain of the first polypeptide is capable of binding the first signal transducer to form the first signal transducer-bound polypeptide at a second cellular location other than the association location, or both. In some embodiments, the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof. In some embodiments, the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

In some embodiments, a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state. In some embodiments, a first concentration of the first protease in the first protease active state is at least two-fold higher at the association location as compared a cellular location other than the association location when the first signal transducer is in a first signal transducer active state and/or when the second signal transducer is in a second signal transducer active state. In some embodiments, the first part of the first protease domain and the second part of the first protease domain have the weak association affinity when the first signal transducer is in a first signal transducer inactive state and/or the second signal transducer inactive state. In some embodiments, the first part of the first protease domain and the second part of the first protease domain are incapable of associating to form the first protease in the first protease active state when the first signal transducer is in a first signal transducer inactive state and/or the second signal transducer is in a second signal transducer inactive state. In some embodiments, a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state. In some embodiments, a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state. In some embodiments, the first part of the first protease domain and the second part of the first protease domain are capable of associating with each other to form the first protease in the first protease active state at a threshold first polypeptide concentration and a threshold second polypeptide concentration at the association location. In some embodiments, the threshold first polypeptide concentration and the threshold second polypeptide concentration at the association location are reached at a threshold signal transducer activation level of the signal transducer.

In some embodiments, the effector protein changes from an effector inactive state to an effector active state when the first protease in the first protease active state cuts the first cut site of the effector. In some embodiments, a level of activation of the effector protein positively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein changes from an effector active state to an effector inactive state when the first protease in the first protease active state cuts the first cut site of the effector. In some embodiments, a level of activation of the effector protein negatively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein comprises a third signal transducer binding domain, and wherein the third signal transducer binding domain is capable of binding the first signal transducer and/or the second signal transducer.

In some embodiments, the synthetic protein circuit comprises a repressor protein, wherein the repressor protein comprises a second protease. In some embodiments, the second protease in a second protease active state is capable of cutting a first cut site of the first polypeptide and/or a second cut site of the second polypeptide. In some embodiments, the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide. In some embodiments, the repressor protein comprises a cut site the first protease in the first protease active state is capable of cutting. In some embodiments, the repressor protein is changed into a repressor destabilized state, a repressor delocalized state, and/or a repressor inactivate state after the first protease cuts the cut site of the repressor protein. In some embodiments, the effector protein comprises a second cut site the second protease in the second protease active state is capable of cutting. In some embodiments, the effector protein is changed into a first effector destabilized state, a first effector delocalized state, and/or a first effector inactivate state after the second protease in the second protease active state cuts the cut site of the effector protein. In some embodiments, the effector protein comprises a degron, wherein the second protease in the second protease active state is capable of cutting the second cut site of the effector protein to expose the degron, and wherein the degron of the effector protein being exposed changes the effector protein to an effector destabilized state. In some embodiments, the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide. In some embodiments, the repressor protein comprises a cut site the first protease in the first protease active state is capable of cutting. In some embodiments, the repressor protein is changed into a repressor stabilized state, a repressor localized state, and/or a repressor activate state after the first protease in the first protease active state cuts the first cut site of the repressor protein. In some embodiments, the effector protein comprises a second cut site the second protease in the second protease active state is capable of cutting. In some embodiments, the effector protein is changed into a first effector stabilized state, a first effector localized state, and/or a first effector activate state after the second protease in the second protease active state cuts the second cut site of the effector protein. In some embodiments, the effector protein comprises a degron, wherein the second protease in the second protease active state is capable of cutting the second cut site of the effector protein to hide the degron, and wherein the degron of the effector protein being hidden changes the effector protein to an effector stabilized state. In some embodiments, the effector protein is capable of changing a synthetic protein circuit component of the synthetic protein circuit to a synthetic protein circuit component active state. In some embodiments, the effector protein comprises a third protease domain, and wherein the third protease domain is changes to an effector inactive state after the second protease in the second protease active state cuts the cute site of the effector protein. In some embodiments, the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector. In some embodiments, the effector protein in an effector active state is capable of activating an endogenous signal transduction pathway. In some embodiments, the effector protein in an effector active state is capable of inactivating an endogenous signal transduction pathway. In some embodiments, the effector protein comprises Caspase-3, Caspase 7, Caspase-9, Caspase-8, Bax, Bid, Bad, Bak, BCL2L11, p53, PUMA, Diablo/SMAC, S-TRAIL, or any combination thereof. In some embodiments, the effector protein in an effector active state is capable of rendering a resident cell sensitive to a prodrug. In some embodiments, the effector protein comprises cytosine deaminase and uracil phosphoribosyl transferase, and wherein the prodrug is 5-fluorocytosine (5-FC). In some embodiments, the effector protein comprises thymidine kinase (TK), and the wherein the prodrug comprises ganciclovir.

In some embodiments, two or more of the first signal transducer binding domain, the second signal transducer binding domain, and/or third signal transducer binding domain are identical. In some embodiments, two or more of the first signal transducer binding domain, the second signal transducer binding domain, and/or third signal transducer binding domain are different. In some embodiments, the first signal transducer binding domain, the second signal transducer binding domain, and/or third signal transducer binding domain each is capable of binding molecules of the first signal transducer and/or the second signal transducer. In some embodiments, the third signal transducer binding domain is capable of binding to a third signal transducer at the association location. In some embodiments, the first signal transducer, the second signal transducer, and/or the third signal transducer belong to a signal transduction pathway. In some embodiments, the first signal transducer binding domain, the second signal transducer binding domain, and/or the third signal transducer binding domain comprise a RAS binding domain (RBD) and/or RAS association domain (RAD). In some embodiments, the first signal transducer binding domain, the second signal transducer binding domain, and/or the third signal transducer binding domain comprises a lipid binding domain. In some embodiments, the lipid binding domain comprises a Pleckstrin homology (PH) domain. In some embodiments, the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

In some embodiments, the first signal transducer is capable of binding the first signal transducer binding domain and/or the second signal transducer is capable of binding the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof. In some embodiments, the first signal transducer, the second signal transducer, or both are endogenous proteins. In some embodiments, the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof. In some embodiments, the first signal transducer and/or the second signal transducer are capable of regulating cell survival, cell growth, cell proliferation, cell adhesion, cell migration, cell metabolism, cell morphology, cell differentiation, apoptosis, or any combination thereof. In some embodiments, the first signal transducer, the second signal transducer, or both comprise a RAS protein. In some embodiments, the RAS protein is KRAS, NRHAS, HRAS, or any combination thereof. In some embodiments, the first signal transducer, the second signal transducer, or both are exogenous proteins. In some embodiments, the synthetic protein circuit comprises the first signal transducer, the second signal transducer, or both. In some embodiments, the first signal transducer, the second signal transducer, or both comprise a lipid. In some embodiments, the lipid comprises a phospholipid. In some embodiments, the phospholipid is phosphatidylinositol 3-phosphate.

In some embodiments, the synthetic protein circuit is capable of detecting an activity of the first signal transducer and an activity of the second signal transducer. In some embodiments, an activity of the effector protein correlates with an activity of the first signal transducer and/or an activity of the second signal transducer. In some embodiments, the synthetic protein circuit is capable of detecting activities of the first signal transducer and activities of the second signal transducer over a period of time. In some embodiments, activities of the effector protein correlate with activities of the first signal transducer and activities of the second signal transducer over a period of time. In some embodiments, the synthetic protein circuit is capable of detecting an aberrant signaling. In some embodiments, aberrant signaling involves an active signal transducer. In some embodiments, the aberrant signaling involves an overactive signal transducer. In some embodiments, the aberrant signaling involves a constitutively active signal transducer over a period of time. In some embodiments, the synthetic protein circuit is capable of detecting an activity of a signal transducer activator and/or an activity of a signal transducer repressor. In some embodiments, the effector protein is capable of detecting an activity of a signal transducer activator and/or an activity of a signal transducer repressor. In some embodiments, the synthetic protein circuit comprises one or more circuit components that are capable of increasing a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor. In some embodiments, the synthetic protein circuit comprises one or more circuit components that are capable of increasing a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

In some embodiments, the aberrant signaling involves an active signal transducer repressor and an active signal transducer. In some embodiments, the aberrant signaling involves an inactive signal transducer activator and an active signal transducer. In some embodiments, the aberrant signaling involves an inactive signal transducer. In some embodiments, the aberrant signaling involves an underactive signal transducer. In some embodiments, the aberrant signaling involves a constitutively inactive signal transducer over a period of time. In some embodiments, the aberrant signaling involves an inactive signal transducer repressor and an inactive signal transducer. In some embodiments, the aberrant signaling involves an active signal transducer activator and an inactive signal transducer. In some embodiments, the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof. In some embodiments, the synthetic protein circuit is capable of directly or indirectly inducing cell death in the presence of the aberrant signaling. In some embodiments, the effector protein is capable of directly or indirectly inducing cell death in the presence of aberrant signaling. In some embodiments, the synthetic protein circuit is capable of directly or indirectly inducing cell death when a first level of activation of the first signal transducer is above a first signal transducer activation threshold and/or a second level of activation of the second signal transducer is below a second signal transducer activation threshold. In some embodiments, the effector protein is capable of directly or indirectly inducing cell death when a first level of activation of the first signal transducer is above a first signal transducer activation threshold and/or a second level of activation of the second signal transducer is below a second signal transducer activation threshold.

Disclosed herein include methods of treating a disease or disorder characterized by an aberrant signaling of one or more signal transducers. In some embodiments, the method comprises: expressing a synthetic protein circuit in a cell of a subject in need thereof, the synthetic protein circuit comprising: a first polypeptide comprising a first signal transducer binding domain and a first part of a first protease domain, wherein the first signal transducer binding domain is capable of binding a first signal transducer of the cell to form a first signal transducer-bound polypeptide; a second polypeptide comprising a second signal transducer binding domain and a second part of the first protease domain, wherein the second signal transducer binding domain is capable of binding a second signal transducer of the cell to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting to change the effector protein to an effector active state, or an effector inactive state, which correlates with an aberrant signaling of the first signal transducer and/or the second signal transducer, and wherein the effector protein in the effector active state, or the effector inactive state, is capable of changing a state of the cell, thereby treating a disease or disorder characterized by the aberrant signaling of the first signal transducer and/or the second signal transducer. In some embodiments, the first signal transducer binding domain of the first polypeptide and the second signal transducer binding domain of the second polypeptide are identical. In some embodiments, the first transducer and the second transducer are identical.

Disclosed herein include embodiments of a method of treating a disease or disorder characterized by an aberrant signaling of one or more signal transducers. In some embodiments, the method comprises: expressing a synthetic protein circuit in a cell of a subject in need thereof. The synthetic protein circuit can comprise: a first polypeptide comprising a first signal transducer binding domain and a first part of a first protease domain, wherein the first signal transducer binding domain binds to a first signal transducer of the cell to form a first signal transducer-bound polypeptide. The synthetic protein circuit can comprise: a second polypeptide comprising a second signal transducer binding domain and a second part of the first protease domain, wherein the second signal transducer binding domain binds to a second signal transducer to form a second signal transducer-bound polypeptide, and wherein the first part of the first protease domain and the second part of the first protease domain associate with each other to constitute a first protease in a first protease active state when the first signal transducer and the second signal transducer are in close proximity at an association location. The synthetic circuit can comprise: an effector protein comprising a first cut site the first protease in the first protease active state cuts to change the effector protein to an effector active state (or an effector inactive state), which correlates with an aberrant signaling of the first signal transducer and/or the second signal transducer. The effector protein in the effector active state (the effector inactive state) can change a state of the cell (e.g., the effector protein can induce apoptosis), thereby treating a disease or disorder characterized by the aberrant signaling of the first signal transducer and/or the second signal transducer.

In some embodiments, the first signal transducer, the second signal transducer, or both, localize at the association location. In some embodiments, the first signal transducer when in a first signal transducer active state, the second signal transducer when in a second signal transducer active state, or both, localize at the association location. In some embodiments, the first signal transducer when in a first inactive state, the second signal transducer when in a second inactive state, or both, localize at the association location. In some embodiments, the first signal transducer binding domain of the first polypeptide binds to the first signal transducer, wherein the second signal transducer binding domain of the second polypeptide binds to the second signal transducer, or both. In some embodiments, the first signal transducer binding domain of the first polypeptide binds to the first signal transducer in a first signal transducer active state, wherein the second signal transducer binding domain of the second polypeptide binds to the second signal transducer in a second signal transducer active state, or both. In some embodiments, the first signal transducer binding domain of the first polypeptide binds to the first signal transducer in a first inactive state, wherein the second signal transducer binding domain of the second polypeptide binds to the second signal transducer in a second inactive state, or both. In some embodiments, the signal transducer binding domain of the first polypeptide binds the first signal transducer to form the first signal transducer-bound polypeptide at the association location, wherein the signal transducer binding domain of the first polypeptide binds the first signal transducer to form the first signal transducer-bound polypeptide at the association location, or both. In some embodiments, the signal transducer binding domain of the first polypeptide binds the first signal transducer to form the first signal transducer-bound polypeptide at a first cellular location other than the association location, wherein the signal transducer binding domain of the first polypeptide binds the first signal transducer to form the first signal transducer-bound polypeptide at a second cellular location other than the association location, or both. In some embodiments, the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, micro some, plasma membrane, nuclear membrane, chloroplast, cell wall, or any combination thereof. In some embodiments, the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

In some embodiments, a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state. In some embodiments, a first concentration of the first protease in the first protease active state is at least two-fold higher at the association location as compared a cellular location other than the association location when the first signal transducer is in a first signal transducer active state and/or when the second signal transducer is in a second signal transducer active state. In some embodiments, the first part of the first protease domain and the second part of the first protease domain have the weak association affinity when the first signal transducer is in a first signal transducer inactive state and/or the second signal transducer inactive state. In some embodiments, the first part of the first protease domain and the second part of the first protease domain are incapable of associating to form the first protease in the first protease active state when the first signal transducer is in a first signal transducer inactive state and/or the second signal transducer is in a second signal transducer inactive state. In some embodiments, a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state. In some embodiments, a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state. In some embodiments, the first part of the first protease domain and the second part of the first protease domain associate with each other to form the first protease in the first protease active state at a threshold first polypeptide concentration and a threshold second polypeptide concentration at the association location. In some embodiments, the threshold first polypeptide concentration and the threshold second polypeptide concentration at the association location are reached at a threshold signal transducer activation level of the signal transducer.

In some embodiments, the effector protein changes from an effector inactive state to an effector active state when the first protease in the first protease active state cuts the first cut site of the effector. In some embodiments, a level of activation of the effector protein positively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein changes from an effector active state to an effector inactive state when the first protease in the first protease active state cuts the first cut site of the effector. In some embodiments, a level of activation of the effector protein negatively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein comprises a third signal transducer binding domain, and wherein the third signal transducer binding domain binds the first signal transducer and/or the second signal transducer.

In some embodiments, the synthetic protein circuit further comprises a repressor protein, wherein the repressor protein comprises a second protease. In some embodiments, the second protease in a second protease active state cuts a first cut site of the first polypeptide and/or a second cut site of the second polypeptide. In some embodiments, the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide. In some embodiments, the repressor protein comprises a cut site the first protease in the first protease active state cuts. In some embodiments, the repressor protein is changed into a repressor destabilized state, a repressor delocalized state, and/or a repressor inactivate state after the first protease cuts the cut site of the repressor protein. In some embodiments, the effector protein comprises a second cut site the second protease in the second protease active state cuts. In some embodiments, the effector protein is changed into a first effector destabilized state, a first effector delocalized state, and/or a first effector inactivate state after the second protease in the second protease active state cuts the cut site of the effector protein. In some embodiments, the effector protein comprises a degron, wherein the second protease in the second protease active state cuts the second cut site of the effector protein to expose the degron, and wherein the degron of the effector protein being exposed changes the effector protein to an effector destabilized state. In some embodiments, the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide. In some embodiments, the repressor protein comprises a cut site the first protease in the first protease active state cuts. In some embodiments, the repressor protein is changed into a repressor stabilized state, a repressor localized state, and/or a repressor activate state after the first protease in the first protease active state cuts the first cut site of the repressor protein.

In some embodiments, the effector protein comprises a second cut site the second protease in the second protease active state cuts. In some embodiments, the effector protein is changed into a first effector stabilized state, a first effector localized state, and/or a first effector activate state after the second protease in the second protease active state cuts the second cut site of the effector protein. In some embodiments, the effector protein comprises a degron, wherein the second protease in the second protease active state cuts the second cut site of the effector protein to hide the degron, and wherein the degron of the effector protein being hidden changes the effector protein to an effector stabilized state. In some embodiments, the effector protein changes a synthetic protein circuit component of the synthetic protein circuit to a synthetic protein circuit component active state. In some embodiments, the effector protein comprises a third protease domain, and wherein the third protease domain is changed to an effector inactive state after the second protease in the second protease active state cuts the cute site of the effector protein. In some embodiments, the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector. In some embodiments, the effector protein in an effector active state activates an endogenous signal transduction pathway. In some embodiments, the effector protein in an effector active state inactivates an endogenous signal transduction pathway. In some embodiments, the effector protein comprises Caspase-3, Caspase 7, Caspase-9, Caspase-8, Bax, Bid, Bad, Bak, BCL2L11, p53, PUMA, Diablo/SMAC, S-TRAIL, or any combination thereof. In some embodiments, the effector protein in an effector active state renders a resident cell sensitive to a prodrug. In some embodiments, the effector protein comprises cytosine deaminase and uracil phosphoribosyl transferase, and wherein the prodrug is 5-fluorocytosine (5-FC). In some embodiments, the effector protein comprises thymidine kinase (TK), and the wherein the prodrug comprises ganciclovir.

In some embodiments, two or more of the first signal transducer binding domain, the second signal transducer binding domain, and/or third signal transducer binding domain are identical. In some embodiments, two or more of the first signal transducer binding domain, the second signal transducer binding domain, and/or third signal transducer binding domain are different. In some embodiments, the first signal transducer binding domain, the second signal transducer binding domain, and/or third signal transducer binding domain each bind molecules of the first signal transducer and/or the second signal transducer.

In some embodiments, the third signal transducer binding domain binds to a third signal transducer at the association location. In some embodiments, the first signal transducer, the second signal transducer, and/or the third signal transducer belong to a signal transduction pathway. In some embodiments, the first signal transducer binding domain, the second signal transducer binding domain, and/or the third signal transducer binding domain comprise a RAS binding domain (RBD) and/or RAS association domain (RAD). In some embodiments, the first signal transducer binding domain, the second signal transducer binding domain, and/or the third signal transducer binding domain comprises a lipid binding domain. In some embodiments, the lipid binding domain comprises a Pleckstrin homology (PH) domain. In some embodiments, the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

In some embodiments, the first signal transducer binds the first signal transducer binding domain and/or the second signal transducer binds the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof. In some embodiments, the first signal transducer, the second signal transducer, or both are endogenous proteins. In some embodiments, the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof. In some embodiments, the first signal transducer and/or the second signal transducer regulate cell survival, cell growth, cell proliferation, cell adhesion, cell migration, cell metabolism, cell morphology, cell differentiation, apoptosis, or any combination thereof. In some embodiments, the first signal transducer, the second signal transducer, or both comprise a RAS protein. In some embodiments, the RAS protein is KRAS, NRHAS, HRAS, or any combination thereof. In some embodiments, the first signal transducer, the second signal transducer, or both are exogenous proteins. In some embodiments, the synthetic protein circuit comprises the first signal transducer, the second signal transducer, or both. In some embodiments, the first signal transducer, the second signal transducer, or both comprise a lipid. In some embodiments, the lipid comprises a phospholipid. In some embodiments, the phospholipid is phosphatidylinositol 3-phosphate.

In some embodiments, the synthetic protein circuit detects an activity of the first signal transducer and an activity of the second signal transducer. In some embodiments, an activity of the effector protein correlates with an activity of the first signal transducer and/or an activity of the second signal transducer. In some embodiments, the synthetic protein circuit detects activities of the first signal transducer and activities of the second signal transducer over a period of time. In some embodiments, activities of the effector protein correlate with activities of the first signal transducer and activities of the second signal transducer over a period of time. In some embodiments, the synthetic protein circuit detects an aberrant signaling. In some embodiments, aberrant signaling involves an active signal transducer. In some embodiments, the aberrant signaling involves an overactive signal transducer. In some embodiments, the aberrant signaling involves a constitutively active signal transducer over a period of time. In some embodiments, the synthetic protein circuit detects an activity of a signal transducer activator and/or an activity of a signal transducer repressor. In some embodiments, the effector protein detects an activity of a signal transducer activator and/or an activity of a signal transducer repressor. In some embodiments, the synthetic protein circuit comprises one or more circuit components that increase a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor. In some embodiments, the synthetic protein circuit comprises one or more circuit components that increase a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

In some embodiments, the aberrant signaling involves an active signal transducer repressor and an active signal transducer. In some embodiments, the aberrant signaling involves an inactive signal transducer activator and an active signal transducer. In some embodiments, the aberrant signaling involves an inactive signal transducer. In some embodiments, the aberrant signaling involves an underactive signal transducer. In some embodiments, the aberrant signaling involves a constitutively inactive signal transducer over a period of time. In some embodiments, the aberrant signaling involves an inactive signal transducer repressor and an inactive signal transducer. In some embodiments, the aberrant signaling involves an active signal transducer activator and an inactive signal transducer. In some embodiments, the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof. In some embodiments, the synthetic protein circuit directly or indirectly induces cell death in the presence of the aberrant signaling. In some embodiments, the effector protein directly or indirectly induces cell death in the presence of aberrant signaling. In some embodiments, the synthetic protein circuit directly or indirectly induces cell death when a first level of activation of the first signal transducer is above a first signal transducer activation threshold and/or a second level of activation of the second signal transducer is below a second signal transducer activation threshold. In some embodiments, the effector protein directly or indirectly induces cell death when a first level of activation of the first signal transducer is above a first signal transducer activation threshold and/or a second level of activation of the second signal transducer is below a second signal transducer activation threshold.

In some embodiments, the disease or disorder is characterized by an aberrant signaling of the first transducer. In some embodiments, the disease or disorder is characterized by an aberrant signaling of the first transducer and an aberrant signaling of the second transducer, and wherein the first transducer and the second transducer are identical. In some embodiments, the disease or disorder is characterized by an aberrant signaling of the first transducer and an aberrant signaling of the second transducer, and wherein the first transducer and the second transducer are different. In some embodiments, the disease or disorder is characterized by an aberrant signaling of a RAS protein. In some embodiments, the disease or disorder is a cancer. In some embodiments, the disease or disorder is a RASopathy selected from the group comprising Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, Legius syndrome, or any combination thereof. In some embodiments, the disease is a neurological disease or a neurodegenerative disease. In some embodiments, the disease is an autoimmune disease. In some embodiments, the disease is infectious disease.

In some embodiments, the method comprises administering a prodrug. In some embodiments, the prodrug is 5-fluorocytosine (5-FC) or ganciclovir. In some embodiments, the expressing comprises administering a nucleic acid encoding the synthetic protein circuit. In some embodiments, the expressing comprises administering two or more nucleic acids, wherein the two or more nucleic acids encode the synthetic protein circuit. In some embodiments, the nucleic acid comprises at least one regulatory element for expression of the synthetic protein circuit. In some embodiments, the nucleic acid comprises a vector. In some embodiments, the vector comprises an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector comprises an RNA viral vector. In some embodiments, the vector is derived from one or more negative-strand RNA viruses of the order Mononegavirales. In some embodiments, the vector is a rabies viral vector. In some embodiments, the administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof.

Disclosed herein include methods of measuring a level of activation of one or more signal transducers. In some embodiments, the method comprises: expressing a synthetic protein circuit in a cell of a subject in need thereof, the synthetic protein circuit comprising: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting, wherein a level of activation of the effector protein indicates a first level of activation of the first signal transducer and/or a second level of activation of the second signal transducer. In some embodiments, the first signal transducer binding domain of the first polypeptide and the second signal transducer binding domain of the second polypeptide are identical. In some embodiments, the first transducer and the second transducer are identical.

Disclosed herein include embodiments of a method of measuring a level of activation of one or more signal transducers. In some embodiments, the method comprises: expressing a synthetic protein circuit in a cell of a subject in need thereof. The synthetic protein circuit can comprise: a first polypeptide comprising a first signal transducer binding domain and a first part of a first protease domain, wherein the first signal transducer binding domain binds to a first signal transducer of the cell to form a first signal transducer-bound polypeptide. The synthetic circuit can comprise: a second polypeptide comprising a second signal transducer binding domain and a second part of the first protease domain, wherein the second signal transducer binding domain binds to a second signal transducer to form a second signal transducer-bound polypeptide, and wherein the first part of the first protease domain and the second part of the first protease domain associate with each other to constitute a first protease in a first protease active state when the first signal transducer and the second signal transducer are in close proximity at an association location. The synthetic circuit can comprise: an effector protein comprising a first cut site the first protease in the first protease active state cuts to change an activity state/a level of activation of the effector protein. The activity state/the level of activation of the effector protein can indicate a first level of activation of the first signal transducer and/or a second level of activation of the second signal transducer.

In some embodiments, the first signal transducer, the second signal transducer, or both, localize at the association location. In some embodiments, the first signal transducer when in a first signal transducer active state, the second signal transducer when in a second signal transducer active state, or both, localize at the association location. In some embodiments, the first signal transducer when in a first inactive state, the second signal transducer when in a second inactive state, or both, localize at the association location. In some embodiments, the first signal transducer binding domain of the first polypeptide binds to the first signal transducer, wherein the second signal transducer binding domain of the second polypeptide binds to the second signal transducer, or both. In some embodiments, the first signal transducer binding domain of the first polypeptide binds to the first signal transducer in a first signal transducer active state, wherein the second signal transducer binding domain of the second polypeptide binds to the second signal transducer in a second signal transducer active state, or both. In some embodiments, the first signal transducer binding domain of the first polypeptide binds to the first signal transducer in a first inactive state, wherein the second signal transducer binding domain of the second polypeptide binds to the second signal transducer in a second inactive state, or both. In some embodiments, the signal transducer binding domain of the first polypeptide binds the first signal transducer to form the first signal transducer-bound polypeptide at the association location, wherein the signal transducer binding domain of the first polypeptide binds the first signal transducer to form the first signal transducer-bound polypeptide at the association location, or both. In some embodiments, the signal transducer binding domain of the first polypeptide binds the first signal transducer to form the first signal transducer-bound polypeptide at a first cellular location other than the association location, wherein the signal transducer binding domain of the first polypeptide binds the first signal transducer to form the first signal transducer-bound polypeptide at a second cellular location other than the association location, or both. In some embodiments, the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof. In some embodiments, the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

In some embodiments, a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state. In some embodiments, a first concentration of the first protease in the first protease active state is at least two-fold higher at the association location as compared a cellular location other than the association location when the first signal transducer is in a first signal transducer active state and/or when the second signal transducer is in a second signal transducer active state. In some embodiments, the first part of the first protease domain and the second part of the first protease domain have the weak association affinity when the first signal transducer is in a first signal transducer inactive state and/or the second signal transducer inactive state. In some embodiments, the first part of the first protease domain and the second part of the first protease domain are incapable of associating to form the first protease in the first protease active state when the first signal transducer is in a first signal transducer inactive state and/or the second signal transducer is in a second signal transducer inactive state. In some embodiments, a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state. In some embodiments, a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state. In some embodiments, the first part of the first protease domain and the second part of the first protease domain associate with each other to form the first protease in the first protease active state at a threshold first polypeptide concentration and a threshold second polypeptide concentration at the association location. In some embodiments, the threshold first polypeptide concentration and the threshold second polypeptide concentration at the association location are reached at a threshold signal transducer activation level of the signal transducer.

In some embodiments, the effector protein changes from an effector inactive state to an effector active state when the first protease in the first protease active state cuts the first cut site of the effector. In some embodiments, a level of activation of the effector protein positively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein changes from an effector active state to an effector inactive state when the first protease in the first protease active state cuts the first cut site of the effector. In some embodiments, a level of activation of the effector protein negatively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein comprises a third signal transducer binding domain, and wherein the third signal transducer binding domain binds the first signal transducer and/or the second signal transducer.

In some embodiments, the synthetic protein circuit further comprises a repressor protein, wherein the repressor protein comprises a second protease. In some embodiments, the second protease in a second protease active state cuts a first cut site of the first polypeptide and/or a second cut site of the second polypeptide. In some embodiments, the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide. In some embodiments, the repressor protein comprises a cut site the first protease in the first protease active state cuts. In some embodiments, the repressor protein is changed into a repressor destabilized state, a repressor delocalized state, and/or a repressor inactivate state after the first protease cuts the cut site of the repressor protein. In some embodiments, the effector protein comprises a second cut site the second protease in the second protease active state cuts. In some embodiments, the effector protein is changed into a first effector destabilized state, a first effector delocalized state, and/or a first effector inactivate state after the second protease in the second protease active state cuts the cut site of the effector protein. In some embodiments, the effector protein comprises a degron, wherein the second protease in the second protease active state cuts the second cut site of the effector protein to expose the degron, and wherein the degron of the effector protein being exposed changes the effector protein to an effector destabilized state. In some embodiments, the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide. In some embodiments, the repressor protein comprises a cut site the first protease in the first protease active state cuts. In some embodiments, the repressor protein is changed into a repressor stabilized state, a repressor localized state, and/or a repressor activate state after the first protease in the first protease active state cuts the first cut site of the repressor protein. In some embodiments, the effector protein comprises a second cut site the second protease in the second protease active state cuts. In some embodiments, the effector protein is changed into a first effector stabilized state, a first effector localized state, and/or a first effector activate state after the second protease in the second protease active state cuts the second cut site of the effector protein. In some embodiments, the effector protein comprises a degron, wherein the second protease in the second protease active state cuts the second cut site of the effector protein to hide the degron, and wherein the degron of the effector protein being hidden changes the effector protein to an effector stabilized state. In some embodiments, the effector protein changes a synthetic protein circuit component of the synthetic protein circuit to a synthetic protein circuit component active state. In some embodiments, the effector protein comprises a third protease domain, and wherein the third protease domain is changed to an effector inactive state after the second protease in the second protease active state cuts the cute site of the effector protein. In some embodiments, the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector.

In some embodiments, two or more of the first signal transducer binding domain, the second signal transducer binding domain, and/or third signal transducer binding domain are identical. In some embodiments, two or more of the first signal transducer binding domain, the second signal transducer binding domain, and/or third signal transducer binding domain are different. In some embodiments, the first signal transducer binding domain, the second signal transducer binding domain, and/or third signal transducer binding domain each bind molecules of the first signal transducer and/or the second signal transducer. In some embodiments, the third signal transducer binding domain binds to a third signal transducer at the association location. In some embodiments, the first signal transducer, the second signal transducer, and/or the third signal transducer belong to a signal transduction pathway. In some embodiments, the first signal transducer binding domain, the second signal transducer binding domain, and/or the third signal transducer binding domain comprise a RAS binding domain (RBD) and/or RAS association domain (RAD). In some embodiments, the first signal transducer binding domain, the second signal transducer binding domain, and/or the third signal transducer binding domain comprises a lipid binding domain. In some embodiments, the lipid binding domain comprises a Pleckstrin homology (PH) domain. In some embodiments, the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

In some embodiments, the first signal transducer binds the first signal transducer binding domain and/or the second signal transducer binds the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof. In some embodiments, the first signal transducer, the second signal transducer, or both are endogenous proteins. In some embodiments, first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof. In some embodiments, the first signal transducer and/or the second signal transducer regulate cell survival, cell growth, cell proliferation, cell adhesion, cell migration, cell metabolism, cell morphology, cell differentiation, apoptosis, or any combination thereof. In some embodiments, the first signal transducer, the second signal transducer, or both comprise a RAS protein. In some embodiments, the RAS protein is KRAS, NRHAS, HRAS, or any combination thereof. In some embodiments, the first signal transducer, the second signal transducer, or both are exogenous proteins. In some embodiments, the synthetic protein circuit comprises the first signal transducer, the second signal transducer, or both. In some embodiments, the first signal transducer, the second signal transducer, or both comprise a lipid. In some embodiments, the lipid comprises a phospholipid. In some embodiments, the phospholipid is phosphatidylinositol 3-phosphate.

In some embodiments, the synthetic protein circuit detects an activity of the first signal transducer and an activity of the second signal transducer. In some embodiments, an activity of the effector protein correlates with an activity of the first signal transducer and/or an activity of the second signal transducer. In some embodiments, the synthetic protein circuit detects activities of the first signal transducer and activities of the second signal transducer over a period of time. In some embodiments, activities of the effector protein correlate with activities of the first signal transducer and activities of the second signal transducer over a period of time. In some embodiments, the synthetic protein circuit detects an activity of a signal transducer activator and/or an activity of a signal transducer repressor. In some embodiments, the effector protein detects an activity of a signal transducer activator and/or an activity of a signal transducer repressor. In some embodiments, the synthetic protein circuit comprises one or more circuit components that increase a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor. In some embodiments, the synthetic protein circuit comprises one or more circuit components that increase a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor. In some embodiments, the effector protein in an effector active state is capable of generating a first detectable signal. In some embodiments, the effector protein in an effector inactive state is capable of generating a second detectable signal. In some embodiments, the fluorescence emission intensity, fluorescence lifetime, excitation wavelength, and/or emission wavelength of the first detectable signal and second detectable signal are different. In some embodiments, the method comprises detecting the first detectable signal and/or second detectable signal. In some embodiments, detecting the first detectable signal and/or second detectable signal comprises illumination of the effector protein. In some embodiments, the effector protein comprises all or a portion of a fluorescent protein, a luminescent protein, a phosphorescent protein, or any combination thereof. In some embodiments, the effector protein comprises all or a portion of Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, ZsYellow1, DsRed2, AsRed2, and HcRed1, or any combination thereof. In some embodiments, one or more of the fluorescence emission intensity, fluorescence lifetime, excitation wavelength, and/or emission wavelength of the first detectable signal positively correlates with a level of activation of the effector protein. In some embodiments, one or more of the fluorescence emission intensity, fluorescence lifetime, excitation wavelength, and/or emission wavelength of the first detectable signal and/or second detectable signal positively correlates with a first level of activation of the first signal transducer and/or a second level of activation of the second signal transducer.

In some embodiments, the first detectable signal and/or second detectable signal can indicate and/or quantify aberrant signaling. In some embodiments, aberrant signaling involves an active signal transducer. In some embodiments, the aberrant signaling involves an overactive signal transducer. In some embodiments, the aberrant signaling involves a constitutively active signal transducer over a period of time. In some embodiments, the aberrant signaling involves an active signal transducer repressor and an active signal transducer. In some embodiments, the aberrant signaling involves an inactive signal transducer activator and an active signal transducer. In some embodiments, the aberrant signaling involves an inactive signal transducer. In some embodiments, the aberrant signaling involves an underactive signal transducer. In some embodiments, the aberrant signaling involves a constitutively inactive signal transducer over a period of time. In some embodiments, the aberrant signaling involves an inactive signal transducer repressor and an inactive signal transducer. In some embodiments, the aberrant signaling involves an active signal transducer activator and an inactive signal transducer. In some embodiments, the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

In some embodiments, the expressing comprises administering a nucleic acid encoding the synthetic protein circuit. In some embodiments, the expressing comprises administering two or more nucleic acids, wherein the two or more nucleic acids encode the synthetic protein circuit. In some embodiments, the nucleic acid comprises at least one regulatory element for expression of the synthetic protein circuit. In some embodiments, the nucleic acid comprises a vector. In some embodiments, the vector comprises an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector comprises an RNA viral vector. In some embodiments, the vector is derived from one or more negative-strand RNA viruses of the order Mononegavirales. In some embodiments, the vector is a rabies viral vector. In some embodiments, the administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof.

Disclosed herein include nucleic acids encoding a synthetic protein circuit. In some embodiments, the nucleic acid encodes a synthetic protein circuit comprising: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting.

In some embodiments, the first signal transducer binding domain of the first polypeptide and the second signal transducer binding domain of the second polypeptide are identical. In some embodiments, the first transducer and the second transducer are identical. In some embodiments, the first signal transducer, the second signal transducer, or both, are capable of being localized at the association location. In some embodiments, the first signal transducer when in a first signal transducer active state, the second signal transducer when in a second signal transducer active state, or both, are capable of being localized at the association location. In some embodiments, the first signal transducer when in a first inactive state, the second signal transducer when in a second inactive state, or both, are capable of being localized at the association location. In some embodiments, the first signal transducer binding domain of the first polypeptide is capable of binding to the first signal transducer, wherein the second signal transducer binding domain of the second polypeptide is capable of binding to the second signal transducer, or both. In some embodiments, the first signal transducer binding domain of the first polypeptide is capable of binding to the first signal transducer in a first signal transducer active state, wherein the second signal transducer binding domain of the second polypeptide is capable of binding to the second signal transducer in a second signal transducer active state, or both. In some embodiments, the first signal transducer binding domain of the first polypeptide is capable of binding to the first signal transducer in a first inactive state, wherein the second signal transducer binding domain of the second polypeptide is capable of binding to the second signal transducer in a second inactive state, or both. In some embodiments, the signal transducer binding domain of the first polypeptide is capable of binding the first signal transducer to form the first signal transducer-bound polypeptide at the association location, wherein the signal transducer binding domain of the first polypeptide is capable of binding the first signal transducer to form the first signal transducer-bound polypeptide at the association location, or both. In some embodiments, the signal transducer binding domain of the first polypeptide is capable of binding the first signal transducer to form the first signal transducer-bound polypeptide at a first cellular location other than the association location, wherein the signal transducer binding domain of the first polypeptide is capable of binding the first signal transducer to form the first signal transducer-bound polypeptide at a second cellular location other than the association location, or both. In some embodiments, the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof. In some embodiments, the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

In some embodiments, a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state. In some embodiments, a first concentration of the first protease in the first protease active state is at least two-fold higher at the association location as compared a cellular location other than the association location when the first signal transducer is in a first signal transducer active state and/or when the second signal transducer is in a second signal transducer active state. In some embodiments, the first part of the first protease domain and the second part of the first protease domain have the weak association affinity when the first signal transducer is in a first signal transducer inactive state and/or the second signal transducer inactive state. In some embodiments, the first part of the first protease domain and the second part of the first protease domain are incapable of associating to form the first protease in the first protease active state when the first signal transducer is in a first signal transducer inactive state and/or the second signal transducer is in a second signal transducer inactive state. In some embodiments, a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state. In some embodiments, a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state. In some embodiments, the first part of the first protease domain and the second part of the first protease domain are capable of associating with each other to form the first protease in the first protease active state at a threshold first polypeptide concentration and a threshold second polypeptide concentration at the association location. In some embodiments, the threshold first polypeptide concentration and the threshold second polypeptide concentration at the association location are reached at a threshold signal transducer activation level of the signal transducer.

In some embodiments, the effector protein changes from an effector inactive state to an effector active state when the first protease in the first protease active state cuts the first cut site of the effector. In some embodiments, a level of activation of the effector protein positively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein changes from an effector active state to an effector inactive state when the first protease in the first protease active state cuts the first cut site of the effector. In some embodiments, a level of activation of the effector protein negatively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state. In some embodiments, the effector protein comprises a third signal transducer binding domain, and wherein the third signal transducer binding domain is capable of binding the first signal transducer and/or the second signal transducer.

In some embodiments, the synthetic protein circuit further comprises a repressor protein, wherein the repressor protein comprises a second protease. comprises the second protease in a second protease active state is capable of cutting a first cut site of the first polypeptide and/or a second cut site of the second polypeptide. In some embodiments, the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide. In some embodiments, the repressor protein comprises a cut site the first protease in the first protease active state is capable of cutting. In some embodiments, the repressor protein is changed into a repressor destabilized state, a repressor delocalized state, and/or a repressor inactivate state after the first protease cuts the cut site of the repressor protein. In some embodiments, the effector protein comprises a second cut site the second protease in the second protease active state is capable of cutting. In some embodiments, the effector protein is changed into a first effector destabilized state, a first effector delocalized state, and/or a first effector inactivate state after the second protease in the second protease active state cuts the cut site of the effector protein. In some embodiments, the effector protein comprises a degron, wherein the second protease in the second protease active state is capable of cutting the second cut site of the effector protein to expose the degron, and wherein the degron of the effector protein being exposed changes the effector protein to an effector destabilized state. In some embodiments, the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide.

In some embodiments, the repressor protein comprises a cut site the first protease in the first protease active state is capable of cutting. In some embodiments, the repressor protein is changed into a repressor stabilized state, a repressor localized state, and/or a repressor activate state after the first protease in the first protease active state cuts the first cut site of the repressor protein. In some embodiments, the effector protein comprises a second cut site the second protease in the second protease active state is capable of cutting. In some embodiments, the effector protein is changed into a first effector stabilized state, a first effector localized state, and/or a first effector activate state after the second protease in the second protease active state cuts the second cut site of the effector protein. In some embodiments, the effector protein comprises a degron, wherein the second protease in the second protease active state is capable of cutting the second cut site of the effector protein to hide the degron, and wherein the degron of the effector protein being hidden changes the effector protein to an effector stabilized state. In some embodiments, the effector protein is capable of changing a synthetic protein circuit component of the synthetic protein circuit to a synthetic protein circuit component active state. In some embodiments, the effector protein comprises a third protease domain, and wherein the third protease domain is changes to an effector inactive state after the second protease in the second protease active state cuts the cute site of the effector protein. In some embodiments, the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector. In some embodiments, the effector protein in an effector active state is capable of activating an endogenous signal transduction pathway. In some embodiments, the effector protein in an effector active state is capable of inactivating an endogenous signal transduction pathway. In some embodiments, the effector protein comprises Caspase-3, Caspase 7, Caspase-9, Caspase-8, Bax, Bid, Bad, Bak, BCL2L11, p53, PUMA, Diablo/SMAC, S-TRAIL, or any combination thereof. In some embodiments, the effector protein in an effector active state is capable of rendering a resident cell sensitive to a prodrug. In some embodiments, the effector protein comprises cytosine deaminase and uracil phosphoribosyl transferase, and wherein the prodrug is 5-fluorocytosine (5-FC). In some embodiments, the effector protein comprises thymidine kinase (TK), and the wherein the prodrug comprises ganciclovir.

In some embodiments, two or more of the first signal transducer binding domain, the second signal transducer binding domain, and/or third signal transducer binding domain are identical. In some embodiments, two or more of the first signal transducer binding domain, the second signal transducer binding domain, and/or third signal transducer binding domain are different. In some embodiments, the first signal transducer binding domain, the second signal transducer binding domain, and/or third signal transducer binding domain each is capable of binding molecules of the first signal transducer and/or the second signal transducer. In some embodiments, the third signal transducer binding domain is capable of binding to a third signal transducer at the association location. In some embodiments, the first signal transducer, the second signal transducer, and/or the third signal transducer belong to a signal transduction pathway. In some embodiments, the first signal transducer binding domain, the second signal transducer binding domain, and/or the third signal transducer binding domain comprise a RAS binding domain (RBD) and/or RAS association domain (RAD). In some embodiments, the first signal transducer binding domain, the second signal transducer binding domain, and/or the third signal transducer binding domain comprises a lipid binding domain. In some embodiments, the lipid binding domain comprises a Pleckstrin homology (PH) domain. In some embodiments, the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

In some embodiments, the first signal transducer is capable of binding the first signal transducer binding domain and/or the second signal transducer is capable of binding the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof. In some embodiments, the first signal transducer, the second signal transducer, or both are endogenous proteins. In some embodiments, the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof. In some embodiments, the first signal transducer and/or the second signal transducer are capable of regulating cell survival, cell growth, cell proliferation, cell adhesion, cell migration, cell metabolism, cell morphology, cell differentiation, apoptosis, or any combination thereof. In some embodiments, the first signal transducer, the second signal transducer, or both comprise a RAS protein. In some embodiments, the RAS protein is KRAS, NRHAS, HRAS, or any combination thereof. In some embodiments, the first signal transducer, the second signal transducer, or both are exogenous proteins. In some embodiments, the synthetic protein circuit comprises the first signal transducer, the second signal transducer, or both. In some embodiments, the first signal transducer, the second signal transducer, or both comprise a lipid. In some embodiments, the lipid comprises a phospholipid. In some embodiments, the phospholipid is phosphatidylinositol 3-phosphate.

In some embodiments, the synthetic protein circuit is capable of detecting an activity of the first signal transducer and an activity of the second signal transducer. In some embodiments, an activity of the effector protein correlates with an activity of the first signal transducer and/or an activity of the second signal transducer. In some embodiments, the synthetic protein circuit is capable of detecting activities of the first signal transducer and activities of the second signal transducer over a period of time. In some embodiments, activities of the effector protein correlate with activities of the first signal transducer and activities of the second signal transducer over a period of time. In some embodiments, the synthetic protein circuit is capable of detecting an aberrant signaling. In some embodiments, aberrant signaling involves an active signal transducer. In some embodiments, the aberrant signaling involves an overactive signal transducer. In some embodiments, the aberrant signaling involves a constitutively active signal transducer over a period of time. In some embodiments, the synthetic protein circuit is capable of detecting an activity of a signal transducer activator and/or an activity of a signal. In some embodiments, the effector protein is capable of detecting an activity of a signal transducer activator and/or an activity of a signal transducer repressor. In some embodiments, the synthetic protein circuit comprises one or more circuit components that are capable of increasing a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor. In some embodiments, the synthetic protein circuit comprises one or more circuit components that are capable of increasing a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

In some embodiments, the aberrant signaling involves an active signal transducer repressor and an active signal transducer. In some embodiments, the aberrant signaling involves an inactive signal transducer activator and an active signal transducer. In some embodiments, the aberrant signaling involves an inactive signal transducer. In some embodiments, the aberrant signaling involves an underactive signal transducer. In some embodiments, the aberrant signaling involves a constitutively inactive signal transducer over a period of time. In some embodiments, the aberrant signaling involves an inactive signal transducer repressor and an inactive signal transducer. In some embodiments, the aberrant signaling involves an active signal transducer activator and an inactive signal transducer. In some embodiments, the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof. In some embodiments, the synthetic protein circuit is capable of directly or indirectly inducing cell death in the presence of the aberrant signaling. In some embodiments, the effector protein is capable of directly or indirectly inducing cell death in the presence of aberrant signaling. In some embodiments, the synthetic protein circuit is capable of directly or indirectly inducing cell death when a first level of activation of the first signal transducer is above a first signal transducer activation threshold and/or a second level of activation of the second signal transducer is below a second signal transducer activation threshold. In some embodiments, the effector protein is capable of directly or indirectly inducing cell death when a first level of activation of the first signal transducer is above a first signal transducer activation threshold and/or a second level of activation of the second signal transducer is below a second signal transducer activation threshold.

In some embodiments, the first polypeptide, the second polypeptide, the effector protein, and/or the repressor protein are encoded on a single open reading frame, and wherein two or more of the first polypeptide, the second polypeptide, the effector protein, and repressor protein are separated by one or more self-cleaving peptides. In some embodiments, the first polypeptide, the second polypeptide, the effector protein, and/or the repressor protein are encoded on a single transcript, and wherein translations of the first polypeptide, the second polypeptide, the effector protein, and/or the repressor protein are each driven by a separate internal ribosome entry site. In some embodiments, the sequences of the internal ribosome entry sites are identical. In some embodiments, the sequences of the internal ribosome entry sites are different. In some embodiments, the nucleic acid comprises a vector. In some embodiments, the vector comprises an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector comprises an RNA viral vector. In some embodiments, the vector is derived from one or more negative-strand RNA viruses of the order Mononegavirales. In some embodiments, the vector is a rabies viral vector.

BRIEF DESCRIPTION OF THE DRAWINGS

FIGS. 3A-3E depicts data related to detection of active Ras signaling with synthetic protein circuits provided herein.

FIG. 7A shows a non-limiting exemplary schematic illustration of how a protease-activatable reporter can be stabilized by removal of a DHFR degron through protease cleavage of a corresponding target site. TMP can inhibit the degron, thereby stabilizing the reporter.

FIG. 7B shows a non-limiting exemplary schematic illustration of how in a protease-repressible reporter, protease cleavage exposes an N-end degron (covered target) to destabilize reporter.

FIG. 11A shows a non-limiting exemplary schematic illustration of bandpass filtering, wherein the expression of co-regulated inputs TEVP and TVMVP were controlled by the amount of transfected DNA, or by doxycycline (square) induction. The amount of HCVP plasmid can be varied to tune the repression arm. FIG. 11B shows a non-limiting exemplary schematic illustration of how delayed repression can enable pulse generation. For example, rapamycin-induced dimerization of FKBP and FRB domains can reconstitute TEVP. Cleavage of the reporter by TEVP can allow maturation of far-red fluorescent protein (IFP).

DETAILED DESCRIPTION

Figure 1A:
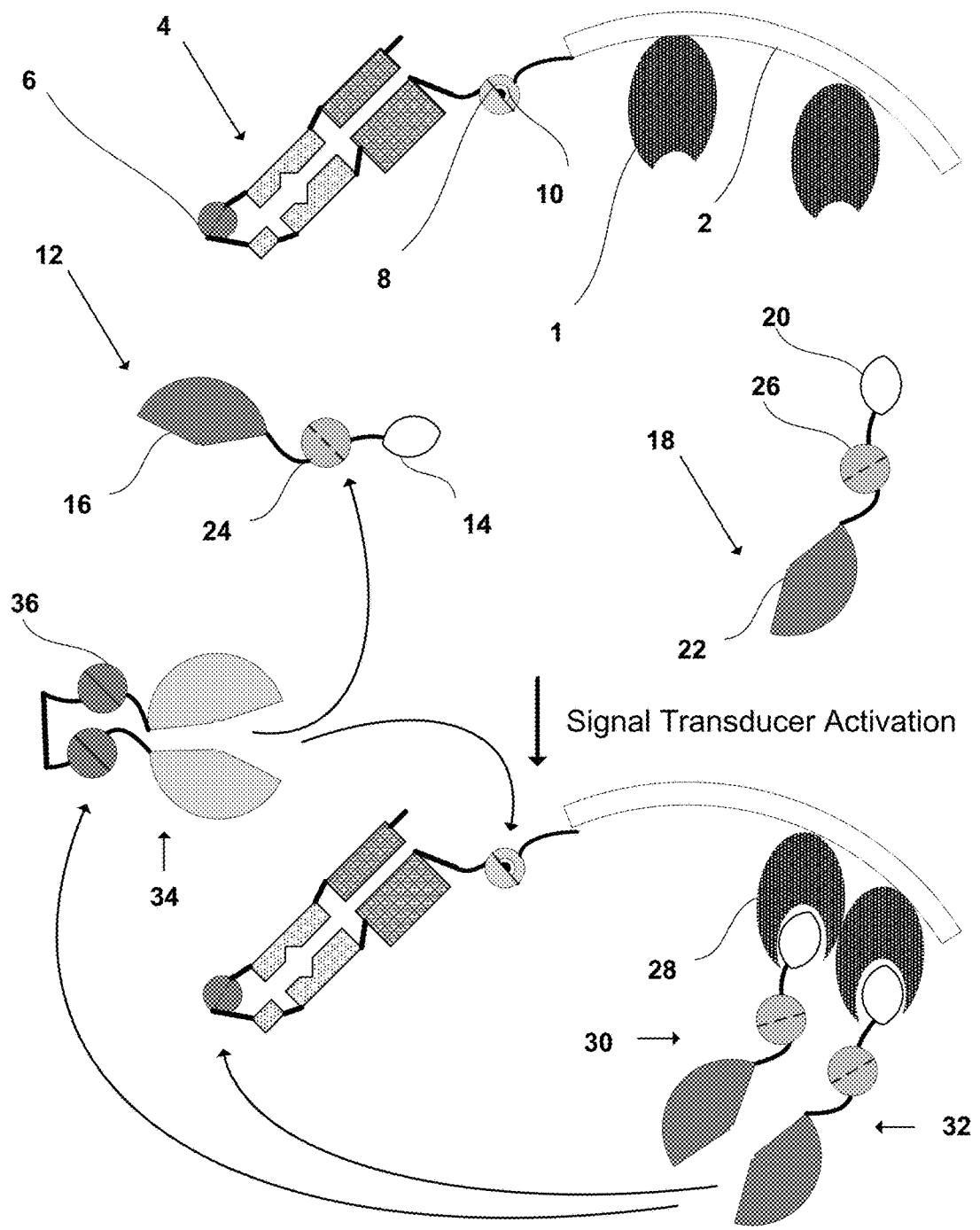
FIG. 1A-1C show non-limiting exemplary schematic illustrations of synthetic protein circuits provided herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include synthetic protein circuits. In some embodiments, the synthetic protein circuit comprises: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting.

Disclosed herein include methods of treating a disease or disorder characterized by an aberrant signaling of one or more signal transducers. In some embodiments, the method comprises: expressing a synthetic protein circuit in a cell of a subject in need thereof, the synthetic protein circuit comprising: a first polypeptide comprising a first signal transducer binding domain and a first part of a first protease domain, wherein the first signal transducer binding domain is capable of binding a first signal transducer of the cell to form a first signal transducer-bound polypeptide; a second polypeptide comprising a second signal transducer binding domain and a second part of the first protease domain, wherein the second signal transducer binding domain is capable of binding a second signal transducer of the cell to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting to change the effector protein to an effector active state, or an effector inactive state, which correlates with an aberrant signaling of the first signal transducer and/or the second signal transducer, and wherein the effector protein in the effector active state, or the effector inactive state, is capable of changing a state of the cell, thereby treating a disease or disorder characterized by the aberrant signaling of the first signal transducer and/or the second signal transducer.

Disclosed herein include methods of measuring a level of activation of one or more signal transducers. In some embodiments, the method comprises: expressing a synthetic protein circuit in a cell of a subject in need thereof, the synthetic protein circuit comprising: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting, wherein a level of activation of the effector protein indicates a first level of activation of the first signal transducer and/or a second level of activation of the second signal transducer.

Disclosed herein include nucleic acids encoding a synthetic protein circuit. In some embodiments, the nucleic acid encodes a synthetic protein circuit comprising: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

As used herein, the term "vector" refers to a polynucleotide construct, typically a plasmid or a virus, used to transmit genetic material to a host cell (e.g., a target cell). Vectors can be, for example, viruses, plasmids, cosmids, or phage. A vector can be a viral vector. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The terms "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, 2A sequences or elements refer to small peptides introduced as a linker between two proteins, allowing autonomous intraribosomal self-processing of polyproteins (See e.g., de Felipe. Genetic Vaccines and Ther. 2: 13 (2004); de Felipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The terms "treat" and "treatment" include, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may reduce the level of RAS signaling in the subject, thereby to reduce, alleviate, or eradicate the symptom(s) of the disease(s). As used herein, the term "prevention" refers to any activity that reduces the burden of the individual later expressing those RAS-related disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, ammo acids, carbohydrates including glucose, mannose, or dextrins, chelating agents such as EDTA, sugar alcohols such as mannitol or sorbitol, salt-forming counterions such as sodium, and nonionic surfactants such as Tween, polyethylene glycol (PEG), and Pluronics. Auxiliary, stabilizer, emulsifier, lubricant, binder, pH adjuster controller, isotonic agent and other conventional additives may also be added to the carriers.

Synthetic Protein Circuits

Many diseases and disorders are caused by aberrant signaling of one or more signal transducers. For example, many oncogenic mutations are activating mutations in growth-promoting signal transducers. Methods to selectively kill or inactivate cells with oncogenic mutations could provide therapeutic strategies for cancer treatment. Synthetic biology allows for rational design of circuits that confer new functions in living cells. Many natural cellular functions are implemented by protein-level circuits, in which proteins specifically modify each other's activity, localization, or stability. Synthetic protein circuits have been described in, Gao, Xiaojing J., et al. "Programmable protein circuits in living cells." Science 361.6408 (2018): 1252-1258; and PCT Application published as WO 2019/147478; the content of each of these, including any supporting or supplemental information or material, is incorporated herein by reference in its entirety. While it was demonstrated therein that synthetic protein circuits could be configured to transduce upstream activators of the oncogene Ras into the activity of engineered proteases, and that these activities could be used to induce cell death, these circuits could not detect Ras directly. The most prevalent and pharmaceutically challenging oncogenic mutations are within Ras itself, and thus would not detected by such protein circuits. Thus, there is an urgent need for compositions, methods, and systems that enable the direct detection of the activity of signal transducers (such as Ras).

The synthetic protein circuits and methods provided herein address the above-mentioned needs. In some embodiments, the synthetic protein circuits employ a new circuit design concept provided herein (termed 'enrichment through translocation') that enables direct detection of signal transducer activity. This novel design concept can rely, in some embodiments, on the enrichment of synthetic protein circuit components at an association location. In some embodiments, this enrichment at the association location is dependent on the activation state of a signal transducer. The increased local concentration of synthetic protein circuit components (e.g., split proteases) at the association location can result in a reconstitution of an activity (e.g., protease activity). This reconstituted activity effectuates the activation of an effector protein. An effector protein in an effector activated state can be configured to carry out a wide variety of functions depending on the need of the user (such as, for example, inducing cell death in response to overactive signaling of an oncogenic signal transducer). Moreover, the synthetic protein circuits provided herein can be configured in numerous ways to generate regulatory cascades, binary logic gates, and dynamic analog signal-processing functions. The flexibility and scalability of this system enables it to be reconfigured to implement a broad range of additional functions.

FIG. 1A depicts a non-limiting exemplary embodiment of a synthetic protein circuit provided herein. A signal transducer (e.g., inactive Ras 1) can be localized at an association location 2 (e.g., membrane). The effector protein 4 (e.g. TEV protease-activated fluorescence reporter) can comprise a cut site 6 a first protease in the first protease active state is capable of cutting. The effector protein can change from an effector inactive state to an effector active state (e.g., a fluorescent state) when the first protease in the first protease active state cuts the cut site 6 of the effector. The effector protein 4 can comprises a cut site 8 a second protease in a second protease active state is capable of cutting. The effector protein can comprise a degron 10. The second protease in the second protease active state can be capable of cutting cut site 8 of the effector protein to expose the degron 10. A first polypeptide 12 can comprise a first signal transducer binding domain 14 and a first part of a first protease domain 16 (e.g., a first TEV protease halve). A second polypeptide 18 can comprise a second signal transducer binding domain 20 and a second part of a first protease domain 22 (e.g., a second TEV protease halve). A second protease in a second protease active state can be capable of cutting a first cut site 24 of the first polypeptide and/or a second cut site 26 of the second polypeptide. The first part of the first protease domain 16 and the second part of the first protease domain 22 can have weak association affinity, and therefore do not reconstitute the first protease. Activation of the signal transducer can cause the signal transducer to adopt an active conformation 28 recognized by first signal transducer binding domain 14 and second signal transducer binding domain 20 resulting in the formation of a first signal transducer-bound polypeptide 30 and a second signal transducer-bound polypeptide 32 at the localization location 2. The first signal transducer-bound polypeptide 30 and a second signal transducer-bound polypeptide 32 are thereby in close proximity at the association location, and thereby associate with each other to constitute a first protease capable of being in a first protease active state, and thereby activate the effector protein 4 by cutting effector cut site 6.

The synthetic protein circuit can comprise a 'core circuit' comprising the first polypeptide 12, effector protein 4, and second polypeptide 18. The synthetic protein circuit can comprise a 'full circuit' comprising the first polypeptide 12, effector protein 4, and second polypeptide 18, and further comprising a repressor protein 34 comprising a second protease domain (e.g., TMVM). The repressor protein 34 can comprise a cut site 36 the first protease in the first protease active state is capable of cutting, thereby converting the second protease in a second protease active state to a second protease in a second protease inactive state.

Figure 1B:
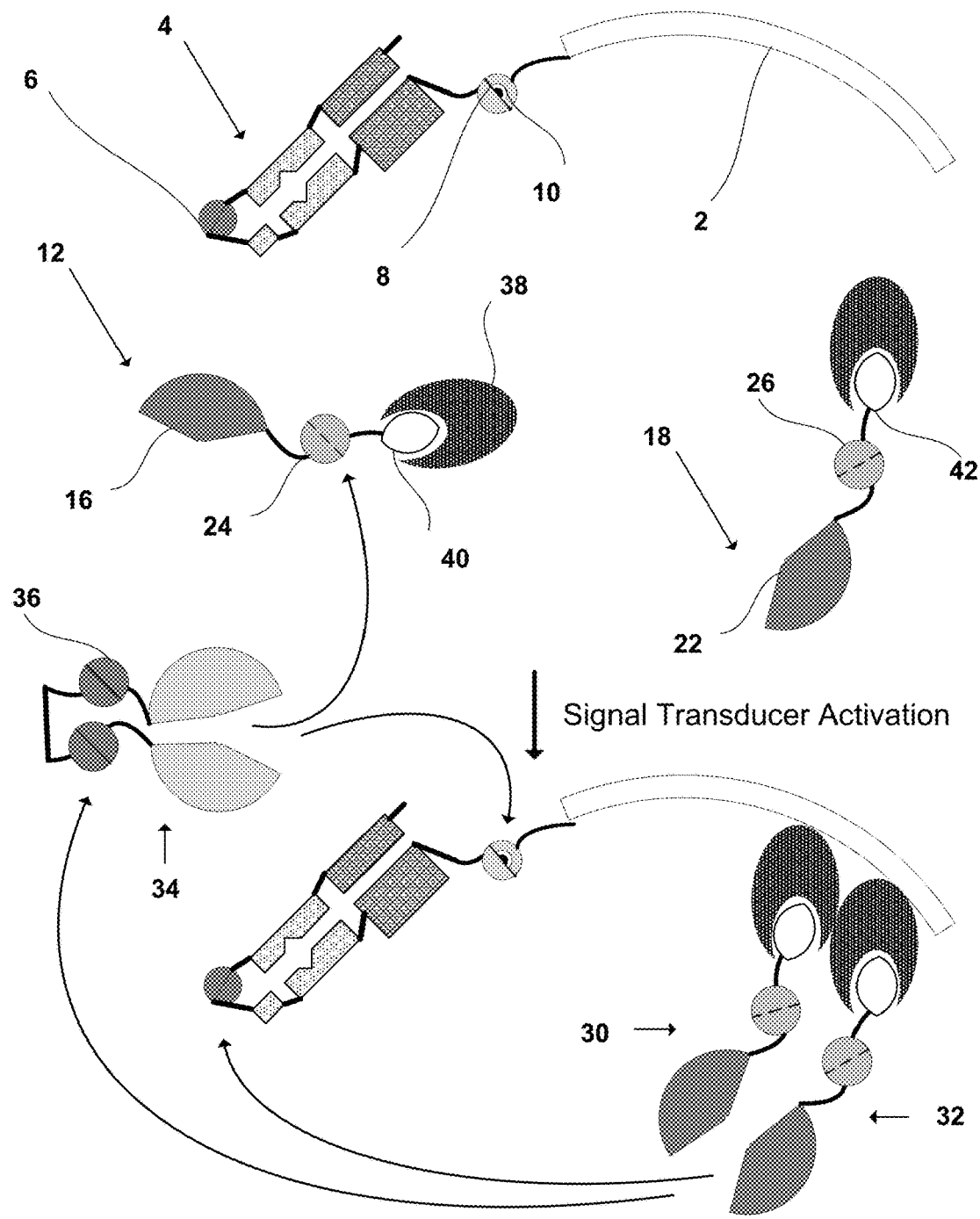

In some embodiments, the synthetic protein circuit has the configuration depicted in FIG. 1B. In some embodiments, a first signal transducer binding domain 40 and a second signal transducer binding domain 42 constitutively bind to signal transducer 38. In some such embodiments, a signal transducer 38 is not localized at the association location 2 when in an inactive state. The signal transducer 38 can localize to the association location 2 when in an active state, thereby bringing the first signal transducer-bound polypeptide 30 and a second signal transducer-bound polypeptide 32 in close proximity at the association location 2 to constitute a first protease as described above.

Figure 1C:
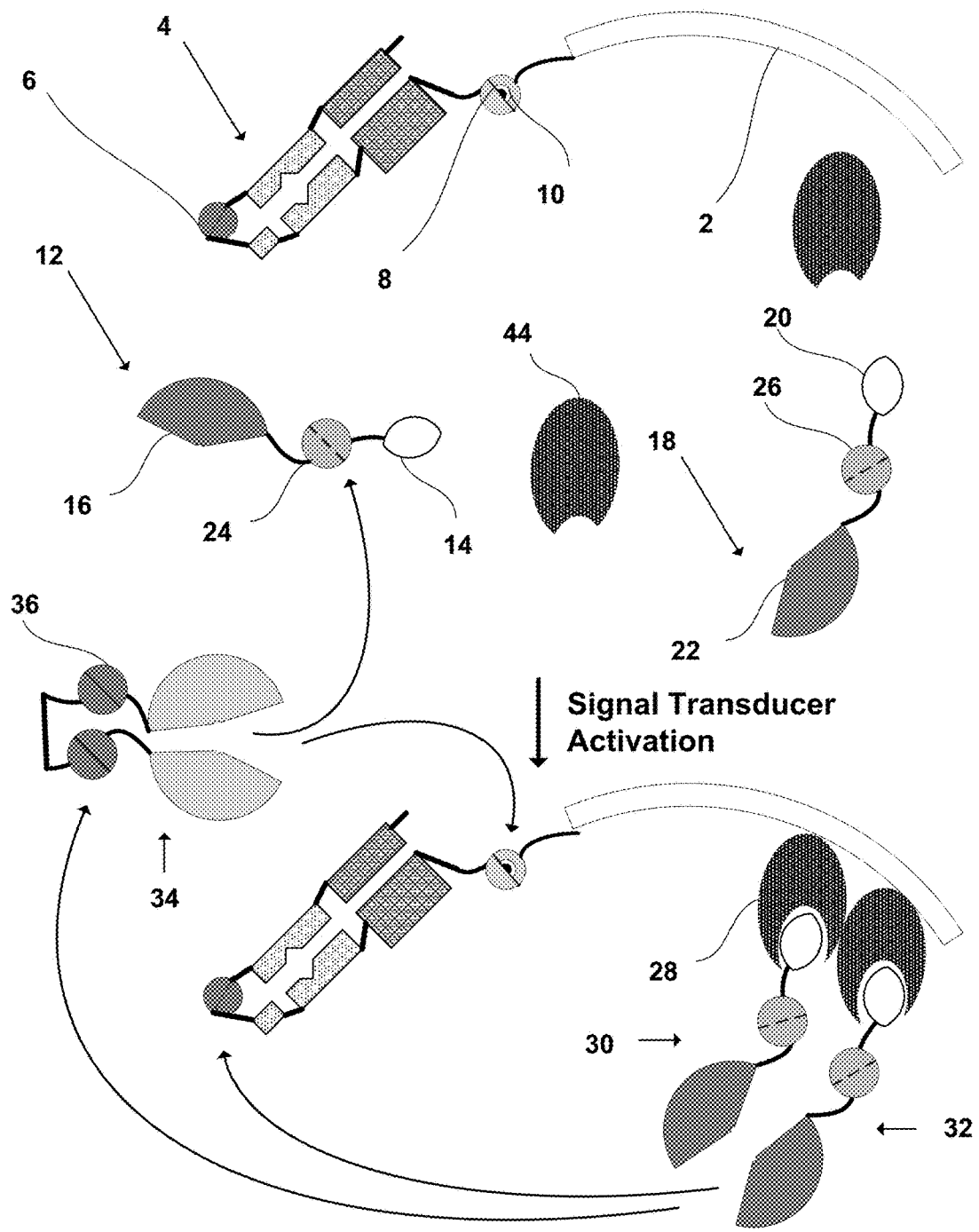

In some embodiments, the synthetic protein circuit has the configuration depicted in FIG. 1C. A signal transducer 44 is not localized at an association location 2 when in an inactive state. Activation of the signal transducer (e.g., Ras) can cause the signal transducer to adopt an active conformation 28 recognized by first signal transducer binding domain 14 and second signal transducer binding domain 20 resulting in the formation of a first signal transducer-bound polypeptide 30 and a second signal transducer-bound polypeptide 32. Additionally, activation of the signal transducer 44 can cause it to localize to association location 2, thereby recruiting the first signal transducer-bound polypeptide 30 and the second signal transducer-bound polypeptide 32 to the association location 2 in close proximity to constitute a first protease as described above.

There are provided, in some embodiments, protein circuits. In some embodiments, the synthetic protein circuit comprises: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting. In some embodiments, one or more of the synthetic protein circuits described herein is a compound protease. In some embodiments, one or more of the first protease, effector protein, and/or repressor protease is a compound protease. The first protease, second protease, and/or third protease can comprise a compound protease. The synthetic protein circuit can comprise any additional compound proteases as described herein. In some embodiments, the effector protein comprises a target protein.

The first signal transducer binding domain of the first polypeptide and the second signal transducer binding domain of the second polypeptide can be identical. In some embodiments, the first signal transducer binding domain of the first polypeptide and the second signal transducer binding domain of the second polypeptide are identical. The first transducer and the second transducer can be identical. In some embodiments, the first transducer and the second transducer are identical.

The first signal transducer, the second signal transducer, or both, can be capable of being localized at the association location. In some embodiments, the first signal transducer, the second signal transducer, or both, are localized at the association location. The first signal transducer when in a first signal transducer active state, the second signal transducer when in a second signal transducer active state, or both, can be capable of being localized at the association location. In some embodiments, the first signal transducer when in a first signal transducer active state, the second signal transducer when in a second signal transducer active state, or both, are localized at the association location. The first signal transducer when in a first inactive state, the second signal transducer when in a second inactive state, or both, can be capable of being localized at the association location. In some embodiments, the first signal transducer when in a first inactive state, the second signal transducer when in a second inactive state, or both, localizes at the association location. The first signal transducer binding domain of the first polypeptide can be capable of binding to the first signal transducer, wherein the second signal transducer binding domain of the second polypeptide can be capable of binding to the second signal transducer, or both. In some embodiments, the first signal transducer binding domain of the first polypeptide binds to the first signal transducer, wherein the second signal transducer binding domain of the second polypeptide binds to the second signal transducer, or both.

The first signal transducer binding domain of the first polypeptide can be capable of binding to the first signal transducer in a first signal transducer active state, wherein the second signal transducer binding domain of the second polypeptide can be capable of binding to the second signal transducer in a second signal transducer active state, or both. In some embodiments, the first signal transducer binding domain of the first polypeptide binds to the first signal transducer in a first signal transducer active state, wherein the second signal transducer binding domain of the second polypeptide binds to the second signal transducer in a second signal transducer active state, or both. The first signal transducer binding domain of the first polypeptide can be capable of binding to the first signal transducer in a first inactive state, wherein the second signal transducer binding domain of the second polypeptide can be capable of binding to the second signal transducer in a second inactive state, or both. In some embodiments, the first signal transducer binding domain of the first polypeptide binds to the first signal transducer in a first inactive state, wherein the second signal transducer binding domain of the second polypeptide binds to the second signal transducer in a second inactive state, or both.

The signal transducer binding domain of the first polypeptide can be capable of binding the first signal transducer to form the first signal transducer-bound polypeptide at the association location, wherein the signal transducer binding domain of the first polypeptide can be capable of binding the first signal transducer to form the first signal transducer-bound polypeptide at the association location, or both. In some embodiments, the signal transducer binding domain of the first polypeptide binds the first signal transducer to form the first signal transducer-bound polypeptide at the association location, wherein the signal transducer binding domain of the first polypeptide binds the first signal transducer to form the first signal transducer-bound polypeptide at the association location, or both.

The signal transducer binding domain of the first polypeptide can be capable of binding the first signal transducer to form the first signal transducer-bound polypeptide at a first cellular location other than the association location, wherein the signal transducer binding domain of the first polypeptide can be capable of binding the first signal transducer to form the first signal transducer-bound polypeptide at a second cellular location other than the association location, or both. In some embodiments, the signal transducer binding domain of the first polypeptide binds the first signal transducer to form the first signal transducer-bound polypeptide at a first cellular location other than the association location, wherein the signal transducer binding domain of the first polypeptide binds the first signal transducer to form the first signal transducer-bound polypeptide at a second cellular location other than the association location, or both.

The first cellular location, the second cellular location, or both can comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof. The association location can comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

A first concentration of the first signal transducer-bound polypeptide can be at least two-fold higher at the association location as compared a first cellular location other than the association location when the first signal transducer is a first signal transducer active state. A first concentration of the first signal transducer-bound polypeptide can be at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 200%, 300%, 400%, or higher and overlapping ranges therein) higher at the association location as compared a first cellular location other than the association location when the first signal transducer is a first signal transducer active state.

A second concentration of the second signal transducer-bound polypeptide can be at least two-fold higher at the association location as compared a second cellular location other than the association location when the second signal transducer is a second signal transducer active state. A second concentration of the second signal transducer-bound polypeptide can be at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 200%, 300%, 400%, or higher and overlapping ranges therein) higher at the association location as compared a second cellular location other than the association location when the second signal transducer is a second signal transducer active state.

A first concentration of the first protease in the first protease active state can be at least two-fold higher at the association location as compared a cellular location other than the association location when the first signal transducer is in a first signal transducer active state and/or when the second signal transducer is in a second signal transducer active state. A first concentration of the first protease in the first protease active state can be at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 200%, 300%, 400%, or higher and overlapping ranges therein) higher at the association location as compared a cellular location other than the association location when the first signal transducer is in a first signal transducer active state and/or when the second signal transducer is in a second signal transducer active state.

In some embodiments, the first part of the first protease domain and the second part of the first protease domain have the weak association affinity when the first signal transducer is in a first signal transducer inactive state and/or the second signal transducer inactive state. The first part of the first protease domain and the second part of the first protease domain can be incapable of associating to form the first protease in the first protease active state when the first signal transducer is in a first signal transducer inactive state and/or the second signal transducer is in a second signal transducer inactive state. In some embodiments, a first concentration of the first signal transducer-bound polypeptide and a second concentration of the second signal transducer-bound polypeptide at the association location can be insufficient for the first part of the first protease domain and the second part of the first protease domain to form an active first protease when the first signal transducer is in a first signal transducer inactive state and/or the second signal transducer is in a second signal transducer inactive state.

A first concentration of the first signal transducer-bound polypeptide at the association location can be comparable to a first cellular location other than the association location when the first signal transducer is in a first signal transducer inactive state. A second concentration of the second signal transducer-bound polypeptide at the association location can be comparable to a second cellular location other than the association location when the second signal transducer is in a second signal transducer inactive state. The first part of the first protease domain and the second part of the first protease domain can be capable of associating with each other to form the first protease in the first protease active state at a threshold first polypeptide concentration and a threshold second polypeptide concentration at the association location. In some embodiments, the first part of the first protease domain and the second part of the first protease domain associate with each other to form the first protease in the first protease active state at a threshold first polypeptide concentration and a threshold second polypeptide concentration at the association location. In some embodiments, the threshold first polypeptide concentration and the threshold second polypeptide concentration at the association location is reached at a threshold signal transducer activation level of the signal transducer.

Effector Proteins and Repressor Proteins

In some embodiments, the effector protein changes from an effector inactive state to an effector active state when the first protease in the first protease active state cuts the first cut site of the effector. In some embodiments, a level of activation of the effector protein positively correlates with a first level of activation of the first signal transducer and/or a second level of activation of the second signal transducer. In some embodiments, the level of activation of the effector protein is related to a number of molecules of the effector protein in an effector active state, wherein the first level of activation of the first signal transducer is related to a number of molecules of the first signal transducer in a first transducer active state. The second level of activation of the second signal transducer can be related to a number of molecules of the second signal transducer in a second transducer active state. In some embodiments, the effector protein changes from an effector active state to an effector inactive state when the first protease in the first protease active state cuts the first cut site of the effector. In some embodiments, a level of activation of the effector protein negatively correlates with a first level of activation of the first signal transducer and/or a second level of activation of the second signal transducer. In some embodiments, the level of activation of the effector protein can be related to a number of molecules of the effector protein in an effector active state. The first level of activation of the first signal transducer can be related to a number of molecules of the first signal transducer in a first transducer active state. The second level of activation of the second signal transducer can be related to a number of molecules of the second signal transducer in a second transducer active state. The effector protein can comprise a third signal transducer binding domain, and wherein the third signal transducer binding domain is capable of binding the first signal transducer and/or the second signal transducer. In some embodiments, the effector protein comprises a protease, a reporter protein, a fluorescent protein, a scaffold, an actuator protein, a transcriptional regulator, or a signaling protein.

In some embodiments, the synthetic protein circuit comprises a repressor protein. The repressor protein can comprise a second protease. In some embodiments, the second protease in a second protease active state can be capable of cutting a first cut site of the first polypeptide and/or a second cut site of the second polypeptide. In some embodiments, the second protease in a second protease active state cuts a first cut site of the first polypeptide and/or a second cut site of the second polypeptide. The first polypeptide can be changed into a first polypeptide destabilized state, a first polypeptide delocalized state, and/or a first polypeptide inactivate state after the second protease in the second protease active state cuts the first cut site of the first polypeptide. The second polypeptide can be changed into a second polypeptide destabilized state, a second polypeptide delocalized state, and/or a second polypeptide inactivate state after the second protease in the second protease active state cuts the second cut site of the second polypeptide. In some embodiments, the first polypeptide is changed into a first polypeptide destabilized state, a first polypeptide delocalized state, and/or a first polypeptide inactivate state after the second protease in the second protease active state cuts the first cut site of the first polypeptide. The second polypeptide can be changed into a second polypeptide destabilized state, a second polypeptide delocalized state, and/or a second polypeptide inactivate state after the second protease in the second protease active state cuts the second cut site of the second polypeptide. In some embodiments the synthetic protein circuit comprises a tuner as described herein. The location, stability, and/or activity of a repressor protein can be regulated by a tuner as described herein.

The repressor protein can comprise a cut site the first protease in the first protease active state is capable of cutting. The repressor protein can be changed into a repressor destabilized state, a repressor delocalized state, and/or a repressor inactivate state after the first protease cuts the cut site of the repressor protein. In some embodiments, the repressor protein is changed into a repressor destabilized state, a repressor delocalized state, and/or a repressor inactivate state after the first protease cuts the cut site of the repressor protein.

The effector protein can comprise a second cut site the second protease in the second protease active state is capable of cutting. In some embodiments, the effector protein can be changed into a first effector destabilized state, a first effector delocalized state, and/or a first effector inactivate state after the second protease in the second protease active state cuts the cut site of the effector protein. The effector protein can comprise a degron. The second protease in the second protease active state can be capable of cutting the second cut site of the effector protein to expose the degron. The degron of the effector protein being exposed can change the effector protein to an effector destabilized state. The first polypeptide can be changed into a first polypeptide stabilized state, a first polypeptide localized state, and/or a first polypeptide activate state after the second protease in the second protease active state cuts the first cut site of the first polypeptide. The second polypeptide can be changed into a second polypeptide stabilized state, a second polypeptide localized state, and/or a second polypeptide activate state after the second protease in the second protease active state cuts the second cut site of the second polypeptide. There are provided, in some embodiments, degrons. A degron can comprise DHFR degron, an N-degron, a phospho degron, a heat inducible degron, a photosensitive degron, an oxygen dependent degron, ornithine decarboxylase degron, estrogen receptor domain degrons, an ecDHFR degron, an FKBP degron, a UnaG degron, or any combination thereof. As a non-limiting example, the degron may be an ornithine decarboxylase degron. The degron can comprise an ecDHFR degron.

The repressor protein can comprise a cut site the first protease in the first protease active state is capable of cutting. The repressor protein can be changed into a repressor stabilized state, a repressor localized state, and/or a repressor activate state after the first protease in the first protease active state cuts the first cut site of the repressor protein. The effector protein can comprise a second cut site the second protease in the second protease active state is capable of cutting. The effector protein can be changed into a first effector stabilized state, a first effector localized state, and/or a first effector activate state after the second protease in the second protease active state cuts the second cut site of the effector protein. The effector protein can comprise a degron. The second protease in the second protease active state can be capable of cutting the second cut site of the effector protein to hide the degron. The degron of the effector protein being hidden can change the effector protein to an effector stabilized state.

The effector protein can be capable of changing a synthetic protein circuit component of the synthetic protein circuit to a synthetic protein circuit component active state. In some embodiments, the effector protein can comprise a third protease domain. The third protease domain can change to an effector inactive state after the second protease in the second protease active state cuts the cute site of the effector protein.

The effector protein can comprise a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector. The effector protein in an effector active state can be capable of activating or inactivating an endogenous signal transduction pathway. In some embodiments, the effector protein in an effector active state activates or inactivates an endogenous signal transduction pathway. The effector protein can comprise Caspase-3, Caspase 7, Caspase-9, Caspase-8, Bax, Bid, Bad, Bak, BCL2L11, p53, PUMA, Diablo/SMAC, S-TRAIL, or any combination thereof. The effector protein in an effector active state can be capable of rendering a resident cell sensitive to a prodrug. In some embodiments, the effector protein comprises cytosine deaminase and uracil phosphoribosyl transferase, and the prodrug is 5-fluorocytosine (5-FC). In some embodiments, the effector protein comprises thymidine kinase (TK), and the prodrug comprises ganciclovir.

Signal Transducers

A variety of signal transducers are contemplated herein. The first signal transducer can be capable of binding the first signal transducer binding domain and/or the second signal transducer can be capable of binding the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof. The first signal transducer, the second signal transducer, or both can be endogenous proteins. The first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof.

The first signal transducer and/or the second signal transducer can be capable of regulating cell survival, cell growth, cell proliferation, cell adhesion, cell migration, cell metabolism, cell morphology, cell differentiation, apoptosis, or any combination thereof. The first signal transducer, the second signal transducer, or both can comprise a RAS protein (e.g., KRAS, NRHAS, HRAS). The first signal transducer, the second signal transducer, or both can be exogenous proteins. In some embodiments, the synthetic protein circuit comprises the first signal transducer, the second signal transducer, or both. In some embodiments, the first signal transducer, the second signal transducer, or both comprise a lipid (e.g., a phospholipid, phosphatidylinositol 3-phosphate).

Signal transducers can be can be associated with one or more diseases or disorders. In some embodiments, a disease or disorder is characterized by an aberrant signaling of one or more signal transducers disclosed herein. In some embodiments, the activation level of the signal transducer correlates with the occurrence and/or progression of a disease or disorder. The activation level of the signal transducer can be directly responsible or indirectly responsible for the etiology of the disease or disorder. Non-limiting examples of signal transducers, signal transduction pathways, and diseases and disorders characterized by aberrant signaling of said signal transducers are listed in Tables 1-3.

TABLE 1

DISEASES AND DISORDERS OF INTEREST

| Diseases/Disorders | Genes |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion - related disorders | Prp |

TABLE 1-continued

DISEASES AND DISORDERS OF INTEREST

| Diseases/Disorders | Genes |
| --- | --- |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 2

SIGNAL TRANSDUCERS

| | |
| --- | --- |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, |

TABLE 2-continued

| SIGNAL TRANSDUCERS | |
|---|---|
| | CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 3

| SIGNAL TRANSDUCTION PATHWAYS | |
|---|---|
| Pathway | Gene(s) |
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; |

TABLE 3-continued

SIGNAL TRANSDUCTION PATHWAYS

| Pathway | Gene(s) |
|---|---|
| | PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; |

TABLE 3-continued

SIGNAL TRANSDUCTION PATHWAYS

| Pathway | Gene(s) |
|---|---|
| | BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; |

TABLE 3-continued

SIGNAL TRANSDUCTION PATHWAYS

| Pathway | Gene(s) |
|---|---|
| | TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; |

TABLE 3-continued

SIGNAL TRANSDUCTION PATHWAYS

| Pathway | Gene(s) |
|---|---|
| | PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |

TABLE 3-continued

| SIGNAL TRANSDUCTION PATHWAYS | |
|---|---|
| Pathway | Gene(s) |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |

TABLE 3-continued

| SIGNAL TRANSDUCTION PATHWAYS | |
|---|---|
| Pathway | Gene(s) |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |

TABLE 3-continued

SIGNAL TRANSDUCTION PATHWAYS

| Pathway | Gene(s) |
|---|---|
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln |

Signal Transducer Binding Domains

There are provided, in some embodiments, first signal transducer binding domains, second signal transducer binding domains, and/or third signal transducer binding domains. Two or more of the first signal transducer binding domain, the second signal transducer binding domain, and/or third signal transducer binding domain can be identical. Two or more of the first signal transducer binding domain, the second signal transducer binding domain, and/or third signal transducer binding domain can be different. The first signal transducer binding domain, the second signal transducer binding domain, and/or third signal transducer binding domain each can be capable of binding molecules of the first signal transducer and/or the second signal transducer. The third signal transducer binding domain can be capable of binding to a third signal transducer at the association location. In some embodiments, the first signal transducer, the second signal transducer, and/or the third signal transducer belong to a signal transduction pathway.

The first signal transducer binding domain, the second signal transducer binding domain, and/or the third signal transducer binding domain can comprise a RAS binding domain (RBD) and/or RAS association domain (RAD). In some embodiments, the first signal transducer binding domain, the second signal transducer binding domain, and/or the third signal transducer binding domain comprises a lipid binding domain (e.g., a Pleckstrin homology (PH) domain). The first signal transducer binding domain, the second signal transducer binding domain, and/or the third signal transducer binding domain can comprise a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

There are provided, in some embodiments, antigen-binding moieties (e.g., monobodies). In some embodiments, first signal transducer binding domain, the second signal transducer binding domain, and/or third signal transducer binding domain comprise an antigen binding moiety. The antigen-binding moiety can be configured to bind any of the signal transducers contemplated herein, such as those listed in Tables 1-3. The antigen-binding moiety can be configured to bind a signal transducer in an active and/or inactive state as described herein.

Antigen-binding moieties can comprise antibodies, antibody fragments, and variants. In some embodiments, antibody fragments and variants may comprise antigen binding regions from intact antibodies. Examples of antibody fragments and variants may include, but are not limited to Fab, Fab', F(ab')2, and Fv fragments; diabodies; linear antibodies; single-chain antibody molecules such as single chain variable fragment (scFv); and multi specific antibodies formed from antibody fragments.

For the purposes herein, an "antibody" may comprise a heavy and light variable domain as well as an Fc region. As used herein, the term "native antibody" usually refers to a heterotetrameric glycoprotein of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VT) followed by a number of constant domains. Each light chain has a variable domain at one end (VL) and a constant domain at its other end: the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains comprise hypervariable regions. As used herein, the term "hypervariable region" refers to a region within a variable domain comprising amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody comprising a structure that is complimentary to its target antigen or epitope. Other portions of the variable domain, not interacting with the antigen, are referred to as framework (FVV) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments based on comparisons with other antibodies can also be used. Determining residues that make up CDRs may include the use of numbering schemes including, but not limited to, those taught by Kabai, Chothia, and Honegger.

H and VL domains have three CDRs each. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs has favored canonical structures with the exception of the CDR-H3, which comprises amino acid sequences that may be highly variable in sequence and length between antibodies resulting in a variety of three-dimensional structures in antigen-binding domains. In some cases, CDR-H3s may be analyzed among a panel of related antibodies to assess antibody diversity. Various methods of determining CDR sequences are known in the art and may be applied to known antibody sequences.

As used herein, the term "Fv" refers to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain (to form a single chain Fv (scFv)) or through the introduction of a disulfide bridge between heavy and light chain variable domains.

As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. Using molecular genetics, two scFvs can be engineered in tandem into a single polypeptide, separated by a linker domain, called a "tandem scFv" (tascFv). Construction of a tascFv with genes for two different scFvs yields a "bispecific single-chain variable fragments" (bis-scFvs).

As used herein, the term "bispecific antibody" refers to an antibody capable of binding two different antigens. Such antibodies typically comprise regions from at least two different antibodies. As used herein, the term "diabody" refers to a small antibody fragment with two antigen-binding sites. Diabodies are functional bispecific single-chain antibodies (bscAb). Diabodies comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites.

The term "intrabody" can refer to a form of antibody that is not secreted from a cell in which it is produced, but instead targets one or more intracellular proteins. Intrabodies may be used to affect a multitude of cellular processes including, but not limited to intracellular trafficking, transcription, translation, metabolic processes, proliferative signaling and cell division. In some embodiments, methods provided herein may include intrabody-based therapies. In some such embodiments, variable domain sequences and/or CDR sequences disclosed herein may be incorporated into one or more constructs for intrabody-based therapy.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen.

The modifier "monoclonal" can indicate the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source(s) with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity. In one embodiment, the antibody may be a humanized full-length antibody.

As used herein, the term "antibody variant" refers to a modified antibody (in relation to a native or starting antibody) or a biomolecule resembling a native or starting antibody in structure and/or function (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, IgG 1, IgG2, IgG3, IgG4, or IgM), humanized variants, optimized variants, multi-specific antibody variants (e.g., bispecific variants), and antibody fragments.

In some embodiments, the antigen-binding moieties provided herein comprise antibody mimetics (e.g., monobodies). As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (e.g., the protein scaffolds disclosed in U.S. Pat. Nos. 6,673,901 and 6,348,584). In some embodiments, antibody mimetics may be those known in the art including, but are not limited to affibody molecules, affitins, anticalins, avimers, Centyrins, DARPINS™, Fynomers and Kunitz and domain peptides. In other embodiments, antibody mimetics may include one or more non-peptide regions.

In some embodiments, the antigen-binding moieties provided herein comprise multispecific antibodies that bind more than one epitope. As used herein, the terms "multibody" or "multispecific antibody" refer to an antibody wherein two or more variable regions bind to different epitopes. The epitopes may be on the same or different targets. In some embodiments, a multi-specific antibody is a "bispecific antibody" which recognizes two different epitopes on the same or different antigens. In one aspect, bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

In some embodiments, the antigen-binding moieties provided herein comprise antibodies comprising a single antigen-binding domain (e.g., nanobodies). These molecules are extremely small, with molecular weights approximately one-tenth of those observed for full-sized mAbs. Further antibodies may include "nanobodies" derived from the antigen-binding variable heavy chain regions (VHHs) of heavy chain antibodies found m camels and llamas, which lack light chains (Nelson, A. L., MAbs. 2010. January-February; 2(1):77-83).

In some embodiments, the antibody may be "miniaturized". Among the best examples of mAb miniaturization are the small modular immunopharmaceuticals (SMIPs) from Trubion Pharmaceuticals. These molecules, which can be monovalent or bivalent, are recombinant single-chain molecules containing one VL, one VH antigen-binding domain, and one or two constant "effector" domains, all connected by linker domains. One example of miniaturized antibodies is called "unibody" in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo.

In some embodiments, the antigen-binding moieties provided herein comprise single-domain antibodies (sdAbs, or nanobodies) which are antibody fragment consisting of a single monomelic variable antibody domain. In some embodiments, it is able to bind selectively to a specific antigen (e.g., like a whole antibody). In one aspect, a sdAb may be a "Camel Ig or "camelid VHH". As used herein, the term "camel Ig" refers to the smallest known antigen-binding unit of a heavy chain antibody (Koch-No Ite, et al, FASEB J., 2007, 21: 3490-3498). A "heavy chain antibody" or a "camelid antibody" refers to an antibody that contains two VH domains and no light chains (Riechmann L. et al, J. Immunol. Methods, 1999, 231: 25-38; international patent publication NOs. WO 1994/004678 and WO 1994/025591; and U.S. Pat. No. 6,005,079). In another aspect, a sdAb may be a "immunoglobulin new antigen receptor" (IgNAR). As used herein, the term "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulfide bridges, and patterns of intra-loop hydrogen bonds.

In some embodiments, the antigen-binding moieties provided herein comprise intrabodies. Intrabodies are a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. Sequences from donor antibodies may be used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form, a single chain antibody comprising the variable domains of the heavy and light chains joined by a flexible linker polypeptide, intrabodies typically lack disulfide bonds and are capable of modulating the expression or activity of target genes through their specific binding activity. Single chain intrabodies are often expressed from a recombinant nucleic acid molecule and engineered to be retained intracellularly (e.g., retained in the cytoplasm, endoplasmic reticulum, or periplasm).

Detection of Signal Transducer Activity

The synthetic protein circuit can be capable of detecting an activity of the first signal transducer and an activity of the second signal transducer. In some embodiments, an activity of the effector protein correlates with an activity of the first signal transducer and/or an activity of the second signal transducer. The synthetic protein circuit can be capable of detecting activities of the first signal transducer and activities of the second signal transducer over a period of time. In some embodiments, activities of the effector protein correlate with activities of the first signal transducer and activities of the second signal transducer over a period of time.

The synthetic protein circuit can be capable of detecting an aberrant signaling. In some embodiments, the synthetic protein circuit detects an aberrant signaling or one or more signal transducers. Aberrant signaling can comprise an active signal transducer, an overactive signal transducer, a constitutively active signal transducer over a period of time, or any combination thereof. The synthetic protein circuit can be capable of detecting an activity of a signal transducer activator and/or an activity of a signal transducer repressor. The effector protein can be capable of detecting an activity of a signal transducer activator and/or an activity of a signal transducer repressor. In some embodiments, the synthetic protein circuit detects an activity of a signal transducer activator and/or an activity of a signal transducer repressor. In some embodiments, the effector protein detects an activity of a signal transducer activator and/or an activity of a signal transducer repressor.

In some embodiments, aberrant signaling refers to a measurable or observable change in the level of activity of a signal transducer which is associated with a disease or disorder (e.g., with susceptibility, onset, or progression of a cancer). Aberrant signaling can comprise any level of activity that is statistically significant different from the expected (e.g., normal or baseline) level of activity of the signal transducer. Aberrant signaling can comprise a level of activity of a signal transducer that is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) increased or decreased as compared to a normal tissue sample and/or prior tissue sample. Aberrant signaling can comprise a level of activity of a signal transducer that is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) increased or decreased an analogous sample from a portion of a subject not having a disorder or disorder characterized by aberrant signaling. Aberrant signaling can comprise a level of activity of a signal transducer that is at least 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) increased or decreased as compared a control. Aberrant signaling can comprise a change in signaling activity as compared a control. As used herein the term "control" can refer to predetermined values, and also refers to samples of materials tested in parallel with the experimental materials. Examples include samples from control populations, biopsy samples taken from tissue adjacent to a biopsy sample suspected of being in a disease state (e.g., cancerous) and control samples generated through manufacture to be tested in parallel with the experimental samples. As used herein the term "control" includes positive and negative controls which may be a predetermined value that can take a variety of forms. The control(s) can be a single cut-off value, such as a median or mean, or can be established based upon comparative groups, such as in groups having a normal level of activity of the signal transducer and groups having an abnormal level of activity of the signal transducer. Another example of a comparative group is a group having a particular disease or disorder characterized by an aberrant signaling of the signal transducer, and a group without the disease or disorder characterized by an aberrant signaling of the signal transducer. The predetermined value of a control will depend upon the particular population selected. For example, an apparently healthy population will have a different level of activity of a given signal transducer than will a population which is known to have a particular disease or disorder characterized by an aberrant signaling of the signal transducer. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. As used herein, the term "aberrant signaling" can include a higher or lower level of activity of a signal transducer relative to a selected control.

In some embodiments, the synthetic protein circuit comprises one or more circuit components that can be capable of increasing a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor.

In some embodiments, the synthetic protein circuit comprises one or more circuit components that can be capable of increasing a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

Aberrant signaling can comprise an active signal transducer repressor and an active signal transducer. Aberrant signaling can comprise an inactive signal transducer activator and an active signal transducer. Aberrant signaling can comprise an inactive signal transducer. Aberrant signaling can comprise an underactive signal transducer. Aberrant signaling can comprise a constitutively inactive signal transducer over a period of time. Aberrant signaling can comprise an inactive signal transducer repressor and an inactive signal transducer. Aberrant signaling can comprise an active signal transducer activator and an inactive signal transducer. Aberrant signaling can comprise an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

The synthetic protein circuit can be capable of directly or indirectly inducing cell death in the presence of the aberrant signaling. In some embodiments, the effector protein directly or indirectly induces cell death in the presence of aberrant signaling. In some embodiments, the synthetic protein circuit directly or indirectly induces cell death when a first level of activation of the first signal transducer is above a first signal transducer activation threshold and/or a second level of activation of the second signal transducer is below a second signal transducer activation threshold. In some embodiments, the effector protein directly or indirectly induces cell death when a first level of activation of the first signal transducer is above a first signal transducer activation threshold and/or a second level of activation of the second signal transducer is below a second signal transducer activation threshold.

Agents of Interest

In some embodiments, the effector protein is an agent of interest. In some embodiments, a molecule other than the effector protein is an agent of interest. In some embodiments, the agent of interest is an endogenous agent of interest. The agent of interest can be situated in the same pathway as the signal transducer. The agent of interest can be an inducer of cell death. The agent of interest can be induce cell death by a non-endogenous cell death pathway (e.g., a bacterial pore-forming toxin). In some embodiments, the agent of interest can be a pro-survival protein. In some embodiments, the agent of interest is a modulator of the immune system. The agent of interest can activate an adaptive immune response, and innate immune response, or both. The agent of interest can be an exogenous agent of interest (e.g., the product of a transgene). In some embodiments, the expression, stability, and/or activity of the agent of interest (e.g., a transgene product) is under the control of the effector protein. For example, the localization, stability, expression, and/or activity of the agent of interest can be related to a number of molecules of the effector protein in an effector active state.

In some embodiments, the agent of interest ameliorates a disease or disorder characterized by an aberrant signaling of one or more signaling transducers. In some embodiments, the agent of interest diminishes the activation level of one or more signal transducers (e.g., signal transducers with aberrant overactive signaling, signal transducers listed in Tables 1-3). In some embodiments, the agent of interest increases the activation level of one or more signal transducers (e.g., signal transducers with aberrant underactive signaling). In some such embodiments, the agent of interest can modulate the abundance, location, stability, and/or activity of activators or repressors of said signal transducers.

In some embodiments, the agent of interest is encoded by a transgene. In some embodiments, the effector protein in an effector active state induces expression of a transgene. In some such embodiments, the expression, stability, and or activity of the transgene product regulated by the one or more synthetic protein circuit components. For example, in some embodiments, the agent of interest can comprise one or more of a degron or protease cut site as provided herein. As disclosed herein, the transgene is operatively linked with appropriate regulatory elements in some embodiments. The one or more transgenes can comprise a siRNA, a shRNA, an antisense RNA oligonucleotide, an antisense miRNA, a trans-splicing RNA, a guide RNA, single-guide RNA, crRNA, a tracrRNA, a trans-splicing RNA, a pre-mRNA, a mRNA, or any combination thereof. The one or more transgenes can comprise cytosine deaminase, thymidine kinase, Bax, Bid, Bad, Bak, BCL2L11, p53, PUMA, Diablo/SMAC, S-TRAIL, Cas9, Cas9n, hSpCas9, hSpCas9n, HSVtk, cholera toxin, diphtheria toxin, alpha toxin, anthrax toxin, exotoxin, pertussis toxin, Shiga toxin, shiga-like toxin Fas, TNF, caspase 2, caspase 3, caspase 6, caspase 7, caspase 8, caspase 9, caspase 10, caspase 11, caspase 12, purine nucleoside phosphorylase, or any combination thereof.

In some embodiments, the agent of interest is a protein of interest. As used herein, a "protein of interest" can be any protein, including naturally-occurring and non-naturally occurring proteins. Examples of protein of interest include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof; and interferons and variants thereof.

In some embodiments, the agent of interest is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as— glucosidase, imiglucarase, β-glucocerebrosidase, and alglucerase; enzyme activators, such as tissue plasminogen activator; chemokines, such as IP-10, monokine induced by interferon-gamma (Mig), Gro/IL-8, RANTES, MIP-1, MIP-I β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or mini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the agent of interest comprises an active fragment of a protein, such as any of the aforementioned proteins. In some embodiments, the protein of interest is a fusion protein comprising some or all of two or more proteins. In some embodiments a fusion protein can comprise all or a portion of any of the aforementioned proteins.

In some embodiments, the agent of interest comprises a multi-subunit protein. For examples, the agent of interest can comprise two or more subunits, or two or more independent polypeptide chains. In some embodiments, the agent of interest can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody. In some embodiments, the protein of interest can be an antigen-binding moiety as disclosed herein.

In some embodiments, the agent of interest comprises a pro-survival protein (e.g., Bcl-2, Bcl-XL, Mcl-1 and A1). In some embodiments, the agent of interest is a apoptotic factor or apoptosis-related protein such as, for example, AIF, Apaf e.g. Apaf-1, Apaf-2, Apaf-3, oder APO-2 (L), APO-3 (L), Apopain, Bad, Bak, Bax, Bcl-2, Bcl-$x_L$, Bcl-$x_S$, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-PKcs, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, and/or transglutaminase.

In some embodiments, the agent of interest comprises a cellular reprogramming factor capable of converting an at least partially differentiated cell to a less differentiated cell, such as, for example, Oct-3, Oct-4, Sox2, c-Myc, Klf4, Nanog, Lin28, ASCL1, MYT1 L, TBX3b, SV40 large T, hTERT, miR-291, miR-294, miR-295, or any combinations thereof. In some embodiments, the agent of interest comprises a programming factor that is capable of differentiating a given cell into a desired differentiated state, such as, for example, nerve growth factor (NGF), fibroblast growth factor (FGF), interleukin-6 (IL-6), bone morphogenic protein (BMP), neurogenin3 (Ngn3), pancreatic and duodenal homeobox 1 (Pdx1), Mafa, or any combination thereof.

In some embodiments, the agent of interest comprises a human adjuvant protein capable of eliciting an innate immune response, such as, for example, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4 bp, MCP, DAF, H, I, P and CD59; from proteins which are components of the signaling networks of the pattern recognition receptors including TLR and IL-1 R1, whereas the components are ligands of the pattern recognition receptors including IL-1 alpha, IL-1 beta, Beta-defensin, heat shock proteins, such as HSP10, HSP60, HSP65, HSP70, HSP75 and HSP90, gp96, Fibrinogen, Typ111 repeat extra domain A of fibronectin; the receptors, including IL-1 RI, TLR1, TLR2, TLR3, TLR4, TLR5, TLR6, TLR7, TLR8, TLR9, TLR10, TLR11; the signal transducers including components of the Small-GTPases signaling (RhoA, Ras, Rac1, Cdc42 etc.), components of the PIP signaling (PI3K, Src-Kinases, etc.), components of the MyD88-dependent signaling (MyD88, IRAK1, IRAK2, etc.), components of the MyD88-independent signaling (TICAM1, TICAM2 etc.); activated transcription factors including e.g. NF-KB, c-Fos, c-Jun, c-Myc; and induced target genes including IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

In some embodiments, the agent of interest is a protein which, upon administration of a prodrug, effects transition of a gene product to a compound which kills its host cell (e.g., a suicide gene product). Any suitable suicide gene and prodrug is contemplated this disclosure, such as, for example, the suicide gene/prodrug combinations depicted in Table 4.

TABLE 4

SUICIDE GENES AND PRODRUGS

| Suicide Gene | Prodrug(s) |
|---|---|
| HSV thymidine kinase (TK) | Ganciclovir (GCV); Ganciclovir elaidic acid ester; Penciclovir (PCV); Acyclovir (ACV); Valacyclovir (VCV); (E)-5-(2-bromovinyl)-2'-deoxyuridine (BVDU); Zidovuline (AZT); 2'-exo-methanocarbathymidine (MCT) |
| Cytosine Deaminase (CD) | 5-fluorocytosine (5-FC) |
| Purine nucleoside phosphorylase (PNP) | 6-methylpurine deoxyriboside (MEP); fludarabine (FAMP) |
| Cytochrome p450 enzymes (CYP) | Cyclophosphamide (CPA); Ifosfamide (IFO); 4-ipomeanol (4-IM) |
| Carboxypeptidases (CP) | 4-[(2-chloroethyl)(2-mesyloxyethyl)amino]benzoyl-L-glutamic acid (CMDA); Hydroxy-and amino-aniline mustards; Anthracycline glutamates; Methotrexate α-peptides (MTX-Phe) |

TABLE 4-continued

SUICIDE GENES AND PRODRUGS

| Suicide Gene | Prodrug(s) |
| --- | --- |
| Caspase-9 | AP1903 |
| Carboxylesterase (CE) | Irinotecan (IRT); Anthracycline acetals |
| Nitroreductase (NTR) | dinitroaziridinylbenzamide CB1954; dinitrobenzamide mustard SN23862; 4-Nitrobenzyl carbamates; Quinones |
| Horse radish peroxidase (HRP) | Indole-3-acetic acid (IAA); 5-Fluoroindole-3-acetic acid (FIAA) |
| Guanine Ribosyltransferase (XGRTP) | 6-Thioxanthine (6-TX) |
| Glycosidase enzymes | HM1826; Anthracycline acetals |
| Methionine-α,γ-lyase (MET) | Selenomethionine (SeMET) |
| Thymidine phosphorylase (TP) | 5'-Deoxy-5-fluorouridine (5'-DFU) |

Methods of Treatment

Disclosed herein include methods of treating a disease or disorder characterized by an aberrant signaling of one or more signal transducers. In some embodiments, the method comprises: expressing a synthetic protein circuit in a cell of a subject in need thereof, the synthetic protein circuit comprising: a first polypeptide comprising a first signal transducer binding domain and a first part of a first protease domain, wherein the first signal transducer binding domain is capable of binding a first signal transducer of the cell to form a first signal transducer-bound polypeptide; a second polypeptide comprising a second signal transducer binding domain and a second part of the first protease domain, wherein the second signal transducer binding domain is capable of binding a second signal transducer of the cell to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting to change the effector protein to an effector active state, or an effector inactive state, which correlates with an aberrant signaling of the first signal transducer and/or the second signal transducer, and wherein the effector protein in the effector active state, or the effector inactive state, is capable of changing a state of the cell, thereby treating a disease or disorder characterized by the aberrant signaling of the first signal transducer and/or the second signal transducer. Expressing can comprise administering one or more nucleic acids encoding the synthetic protein circuit, such as any of the nucleic acids described herein.

Disclosed herein include embodiments of a method of treating a disease or disorder characterized by an aberrant signaling of one or more signal transducers. In some embodiments, the method comprises: expressing a synthetic protein circuit in a cell of a subject in need thereof. The synthetic protein circuit can comprise: a first polypeptide comprising a first signal transducer binding domain and a first part of a first protease domain, wherein the first signal transducer binding domain binds to a first signal transducer of the cell to form a first signal transducer-bound polypeptide. The synthetic protein circuit can comprise: a second polypeptide comprising a second signal transducer binding domain and a second part of the first protease domain, wherein the second signal transducer binding domain binds to a second signal transducer to form a second signal transducer-bound polypeptide, and wherein the first part of the first protease domain and the second part of the first protease domain associate with each other to constitute a first protease in a first protease active state when the first signal transducer and the second signal transducer are in close proximity at an association location. The synthetic circuit can comprise: an effector protein comprising a first cut site the first protease in the first protease active state cuts to change the effector protein to an effector active state (or an effector inactive state), which correlates with an aberrant signaling of the first signal transducer and/or the second signal transducer. The effector protein in the effector active state (the effector inactive state) can change a state of the cell (e.g., the effector protein can induce apoptosis), thereby treating a disease or disorder characterized by the aberrant signaling of the first signal transducer and/or the second signal transducer.

The disease or disorder can be characterized by an aberrant signaling of the first transducer and an aberrant signaling of the second transducer, and wherein the first transducer and the second transducer can be different. The disease or disorder can be characterized by an aberrant signaling of a RAS protein. The disease or disorder can be a cancer. The disease or disorder can comprise a RASopathy (e.g., Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, Legius syndrome, or any combination thereof). The disease can comprise a neurological disease or a neurodegenerative disease. The disease can comprise an autoimmune disease The disease can comprise infectious disease. In some embodiments, the method comprises administering a prodrug. The prodrug can comprise 5-fluorocytosine (5-FC), ganciclovir, or any of the prodrugs listed in Table 4. The disease or disorder can be characterized by an aberrant signaling of the first transducer, such as those described herein at Tables 1-3. The disease or disorder can be characterized by an aberrant signaling of the first transducer and an aberrant signaling of the second transducer, and wherein the first transducer and the second transducer can be identical. In some embodiments, aberrant signaling of the one or more signal transducers is a direct or indirect cause of the disease or disorder. In some embodiments, aberrant signaling of the one or more signal transducers is a direct or indirect cause of a symptom of the disease or disorder. In some embodiments of the methods provided herein, treatment reduces the aberrant signaling of the one or more signal transducers. In some embodiments of the methods provided herein, treatment reduces the induces the death of cells comprising the aberrant signaling of the one or more signal transducers. In some embodiments of the methods provided herein, treatment reduces the induces or prevents an immune response versus cells comprising the aberrant signaling of the one or more signal transducers. In some embodiments, treatment of the disease or disorder comprises the action of the agent of interest as described herein.

The administering can comprise aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. There are provided, in some embodiments, pharmaceutical composition for administration of any of the compositions provided herein. The pharmaceutical composition can be formulated with a pharmaceutically acceptable carrier or excipient. A pharmaceutically acceptable carrier or excipient refers to a carrier (e.g., carrier, media, diluent, solvent, vehicle, etc.) which does not significantly interfere with the biological activity or effectiveness of the active ingredient(s) of a pharmaceutical composition and which is not excessively toxic to the host at the concentrations at which it is used or administered. Other pharmaceutically acceptable ingredients can be present in the composition as well. Suitable substances and their use for the formulation of pharmaceutically active compounds are well known in the art. A pharmaceutical composition is typically formulated to be compatible with its intended route of administration. For topical application, a pharmaceutical composition may be formulated in a suitable ointment, lotion, gel, or cream containing the active components suspended or dissolved in one or more pharmaceutically acceptable carriers suitable for use in such compositions. For some applications, the composition is formulated as a solid (e.g., lyophilized), liquid, gel, or hydrogel and may contain additives such as surfactants, buffers (e.g., succinate), salts (e.g., sodium chloride), polymers (e.g., polysaccharides, hyaluronic acid), proteins (e.g., albumin, human serum albumin), or amino acids (e.g., methionine).

Methods of Measuring a Level of Activation of a Signal Transducer

Disclosed herein include methods of measuring a level of activation of one or more signal transducers. In some embodiments, the method comprises: expressing a synthetic protein circuit in a cell of a subject in need thereof, the synthetic protein circuit comprising: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting, wherein a level of activation of the effector protein indicates a first level of activation of the first signal transducer and/or a second level of activation of the second signal transducer. Expressing can comprise administering one or more nucleic acids encoding the synthetic protein circuit, such as any of the nucleic acids described herein.

Disclosed herein include embodiments of a method of measuring a level of activation of one or more signal transducers. In some embodiments, the method comprises: expressing a synthetic protein circuit in a cell of a subject in need thereof. The synthetic protein circuit can comprise: a first polypeptide comprising a first signal transducer binding domain and a first part of a first protease domain, wherein the first signal transducer binding domain binds to a first signal transducer of the cell to form a first signal transducer-bound polypeptide. The synthetic circuit can comprise: a second polypeptide comprising a second signal transducer binding domain and a second part of the first protease domain, wherein the second signal transducer binding domain binds to a second signal transducer to form a second signal transducer-bound polypeptide, and wherein the first part of the first protease domain and the second part of the first protease domain associate with each other to constitute a first protease in a first protease active state when the first signal transducer and the second signal transducer are in close proximity at an association location. The synthetic circuit can comprise: an effector protein comprising a first cut site the first protease in the first protease active state cuts to change an activity state/a level of activation of the effector protein. The activity state/the level of activation of the effector protein can indicate a first level of activation of the first signal transducer and/or a second level of activation of the second signal transducer.

The effector protein in an effector active state can be capable of generating a first detectable signal. The effector protein in an effector inactive state can be capable of generating a second detectable signal. A fluorescence emission intensity, fluorescence lifetime, excitation wavelength, and/or emission wavelength of the first detectable signal and second detectable signal can be different. In some embodiments, the method comprises detecting the first detectable signal and/or second detectable signal. In some embodiments, detecting the first detectable signal and/or second detectable signal comprises illumination of the effector protein. The effector protein can comprise all or a portion of a fluorescent protein, a luminescent protein, a phosphorescent protein, or any combination thereof. The effector protein can comprise all or a portion of Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, ZsYellow1, DsRed2, AsRed2, and HcRed1, or any combination thereof. The effector protein can be a molecule capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. For example, the effector protein may comprise, in some embodiments, a fluorescent protein, such as, but not limited to, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, or any combination thereof. In some embodiments, one or more of the fluorescence emission intensity, fluorescence lifetime, excitation wavelength, and/ or emission wavelength of the first detectable signal positively correlates with a level of activation of the effector protein. In some embodiments, one or more of the fluorescence emission intensity, fluorescence lifetime, excitation wavelength, and/or emission wavelength of the first detectable signal and/or second detectable signal positively correlates with a first level of activation of the first signal transducer and/or a second level of activation of the second signal transducer. In some embodiments, the first detectable signal and/or second detectable signal can indicate and/or quantify aberrant signaling.

The methods of measuring a level of activation of one or more signal transducers can be employed in detecting a disease or disorder and/or monitoring the progression of a disease or disorder. As used herein, the term "diagnostic" refers identifying the presence or absence of or nature of a disease or disorder. Such detection methods can be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo. The detection of aberrant signaling of one or more signal transducers as provided herein can serve as a diagnostic or prognostic tool to detect a transformed phenotype, a pre-cancerous condition, or cancerous condition.

Detection and/or imaging of the effector protein can enable a clinician to intraoperatively, laparoscopically, intravascularly or endoscopically detect lesions (e.g. tumors, infected cells). Lesions can be cells characterized by aberrant signaling of one or more signal transducers. The aberrant signaling of one or more signal transducers can be used to distinguish normal cells from cells is a disease or disorder state. In some such embodiments, discrimination between lesions (e.g. tumors) and non-lesions (e.g., non-tumor tissue) is enhanced by the detection and/or imaging of the effector protein. In some embodiments, detection and/or imaging of the effector protein can enable a clinician to accurately locate lesions in a patient and thereby aid resection, irradiation, biopsy and/or lesion removal. In some embodiments, detection and/or imaging of the effector protein aids the detection of non-malignant pathological lesions, such as, an infarct, including myocardial, atherosclerotic plaque, clot, including thrombosis, pulmonary embolism, infectious or inflammatory lesion, non-tumorous or noninfectious inflammation, or hyperplasia. The detection and/or imaging of the effector protein may also be used to detect various stages of progression or severity of disease (e.g., benign, premalignant, and malignant breast lesions, tumor growth, or metastasis). The detection and/or imaging of the effector protein may also be used to detect the response of the disease to prophylactic or therapeutic treatments or other interventions. The detection and/or imaging of the effector protein can furthermore be used to help the medical practitioner in determining prognosis (e.g., worsening, status-quo, partial recovery, or complete recovery) of the patient, and the appropriate course of action.

Detection and/or imaging of the effector protein can be performed, for example, using an ultrasound scanner, a magnetic resonance imaging instrument (MRI scanner), an X-ray source with film or a detector (e.g., conventional or digital radiography system), an X-ray computed tomography (CT) or computed axial tomography (CAT) scanner, a gamma camera, or a positron emission tomography (PET) scanner. Various medical imaging systems have been developed for open surgery as well as for laparoscopic, thoracoscopic, and robot-assisted surgery and can be used in the practice of the methods provided herein. Conventional laparoscopes and endoscopes can be equipped with a photodetector (e.g., camera or CCD detector) to provide guidance during medical procedures. Fiber-optic imaging systems can also be used, which include portable handheld microscopes, flexible endoscopes, and microendoscopes. For example, an illumination source can be added to such devices to allow fluorescence imaging. A miniaturized ultrasound transducer can be added to the tip of a laparoscope or catheter for intravascular ultrasound (IVUS) imaging. Miniaturized imaging systems can be used that allow imaging inside small cavities and constricted spaces. In addition, miniaturized imaging devices (e.g., microendoscopes) may be implanted within a subject for long-term imaging studies. In addition, a camera may be used to take both photographic images of a subject and to detect signals from the effector protein, so that photographic images of the subject and images of the signals from the effector protein can be superimposed to allow regions containing the effector to be mapped to the subject's anatomy.

Nucleic Acids

Disclosed herein include nucleic acids encoding a synthetic protein circuit. In some embodiments, the nucleic acid encodes a synthetic protein circuit comprising: a first polypeptide comprising a first signal transducer binding domain and a first part of a first protease domain, wherein the first signal transducer binding domain is capable of binding a first signal transducer to form a first signal transducer-bound polypeptide; a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting.

The nucleic acid can comprise at least one regulatory element for expression of the synthetic protein circuit. The nucleic acid can comprise a vector, such as any of the viral vectors described in U.S. application Ser. No. 16/555,604, filed on Aug. 29, 2019, the content of which is incorporated herein by reference in its entirety. In some embodiments, the vector can comprise an adenovirus vector, an adeno-associated virus vector, an Epstein-Barr virus vector, a Herpes virus vector, an attenuated HIV vector, a retroviral vector, a vaccinia virus vector, or any combination thereof. In some embodiments, the vector can comprise an RNA viral vector. In some embodiments, the vector can be derived from one or more negative-strand RNA viruses of the order Mononegavirales. In some embodiments, the vector can be a rabies viral vector. Many such vectors useful for transferring exogenous genes into target mammalian cells are available. The vectors may be episomal, e.g. plasmids, virus-derived vectors such cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Retroviral vectors can be "defective", i.e. unable to produce viral proteins required for productive infection. Replication of the vector can require growth in the packaging cell line. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., a synthetic protein circuit component) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector. One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector. Other non-integrative viral vectors contemplated herein are single-strand negative-sense RNA viral vectors, such Sendai viral vector and rabies viral vector. Another example of a non-integrative vector is a minicircle vector. Minicircle vectors are circularized vectors in which the plasmid backbone has been released leaving only the eukaryotic promoter and cDNA(s) that are to be expressed. As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of nonessential viral genes. The vector and/or particle may be utilized for the purpose of transferring nucleic acids into cells either in vitro or in vivo. Numerous forms of viral vectors are known in the art.

In some embodiment, the vectors can include a regulatory sequence that allows, for example, the translation of multiple proteins from a single mRNA. Non-limiting examples of such regulatory sequences include internal ribosome entry site (IRES) and 2A self-processing sequence. In some embodiments, the 2A sequence is a 2A peptide site from foot-and-mouth disease virus (F2A sequence). In some embodiments, the F2A sequence has a standard furin cleavage site. In some embodiments, the vector can also comprise regulatory control elements known to one of skill in the art to influence the expression of the RNA and/or protein products encoded by the polynucleotide within desired cells of the subject. In some embodiments, functionally, expression of the polynucleotide is at least in part controllable by the operably linked regulatory elements such that the element(s) modulates transcription of the polynucleotide, transport, processing and stability of the RNA encoded by the polynucleotide and, as appropriate, translation of the transcript. A specific example of an expression control element is a promoter, which is usually located 5' of the transcribed sequence. Another example of an expression control element is an enhancer, which can be located 5' or 3' of the transcribed sequence, or within the transcribed sequence. Another example of a regulatory element is a recognition sequence for a microRNA. Another example of a regulatory element is an ration and the splice donor and splice acceptor sequences that regulate the splicing of said intron. Another example of a regulatory element is a transcription termination signal and/or a polyadenylation sequence.

Expression control elements and promoters include those active in a particular tissue or cell type, referred to herein as a "tissue-specific expression control elements/promoters." Tissue-specific expression control elements are typically active in specific cell or tissue (for example in the liver, brain, central nervous system, spinal cord, eye, retina or lung). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1 alpha; or synthetic elements that are not present in nature.

Expression control elements also can confer expression in a manner that is regulatable, that is, a signal or stimuli increases or decreases expression of the operably linked polynucleotide. A regulatable element that increases expression of the operably linked polynucleotide m response to a signal or stimuli is also referred to as an "inducible element" (that is, it is induced by a signal). Particular examples include, but are not limited to, a hormone (for example, steroid) inducible promoter. A regulatable element that decreases expression of the operably linked polynucleotide in response to a signal or stimuli is referred to as a "repressible element" (that is, the signal decreases expression such that when the signal, is removed or absent, expression is increased). Typically, the amount of increase or decrease conferred by such elements is proportional to the amount of signal or stimuli present: the greater the amount of signal or stimuli, the greater the increase or decrease in expression.

The first polypeptide, the second polypeptide, the effector protein, and/or the repressor protein can be encoded on a single open reading frame, and wherein two or more of the first polypeptide, the second polypeptide, the effector protein, and repressor protein can be separated by one or more self-cleaving peptides. The first polypeptide, the second polypeptide, the effector protein, and/or the repressor protein can be encoded on a single transcript, and wherein translations of the first polypeptide, the second polypeptide, the effector protein, and/or the repressor protein can be each driven by a separate internal ribosome entry site. The sequences of the internal ribosome entry sites can be identical or different.

Synthetic Protein Circuit Embodiments

The synthetic protein circuits provided herein can be configured in a variety of ways. In some embodiments, the synthetic protein circuit includes a first protease, second protease, third protease, fourth protease, fifth protease, sixth protease, seventh protease, eighth protease, ninth protease and/or tenth protease. Any of said proteases may comprise or be composed of a compound protease as described herein.

Some embodiments of the systems, methods and compositions described herein relate to a compound protease. In some embodiments, the compound protease comprises a protease domain with a cut site for another protease, wherein the compound protease is deactivated by cleavage of cut site for the other protease. In some embodiments, the compound protease is activated or deactivated by another protease, thereby forming a protein circuit. The protein circuits may be programmable with different variations on the proteases and their targets to, for example, perform logic gate functions, or be part of bandpass or adaptive pulse circuits.

There are provided methods, compositions, and systems for engineering viral proteases to regulate one another and/or target proteins. The methods provided herein enable engineering of circuits that perform regulatory cascades, binary logic computations, analog band-pass signal processing, generation of dynamic behaviors such as pulsing, coupling to endogenous cellular states such as oncogene activation, and/or the ability to control cellular behaviors such as apoptosis. The flexibility and scalability of the system enables it to be reconfigured to implement a broad range of additional functions in some embodiments. The circuits can also be encoded and delivered to cells in multiple formats, including DNA, RNA, and at the protein level itself, enabling versatile applications with or without genomic integration or mutagenesis.

Figure 5A:
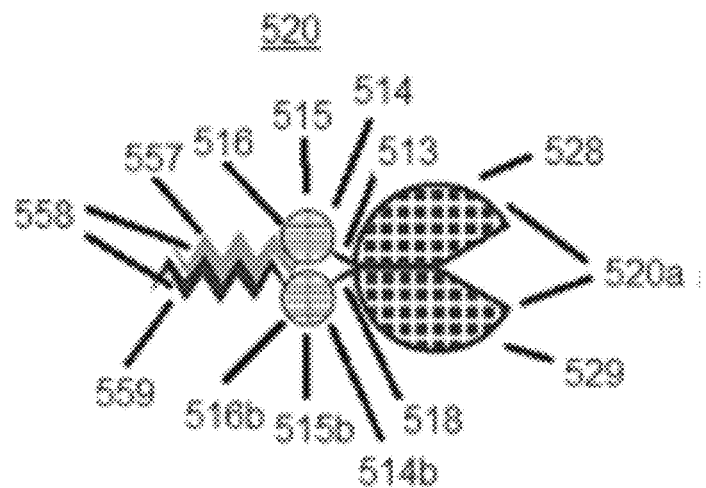
FIGS. 5A-5C depict nonlimiting examples of compound proteases as described herein.
Figure 5B:
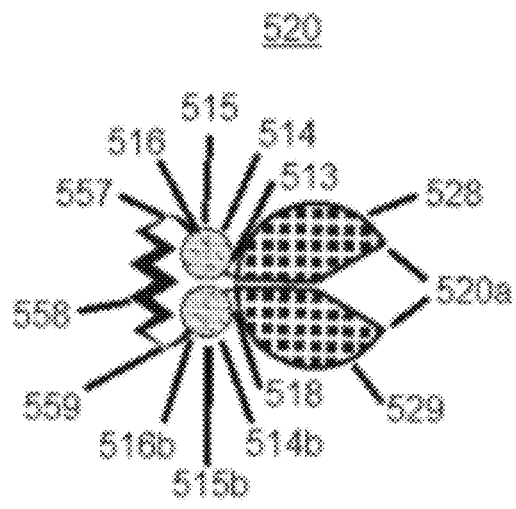
Figure 5C:
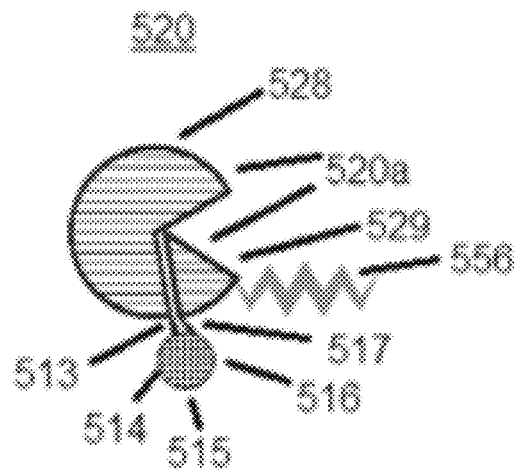

Some non-limiting examples of compound proteases are shown in FIGS. 5A-5C In some embodiments, the compound protease 520 comprises a) a protease domain 520*a* comprising: a first part 528 of the protease domain 520*a*, and a second part 529 of the protease domain 520*a*, wherein when the first part 528 and the second part 529 of the protease domain 520*a* are associated together, they form an active protease domain 520*a*, and wherein the first part 528 and the second part 529 of the protease domain 520*a* do not self-associate on their own to form the active protease domain 520*a*; b) a cut site 515, wherein the cut site 515 comprises: a first part 514 of the cut site 515, wherein the first part 514 of the cut site 515 is linked to the first part 528 of the protease domain 520*a*; and a second part 516 of the cut site 515, wherein the second part 516 of the cut site 515 is linked to the second part 529 of the protease domain 520*a*, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another; and c) an association domain 558, the association domain 558 comprising: a first part 557 of the association domain 558 that is conjugated to the second part 516 of the cut site 515; a second part 559 of the association domain 558 that is linked to the second part 529 of the protease domain 520*a*, wherein the association domain 558 is configured to stabilize the active protease domain 520*a*.

As described herein, a "compound protease" refers to a protease with at least two parts of a protease domain. The parts may be linked together by one or more cut sites such as a cut site specific for another protease. The parts of the protease domain may but need not be separate subunits of the protease, or may include separate portions of a peptide or peptides that makes up the protease.

As described to herein, a "protease domain" includes one or more peptides that when associated together have protease activity. For example, the protease activity may be the ability to cleave another peptide.

As described herein, a "cut site" is a peptide sequence specific for one or more proteases that when recognized or bound by the one or more proteases are cleaved by the one or more proteases. The peptide sequence of the cut site may be specific for one protease or a type of proteases, or may be general to multiple proteases or types of proteases.

As used herein, "stabilize" may refer to the ability of a peptide or molecule to maintain the same or another molecule or peptide in a particular state such as an active conformation. "Stabilize" may also refer to the ability of a peptide or molecule to prevent or decrease the amount of degradation that the same or another molecule or peptide faces.

As used herein, "destabilize" may refer to the ability of a peptide or molecule to prevent or stop the same or another molecule or peptide from maintaining a particular state. "Destabilize" may also refer to the ability of a peptide or molecule to allow or increase the amount of degradation that the same or another molecule or peptide faces, such as by increasing the affinity of the same or other molecule or peptide to a digestive protein.

Some embodiments include the use of degrons. Examples of degrons include a portion of a protein that affect the regulation of protein degradation rates. Some degrons are ubiquitin-dependent or ubiquitin-independent.

Some embodiments of the compound protease include a protease domain. Examples of protease domains are shown in FIGS. 5A and 5B. The protease domain 520A in each of FIGS. 5A and 5B includes a first part 528 and a second part 529. Examples of a first and second part of a protease domain include separate halves or pieces of a dimer that work together to cleave a peptide, or separate portions of a protease that do not dimerize or that are not halves. For example, one part of a protease domain may be a fourth of the protease while another part of the protease domain may be three fourths of the protease domain, or there may be more than two parts. Each of the parts 528, 529 of each of the protease domains 520a in FIGS. 5A and 5B are separate halves of the protease domain 520a and are connected to a cut site 515, 515b by a linking peptide 513, 518. Another example of a protease domain 520a is shown in FIG. 5C, which includes a first part 528 and a second part 529, wherein the first part 528 is larger than the second part 529. In the example in FIG. 5C, the first and second parts 528, 529 of the protease domain 520a are each connected to different parts 514, 516 of a single cut site 515 by linking peptides 513, 517.

In some embodiments, the protease domain comprises a first part 528 of the protease domain 520a, and a second part 529 of the protease domain 520a. In some embodiments, the first part 528 and the second part 529 of the protease domain 520a associate together. In some embodiments, when the first part 528 and the second part 529 of the protease domain 520a are associated together, they form an active protease domain 520a. In some embodiments, the first part 528 and the second part 529 of the protease domain 520a do not self-associate on their own to form the active protease domain 520a. For example, the protease domain 520a may include a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own to form the active protease domain 520a.

Some embodiments of the compound protease include a cut site. A cut site may be made of two parts that associate together to form the cut site. The cut site may be specific to an individual protease, or may be specific to multiple proteases. Examples of cut sites are shown in FIGS. 5A-5C. In the examples shown in each of FIGS. 5A and 5B, two cut sites 515, 515b are shown. One of the cut sites in each of FIGS. 5A and 5B 515 includes a first part 514 of the cut site 515 and a second part 516 of the cut site 515, the first part 514 connecting to the first part 528 of the protease domain 520, and the second part 516 of the cut site 515 connecting directly to a part 557 of an association domain 558 and linking indirectly through the association domain 558 to the second part 529 of the protease domain 520a. The second site 515b in each of FIGS. 5A and 5B also includes a first part 514b of the cut site 515b and a second part 516b of the cut site 515b, the first part 514b connecting directly to the second part 529 of the protease domain 520a, and the second part 516b of the cut site 515b connecting directly to a part 559 of the association domain 558 and linking indirectly through the association domain 558 to the first part 528 of the protease domain 520. In the example shown in FIG. 5C, the protease 520 includes a single cut 515 having two parts 514, 516, each part connecting directly to a part 528, 529 of the protease domain 520a through a linking peptide 513, 517.

In some embodiments, the cut site comprises a first part 514 of the cut site 515. In some embodiments, the first part 514 of the cut site 515 is linked to the first part 528 of the protease domain 520a. In some embodiments, the cut site comprises a second part 516 of the cut site 515. In some embodiments, the second part 516 of the cut site 515 is linked to the second part 529 of the protease domain 520a. In some embodiments, the first and second parts 514, 516 of the cut site 515 associate together. In some embodiments, when the first and second parts 514, 516 of the cut site 515 are associated together they form an active cut site 515 for an enzyme. In some embodiments, when the active cut site 515 is cut by the enzyme, the first and second parts 514, 516 of the cut site 515 dissociate from one another. In some embodiments, when the first and second parts 514, 516 of the cut site 515 are dissociated from one another, the protease domain 520a is inactive or deactivated. For example, the cut site may include a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another.

Some embodiments of the compound protease include an association domain. An example of an association domain is shown in FIG. 5A. The association domain 558 in FIG. 5A includes two parts 557, 559 each binding together noncovalently to ultimately link the first and second parts 528, 529 of the protease domain 520a together. Another example of an association domain is shown in FIG. 5B. The association domain 558 in FIG. 5B includes a single peptide strand with two parts 557, 559 that each connect to a cut site 515, 515b and ultimately link the first and second parts 528, 529 of the protease domain 520a together. In some embodiments, the association domain comprises a first part 557 of the association domain 558. In some embodiments, the first part 557 of the association domain 558 is conjugated to the second part 516 of the cut site 515. In some embodiments, the association domain comprises a second part 559 of the association domain 558. In some embodiments, the second part 559 of the association domain 558 is linked to the second part 529 of the protease domain 520a. In some embodiments, the association domain 558 is configured to stabilize the active protease domain 520a. For example, the association domain may include a first part 557 of the association domain 558 that is conjugated to the second part 516 of the cut site 515; a second part 559 of the association domain 558 that is linked to the second part 529 of the protease domain 520a, wherein the association domain 558 is configured to stabilize the active protease domain 520a.

Examples of association domains include a leucine zipper motif or a complementary leucine zipper motif, a scaffold protein or a fragment thereof, a scaffold-binding motif, an antibody, an epitope, tetratricopeptide repeat, a tetracopeptide repeat-binding motif, a G-protein-coupled receptor, a β-arrestin, and/or a G protein. In some embodiments, the association domain includes any protein(s) or component(s) of protein(s) that bind together. Thus, the association domain is contemplated to cover any protein-protein interaction according to some embodiments. In some embodiments, the association domain includes a ligand-binding protein or domain and/or the ligand.

In some embodiments of the compound protease, the first and second parts of the association domain of the compound protease comprise separate peptide strands that hybridize together, for example, as shown in FIG. 5A. In some embodiments of the compound protease, the first and second parts 557, 559 of the association domain 558 of the compound protease 520 are a single peptide strand, for example, as shown in FIG. 5B.

Some embodiments do not include an association domain linking the first and second parts 528, 529 of a protease domain 520a together. For example, in the example shown in FIG. 5C, the first and second parts 528, 529 of the protease domain 520a are instead linked together through the cut site. The example in FIG. 5C shows the use of optional linking peptides 513, 517 which some embodiments do not include. The example in FIG. 5C does include a part 556 of an association domain for a different purpose— that of helping to recruit another protease or compound protease to the cut site 515 of the protease 520 in FIG. 5C. For example, the other protease or compound protease may be recruited to the cut site 515 of the protease 520 in FIG. 5C when the other protease or compound protease includes a complementary part of the association domain to the part 556 of the association domain included on the protease domain 520a of the protease 520 shown in FIG. 5C.

In some embodiments, the compound protease comprises or consists of a tobacco etch virus NIa (TEV) protease, tobacco vein mottling virus (TVMV) NIa protease, sugarcane mosaic virus NIa protease, sunflower mild mosaic virus NIa protease, turnip mosaic virus NIa protease, plum pox virus NIa protease, soybean mosaic virus protease, hepatitis c virus (HCV) ns3 protease, hepatitis a virus 3c protease, dengue virus NS3 protease, zika virus NS3 protease, yellow fever virus NS3 protease, or human herpes virus 1 protease. In some embodiments, the compound protease comprises or consists of a human site-specific protease such as thrombin and/or enteropeptidase.

Proteases

In some embodiments, the compound protease includes a protease domain, one or more cut sites, and/or one or more association domains and/or parts of association domains. In some embodiments, the protease includes a compound protease such as is shown in any of FIGS. 5A-5C. For example, the protease may include a) a protease domain 520a including: a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own at physiological conditions to form the active protease domain 520a; b) a cut site 515, wherein the cut site 515 includes: a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another; and c) an association domain 558, the association domain 558 including: a first part 557 of the association domain 558 that is conjugated to the second part 516 of the cut site 515; a second part 559 of the association domain 558 that is linked to the second part 529 of the protease domain 520a, wherein the association domain 558 is configured to stabilize the active protease domain 520a.

In some embodiments, the ability or lack thereof of the first part 528 and the second part 529 of the protease domain 520a to self-associate on their own to form the active protease domain 520a is concentration dependent such that at physiological conditions they do not self-associate.

In some embodiments, the protease domain comprises, is comprised of, or is composed of a peptide or co-peptide, or multiple peptides or co-peptides.

In some embodiments, the compound protease includes one or more cut sites. In some embodiments, one or more of the cut sites are specific for a different protease or different proteases than the compound protease. For example, the compound protease would not be able to cleave itself according to some embodiments. Thus, in some embodiments, the compound protease is not naturally occurring, and/or the compound protease does not include a natural cut site (such as for the protease itself). For example, the compound protease may not include a natural cut site for itself between a main protease domain and a co-peptide of the compound protease.

Some embodiments of the protease include a compound protease such as the compound protease 520 shown in FIG. 5C, the compound protease 520 including: a) a protease domain 520a including: a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own to form the active protease domain 520a; b) a cut site 515, wherein the cut site 515 includes: a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another; c) a first peptide 513 connecting the first part 528 of the protease domain 520a to the first part 514 of the cut site 515; and d) a second peptide 517 connecting the second part 529 of the protease domain 520a to the second part 516 of the cut site 515, wherein the first and second linkers 513, 517 are configured to stabilize the active protease domain 520a. In some embodiments, the first peptide 513 connecting the first part 528 of the protease domain 520a to the first part 514 of the cut site 515 includes a linker. In some embodiments, the second peptide 517 connecting the second part 529 of the protease domain 520a to the second part 516 of the cut site 515 includes a linker.

Some embodiments of the protease include a compound protease such as the compound protease 520 shown in FIGS. 5A-5C, the compound protease 520 including: a) a protease domain 520a including: a first part 528 of the protease domain 520a, and a second part 529 of the protease domain 520a, wherein when the first 528 part and the second part 529 of the protease domain 520a are associated together, they form an active protease, and wherein the first part 528 and the second part 529 of the protease domain 520a do not self-associate on their own to form the active protease; and b) a cut site 515, wherein the cut site 515 includes: a first part 514 of the cut site 515, wherein the first part 514 of the cut site 515 is linked to the first part 528 of the protease domain 520a; and a second part 516 of the cut site 515, wherein the second part 516 of the cut site 515 is linked or indirectly connected to the second part 529 of the protease domain 520*a*, wherein when the first and second parts 514, 516 of the cut site 515 are associated together they form an active cut site 515 for an enzyme, and wherein when the active cut site 515 is cut by the enzyme, the first and second parts 514, 516 of the cut site dissociate from one another.

In some embodiments of the compound protease, such as is shown in FIG. 5C, the first part 514 of the cut site 515 is covalently linked to the first part 528 of the protease domain 520*a* by a first peptide linkage 513, and/or wherein the second part 516 of the cut site 515 is covalently linked to the second part 529 of the protease domain 520*a* by a second peptide linkage 517.

Some embodiments of the proteases described herein include one or more linkers or linker peptides. The linkers or linker peptides may connect or link (directly or indirectly, and/or covalently or noncovalently) various parts of the protease such as a cut site or a part of the cut site to a protease domain or a part of a protease domain. However, this disclosure is not limited to only linkers or linker peptides connecting the protease parts. Examples of a linker is a peptide that includes 1-10, 10-25, 25-50, 50-100, or 100-1000 amino acids. For example, the compound protease may include a first peptide linkage 513 that includes a linker peptide including 1-10, 10-25, 25-50, 50-100, or 100-1000 amino acids, and/or a second peptide linkage 517 includes a linker peptide including 1-10, 10-25, 25-50, 50-100, or 100-1000 amino acids.

In some embodiments of the compound protease, wherein the second part 529 of the protease domain 520*a* includes a part 556 of an association domain connected to the second part 529 of the protease domain 520*a*, wherein the part 556 of the association domain connected to the second part 529 of the protease domain 520*a* is configured to recruit the enzyme to the active cut site 515 by binding a second part of the association domain on the enzyme.

In some embodiments of the compound protease, such as is shown in FIGS. 5A and 5B, the compound protease includes a second cut site 515*b*, wherein the second cut site 515*b* includes: a first part 514*b* of the second cut site 515*b*, wherein the first part 514*b* of the second cut site 515*b* is linked to the second part 529 of the protease domain 520*a*; and a second part 516*b* of the second cut site 515*b*, wherein the second part 516*b* of the second cut site 515*b* is linked or indirectly connected to the first part 528 of the protease domain 520*a*; wherein when the first and second parts 514*b*, 516*b* of the second cut site 515*b* are associated together they form an active second cut site 515*b* for the enzyme, and wherein when the active second cut site 515*b* is cut by the enzyme, the first and second parts 514*b*, 516*b* of the second cut site dissociate from one another.

In some embodiments of the compound protease, such as is shown in FIG. 5A, the compound protease includes an association domain 558 that includes: a first part 557 of the association domain 558, conjugated to the second part 516 of the first cut site 515; a second part 559 of the association domain 558, conjugated to the second part 516*b* of the second cut site 515*b*, wherein the association domain 558 is configure to stabilize the active protease domain. In some embodiments of the compound protease, the first part 514 of the cut site 515 is covalently linked to the first part 528 of the protease domain 520*a* by a first peptide linkage 513, and/or wherein the first part 514*b* of the second cut site 515*b* is covalently linked to the second part 529 of the protease domain 520*a* by a second peptide linkage 518. In some embodiments, the first peptide linkage 513 includes a linker peptide including 1-10, 10-25, 25-50, 50-100, or 100-1000 amino acids. In some embodiments, the second peptide linkage 518 includes a linker peptide including 1-10, 10-25, 25-50, 50-100, or 100-1000 amino acids. In some embodiments of the compound protease, the second part 516 of the cut site 515 is indirectly connected to the second part 529 of the protease domain 520*a* through the association domain 558, wherein the first and second parts 557, 559 of the association domain are covalently or non-covalently linked together.

Some embodiments of the compound protease, such as the example shown in FIG. 5B, include an association domain 558 of the compound protease 520 including a first part 557 and a second part 559, wherein the first part 557 of the association domain 558 links to the second part 516 of the first cut site 515, and wherein the second part 559 of the association domain 558 links to the second part 516*b* of the second cut site 515*b*. In some embodiments, the first part 514 of the cut site 515 is covalently linked to the first part 528 of the protease domain 520*a* by a first peptide linkage 513, and/or wherein the first part 514*b* of the second cut site 515*b* is covalently linked to the second part 529 of the protease domain 520*a* by a second peptide linkage 518. In some embodiments, the first peptide linkage 513 includes a linker peptide including 1-10, 10-25, 25-50, 50-100, or 100-1000 amino acids. In some embodiments, the second peptide linkage 518 includes a linker peptide including 1-10, 10-25, 25-50, 50-100, or 100-1000 amino acids. In some embodiments, the second part 516 of the cut site 515 is indirectly connected to the second part 529 of the protease domain 520*a* through the association domain 558. In some embodiments, the association domain connecting to the second part 516 of the cut site 515 and to the to the second part 516*b* of the second cut site 515*b* is configured to recruit the enzyme to the active cut site 515 and/or to the active second cut site 515*b* by binding a second part of the association domain on the enzyme.

In some embodiments of the compound protease, the compound protease includes a degron. In some embodiments, the compound protease includes multiple degrons. In some embodiments, at least one degron of the compound protease destabilizes the compound protease when present on the compound protease by enhancing degradation of the compound protease. In some embodiments, at least one of the degrons of the compound protease is or comprises a conditional N-end degron. In some such embodiments, the at least one degron or the condition N-end degron does not inactivate or destabilize the compound protease until the degron or a component thereof is cleaved by another protease to reveal the degron and allow it to stabilize the compound protease. In some embodiments, one or more degrons of the compound protease comprise a conditional N-end degron such as an N-end degron that is conditional on cleavage of a cut site specific for an enzyme, a second protease, or the compound protease, on the compound protease.

In some embodiments, the protease or compound protease is a viral protease, or is a modified form of a viral protease. In some embodiments, the protease or compound protease is a mammalian or human protease, or is a modified form of a mammalian or human protease.

Some embodiments of the compound proteases or of a target protein for a protease include a localization tag. Such localization enables sub-cellular computation or signal transduction in some embodiments. In some cases, the protease (or split protease) includes the localization sequence at one or more termini of protease.

Some embodiments relate to a protease such as a compound protease that interacts with another enzyme or protease by being positively regulated by that other enzyme or protease. Thus, some embodiments of the compound protease include a degron linked to a protease domain or other component of the compound protease by a cut site of the compound protease. The degron may act to destabilize the compound protease as long as the degron is present on the compound protease. In some such embodiments, cleavage of the cut site removes the degron to stabilize the compound protease. In some embodiments, the compound protease is configured to be activated and/or destabilized by another compound protease, protease, or enzyme. In some embodiments, the compound protease is configured to be deactivated and/or destabilized by another compound protease, protease, or enzyme.

Some embodiments relate to positive regulation for cellular protein-level regulation circuits. Positive regulation of one protein activity by another is beneficial for some protein-level circuits. Two non-limiting exemplary synthetic protein circuit designs described herein are (1) Reversible activation by swappable association domains; and (2) Irreversible activation by intein-mediated protein splicing.

In some embodiments, the compound protease is cleavage-activatable by another protease. For example, the compound protease may be tagged with an auto-inhibitory domain that can be removed with another protease. In some embodiments, the compound protease is tagged with a degron (such as a DHFR degron) that can be removed with another protease. In some embodiments, the compound protease comprises a split protease tagged with a degron (for example, four tandem repeats of ubiquitin) on the end of a leucine zipper, and the degron is removable by another protease. In some embodiments, the compound protease includes an N-terminal half that is caged with a complementary leucine zipper and/or a catalytically inactive C-terminal half, and the caging domains are removable with another protease.

Some embodiments relate to a compound protease, the compound protease comprising: a) a protease domain comprising: a first part of the protease domain, and a second part of the protease domain, wherein when the first part and the second part of the protease domain are associated together, they form an active protease domain; and/or b) a cut site, wherein the cut site comprises: a first part of the cut site, and a second part of the cut site, wherein when the first and second parts of the cut site are associated together they form an active cut site for an enzyme, and wherein when the active cut site is cut by the enzyme, the first and second parts of the cut site dissociate from one another; wherein the compound protease is configured to be activated or deactivated by cleavage of the active cut site by the enzyme.

Some embodiments relate to a cleavage-activatable compound protease, comprising: a) a protease domain comprising: a first part of the protease domain, and a second part of the protease domain, wherein when the first part and the second part of the protease domain are associated together, they form an active protease domain; and/or b) a cut site, wherein the cut site comprises: a first part of the cut site, and a second part of the cut site, wherein when the first and second parts of the cut site are associated together they form an active cut site for an enzyme, and wherein when the active cut site is cut by the enzyme, the first and second parts of the cut site dissociate from one another; wherein the compound protease is configured to be activated by cleavage of the active cut site by the enzyme. In some embodiments, the cleavage-activatable compound protease comprises an association domain, and the association domain prevents the first part of the protease domain from associating with the second part of the protease until the cut site is cut by the enzyme. In some embodiments, the cleavage-activatable compound protease comprises an association domain, wherein the association domain cages the first part of the protease domain and prevents the first part of the protease domain from associating with the second part of the protease until the cut site is cut by the enzyme. In some embodiments, the cleavage-activatable compound protease further comprises a three-way split protease.

Systems

Some embodiments relate to a system such as a synthetic protein circuit. The system or synthetic protein circuit may include any of the proteases described herein such as one or more of the compound proteases shown in FIGS. 5A-5C. In some embodiments, the system or synthetic protein circuit includes a first protease, second protease, third protease, fourth protease, fifth protease, sixth protease, seventh protease, eighth protease, ninth protease and/or tenth protease. Any of said proteases may comprise or be composed of a compound protease as described herein. In some embodiments of the system or synthetic protein circuit, the first protease 110 and the second protease 120 each include an HCV protease, a TEV protease, or a TVMV protease. Some embodiments include positive protease-protease regulation. For example, some embodiments relate to a synthetic protein circuit that includes a mode of positive protease-protease regulation, such as one that is mediated through degron removal.

Figure 6:
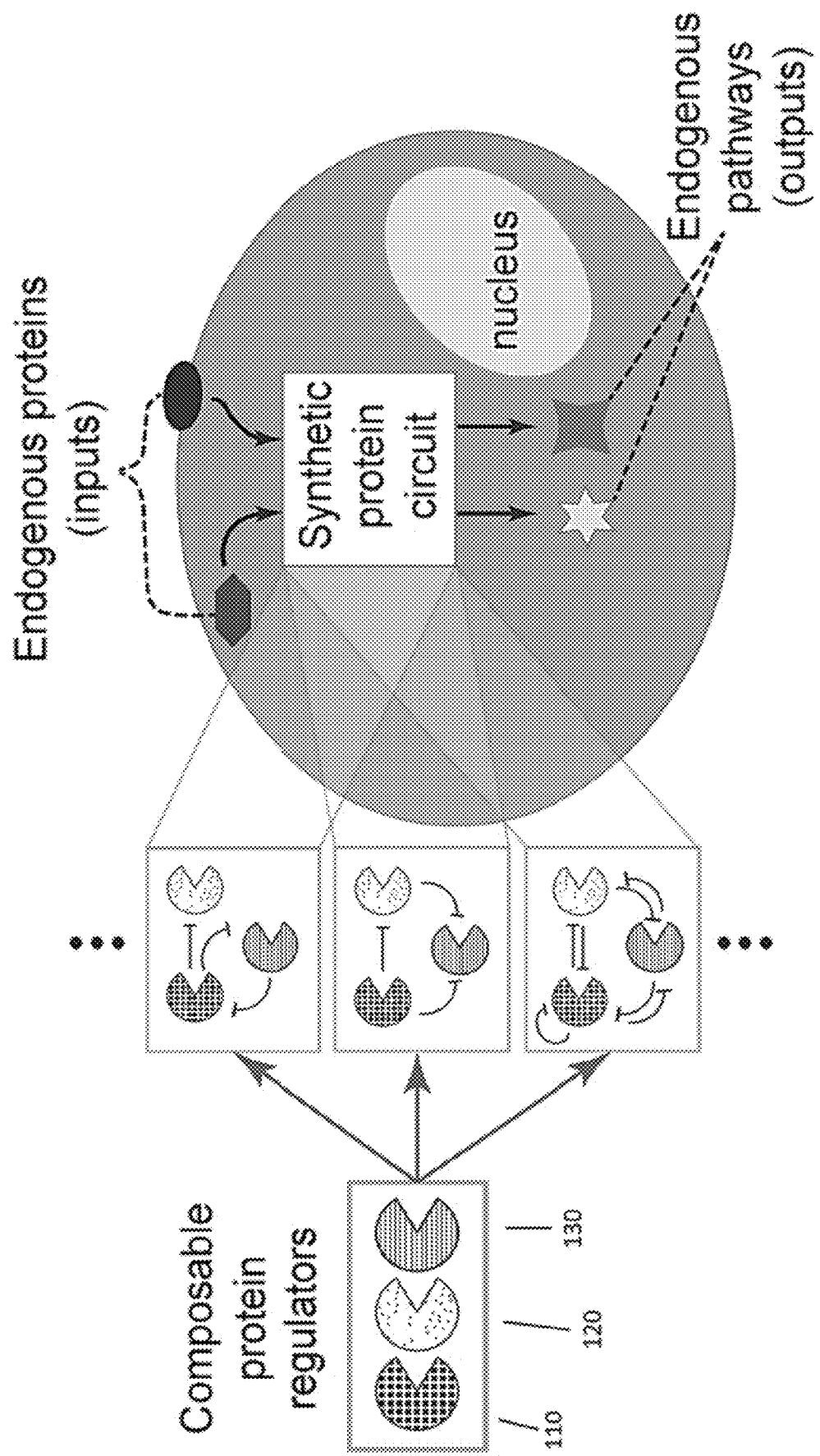
FIG. 6 shows a non-limiting exemplary schematic illustration of how composable protein units can regulate one another in arbitrary configurations with diverse functions (middle). Protein-level circuits can interface directly with endogenous protein pathways and operate without modifying the genome or entering the nucleus. (right).

Some embodiments relate to a synthetic protein circuit such as a protein circuit or a part thereof shown in FIGS. 5, 7A-7B, 8, and 9A-9D. FIG. 6 shows a non-limiting exemplary schematic illustration of how composable protein units can regulate one another in arbitrary configurations with diverse functions (middle). Protein-level circuits can interface directly with endogenous protein pathways and operate without modifying the genome or entering the nucleus (right). Synthetic biology allows for rational design of circuits that confer new functions in living cells. Many natural cellular functions are implemented by protein-level circuits, in which proteins specifically modify each other's activity, localization, or stability. For example, caspase-mediated programmed cell death is regulated by a circuit of proteases that activate one another through cleavage. Synthetic protein circuits could provide advantages over gene regulation circuits, including faster operation, direct coupling to endogenous pathways, single transcript delivery, and function without genomic integration (FIG. 6).

In some embodiments, the synthetic protein circuit includes: a first protease 110; and a second protease 120 including a cut site 115 specific for the first protease 110, wherein the second protease 120 is inactivated by cleavage of the cut site 115 specific for the first protease 110.

Figure 8:
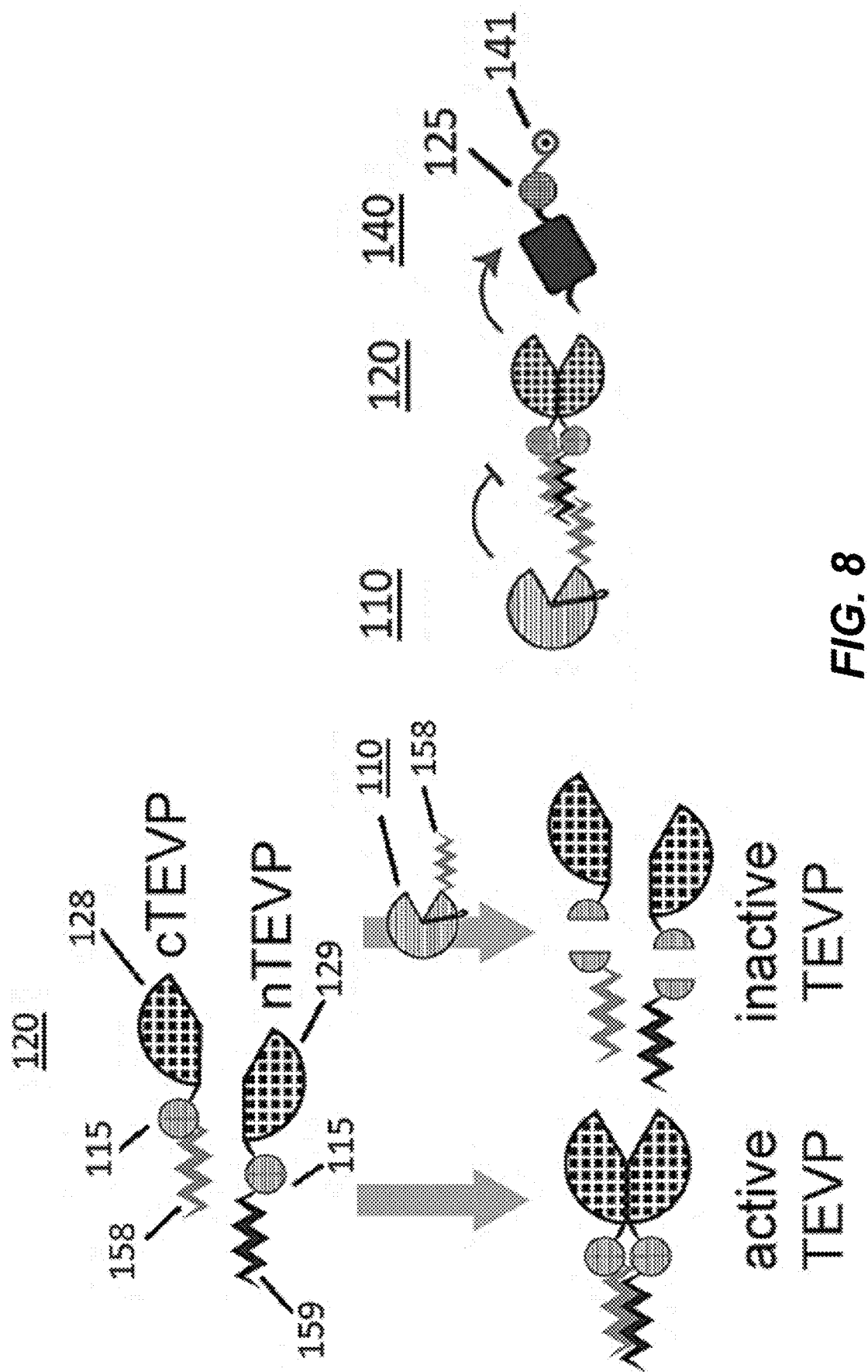
FIG. 8 shows a non-limiting exemplary schematic illustration of the design for some protease-repressible proteases provided herein. TEVP was split as indicated and then reconstituted through dimerizing leucine zippers. A leucine-zipper-tagged HCVP can dock with the target TEVP and cleave it to remove leucine zippers, effectively repressing TEVP.
Figure 9A:
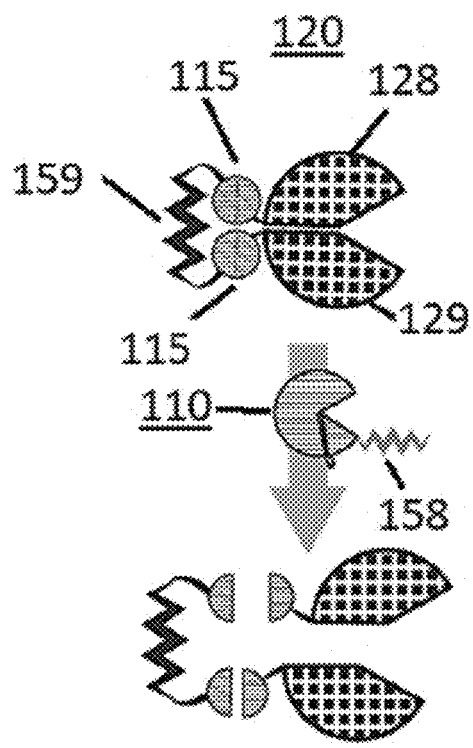
FIGS. 9A-9B show non-limiting exemplary schematic illustrations of how a single-chain variant of the HCV-repressible TEVP allows docking of, and repressive cleavage by, HCVP.
Figure 9B:
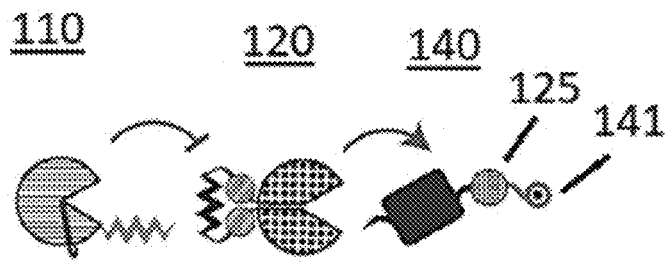
Figure 9C:
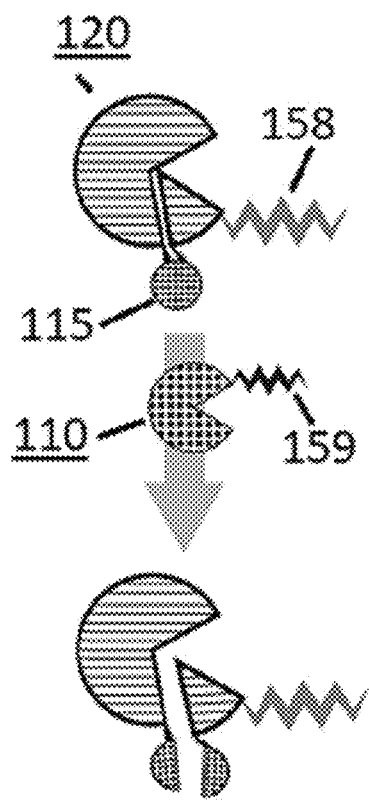
FIGS. 9C-9D show non-limiting exemplary schematic illustrations of how protease regulation can propagate through a three-stage cascade. Repressible HCVP uses a variant design, in which TEVP cleavage separates core HCVP from its docking leucine zipper and activity-enhancing co-peptide.
Figure 9D:
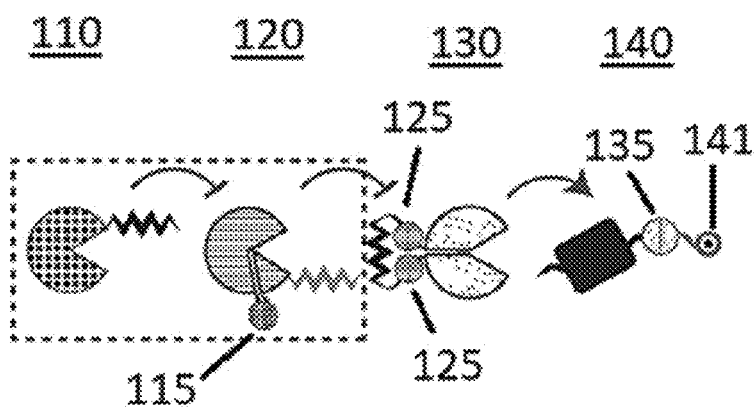
Figure 10A:
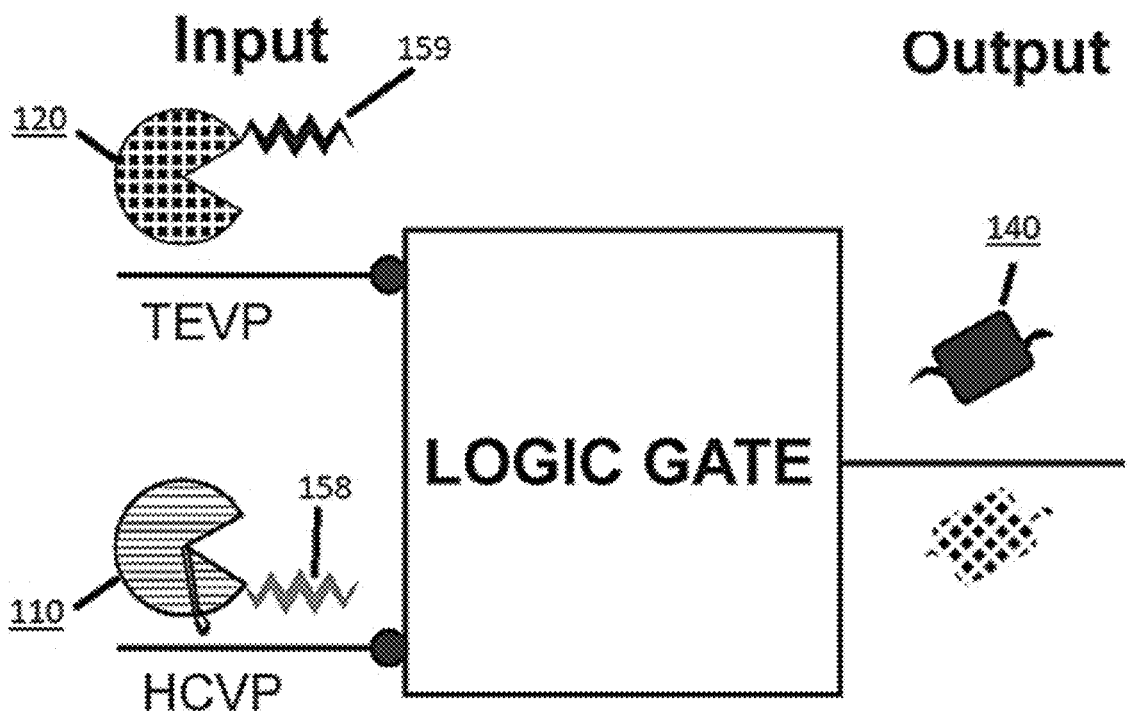
FIGS. 10A-10I show a non-limiting exemplary schematic illustrations of example synthetic protein circuits implementing binary logic gates in accordance with some embodiments. For each indicated gate, TEVP and HCVP can serve as binary inputs and citrine fluorescence serves as gate output.
Figure 10B:
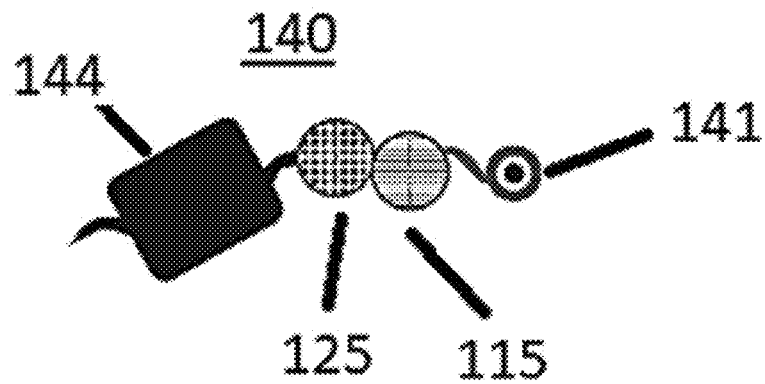
Figure 10C:
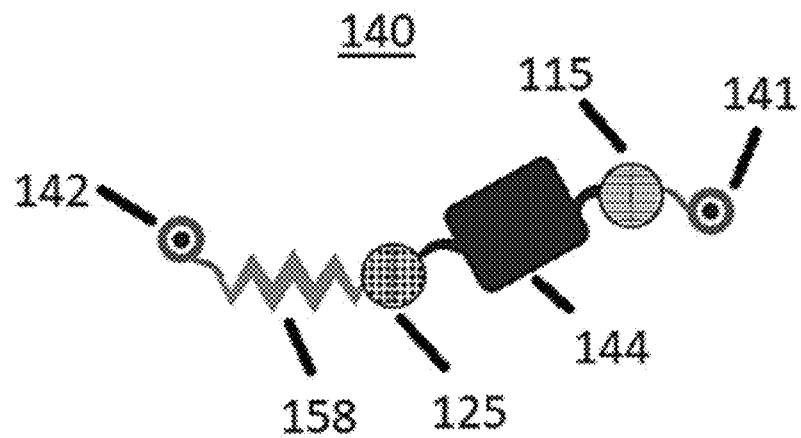
Figure 10D:
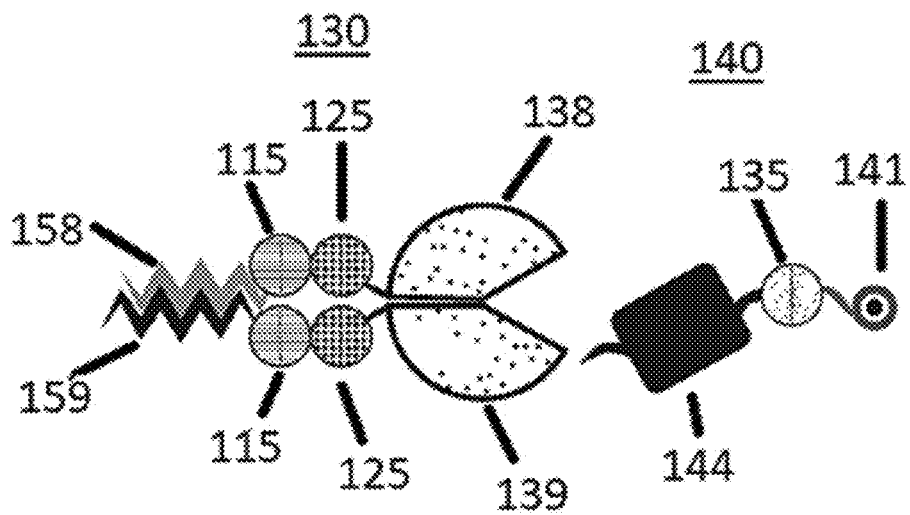
Figure 10E:
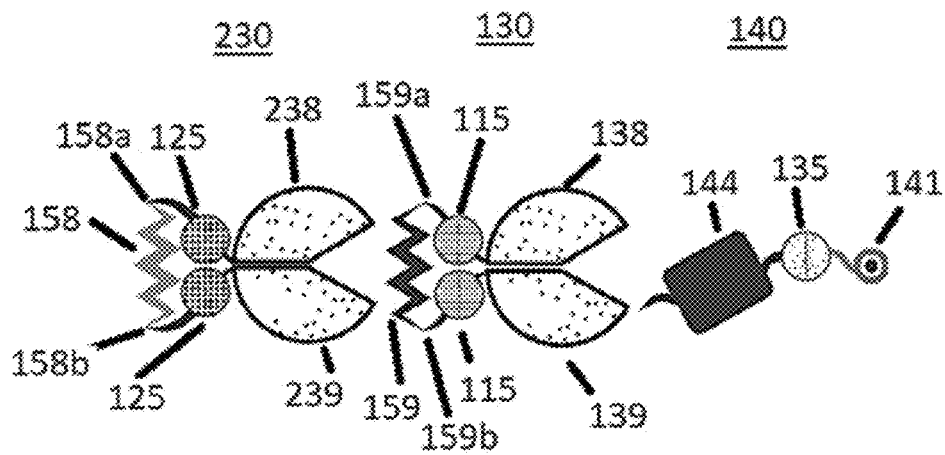
Figure 10F:
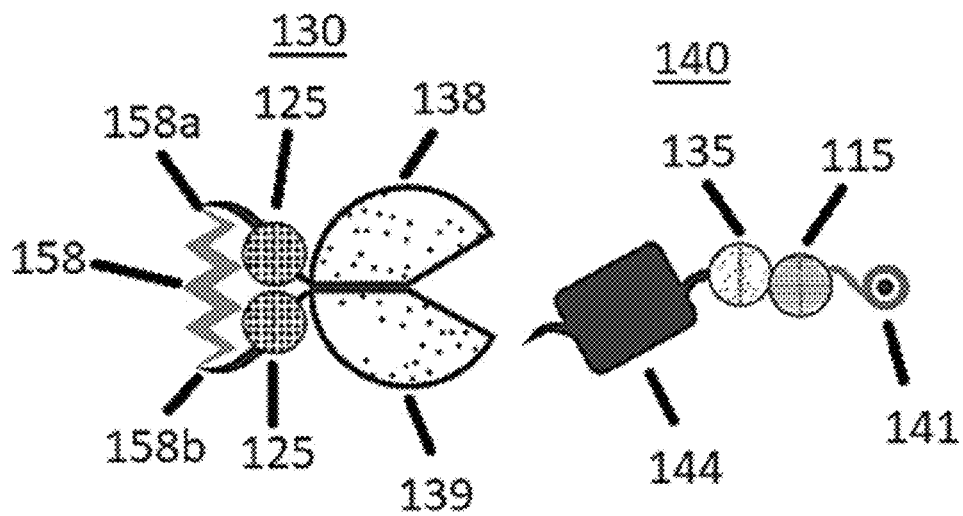
Figure 10G:
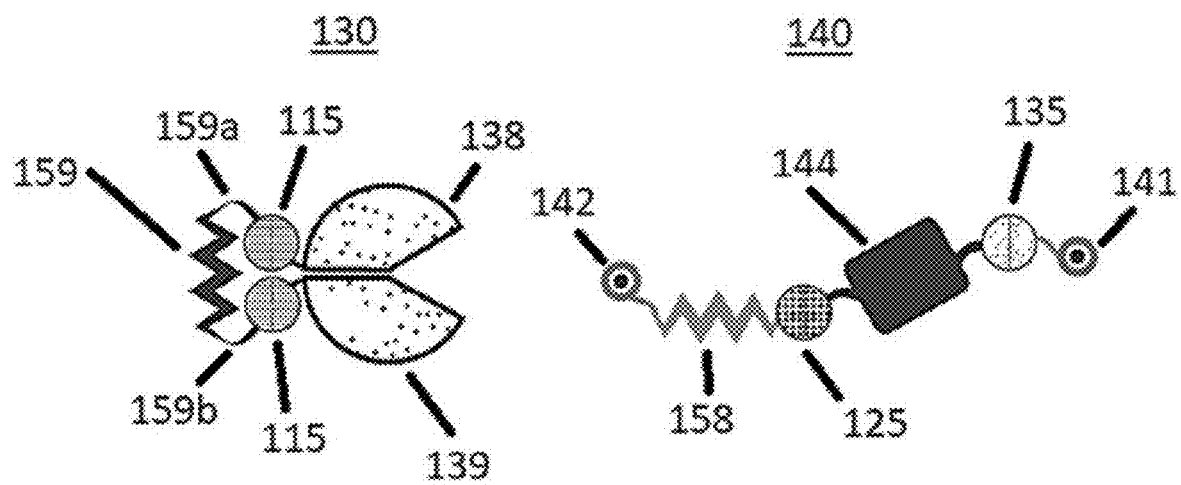
Figure 10H:
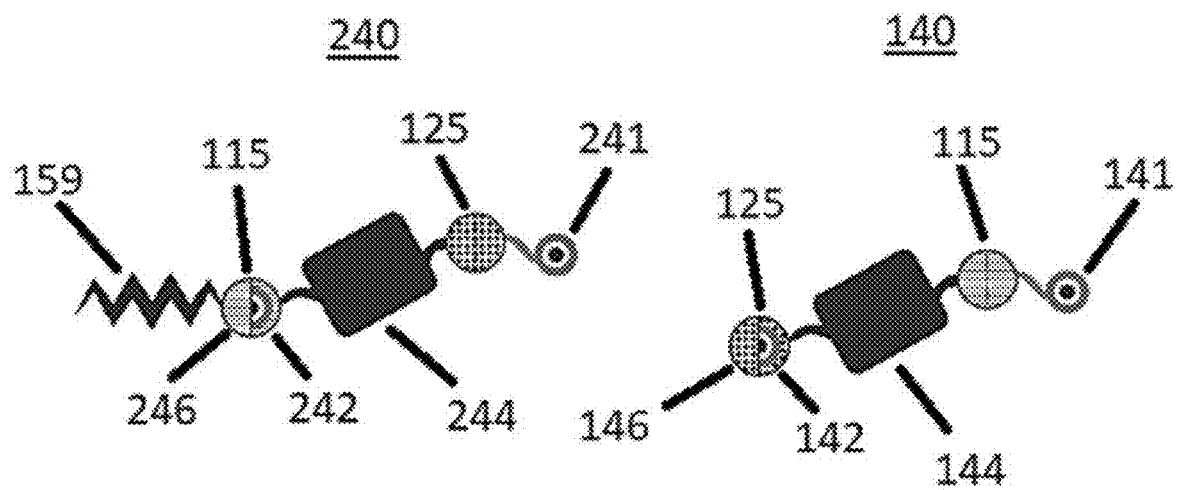
Figure 10I:
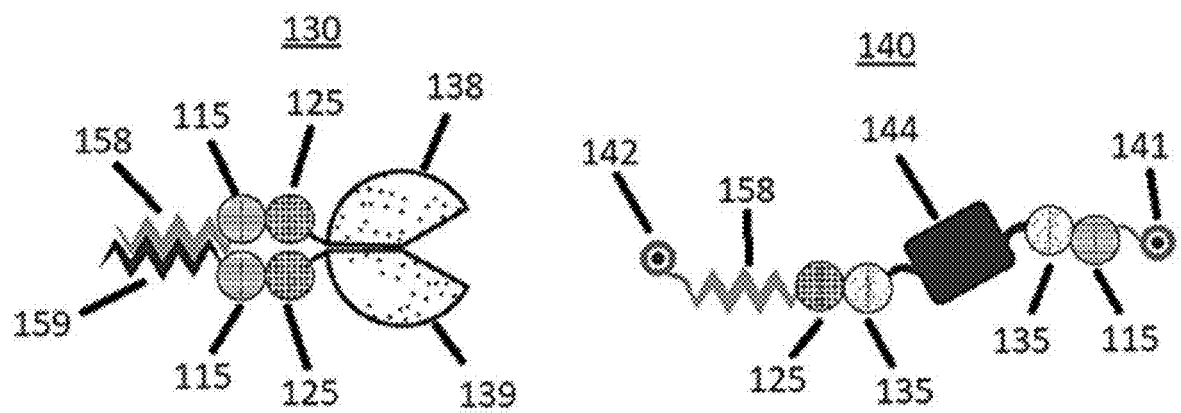

Some embodiments of the synthetic protein circuit include a target protein 140, such as the target protein shown in FIG. 8, including: a degron 141 of the target protein 140 that destabilizes the target protein 140 when present on the target protein 140 by enhancing degradation of the target protein 140, and a cut site 125 specific for the second protease 120, wherein the target protein 140 is configured to be stabilized or destabilized by cleavage of the cut site 125 specific for the second protease 210.

In some embodiments of the synthetic protein circuit, the second protease 120 includes a first cleavage domain 128 and a second part 129 of the cleavage domain, the first part 128 connecting to the cut site 115 specific for the first protease 110, and the second part 129 connecting to another cut site 115 specific for the first protease 110, the second protease's 120 two cut sites 115 specific for the first protease 110 each connecting to an association domain 158 of the second protease 120 such as a leucine zipper. In some embodiments, the second protease's 120 two cut sites 115 specific for the first protease 110 each connect to a separate association domain 158, 159 of the second protease 120, wherein the second protease 120 is active when the separate association domains 158, 159 bind together, and wherein the second protease 120 is configured to be deactivated by cleavage of either of its two cut sites 115 specific for the first protease 110. In some embodiments, one of the second protease's 120 association domains 158, 159 includes a complementary association domain 159 such as leucine zipper that is complementary or antiparallel to the other association domain 158 of the second protease 120. In some embodiments, such as in the example shown in FIGS. 9A-9B, the second protease's 120 two cut sites 115 specific for the first protease 110 each connect to a single association domain 159 of the second protease 120, and wherein the second protease 120 is configured to be deactivated by cleavage of either of its two cut sites 115 specific for the first protease 110.

In some embodiments of the synthetic protein circuit, the first protease 110 includes an association domain 158 of the first protease 110 that binds to a complementary association domain 159 of the second protease 120, thereby allowing or enhancing the first protease's 110 ability to cleave a cut site 115 specific to the first protease 110 on the second protease 120.

Some embodiments of the synthetic protein circuit include a third, fourth, fifth, sixth, seventh, eighth, ninth and/or tenth protease 130, each protease 110, 120, 130 including a cut site specific to at least one of the proteases 110, 120, 130, and wherein each protease 110, 120, 130 is configured to be destabilized or deactivated by cleavage of its cut site.

Some embodiments of the synthetic protein circuit include a protease activatable target protein. In some embodiments, such as in the examples shown in FIGS. 7A and 8, the target protein's 140 cut site 125 specific to the second protease 120 includes a first part 125a of the cut site 125 of the target protein 140 and a second part 125b of the cut site 125 of the target protein 140, the first part 125a of the cut site 125 of the target protein 140 connecting to a domain or motif 144 of the target protein, and the second part 125b of the cut site 125 of the target protein 140 connecting to the degron 141 of the target protein 140, and wherein the target protein 140 is stabilized by cleavage of its cut site 125 specific for the second protease 120.

Figure 7C:
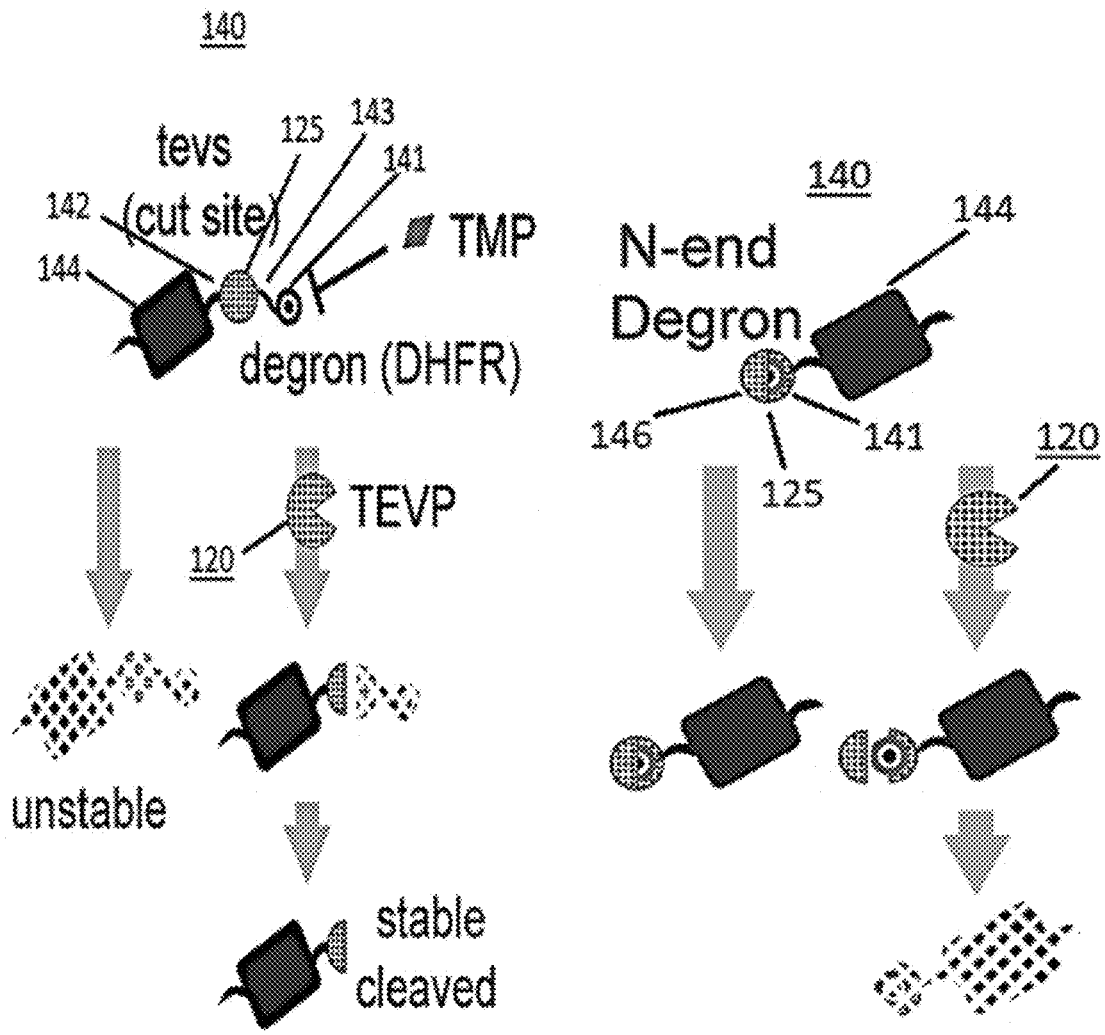
FIG. 7C depicts a legend for the symbols shown in FIGS. 7A-7B in other figures.
Figure 7C:
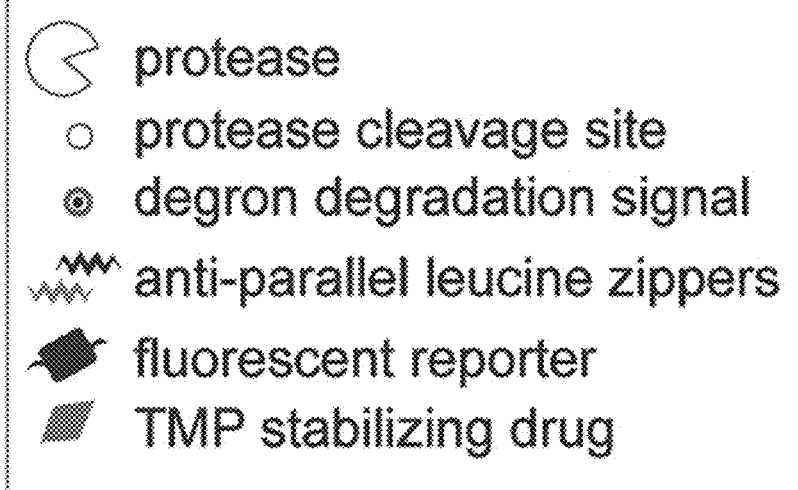

In some embodiments of the synthetic protein circuit, such as is shown in FIG. 7B, the degron 141 of the target protein 140 includes a masking peptide 146 that connects to the degron 141 of the target protein 140 and blocks cleavage of the target protein's 140 cut site 125 specific for the second protease 120, wherein the masking peptide 146 of the degron 141 of the target protein 140 includes the target protein's 140 cut site 125 specific for the second protease 120, and wherein the target protein 140 is configured to be destabilized by cleavage of its cut site 125 specific for the second protease 120, wherein cleavage of the target protein's 140 cut site 125 specific for the second protease 125 uncovers the target protein's 140 degron 141.

In some embodiments of the synthetic protein circuit, the target protein 140 consists of or comprises a protease, a reporter protein, a fluorescent protein, a scaffold, an actuator protein, a transcriptional regulator, or a signaling protein.

In some embodiments of the system, the synthetic protein circuit includes a logic gate such as a logic gate shown in FIGS. 10A-10I. In some embodiments, the system includes a synthetic protein circuit, including: a first protease 110, optionally including an association domain 158 of the first protease 110; a second protease 120, optionally including a complementary association domain 159 of the second protease 120; and a target protein 140 including a degron 141 of the target protein 140 that destabilizes the target protein 140 when present on the target protein 140 by enhancing degradation of the target protein 140; wherein the target protein 140 is configured to interact with the first protease 110, the second protease 120, a third protease 130 and/or a fourth protease 240 to form an OR, AND, NOR, NAND, IMPLY, NIMPLY, XOR or XNOR logic gate.

In some embodiments, the synthetic protein circuit includes an OR logic gate. In some embodiments, the target protein 140 further includes a cut site 115 specific for the first protease 110 and a cut site 125 specific for the second protease 120 between the degron 141 of the target protein 140 and a part 144 of the target protein 140, and wherein the target protein 140 is stabilized by cleavage of either of its cut sites 115, 125.

In some embodiments, the synthetic protein circuit includes an AND logic gate. In some embodiments, the target protein 140 further includes a cut site 115 of the target protein 140 specific for the first protease 110 between the degron 141 of the target protein 140 and a part 144 of the target protein 140, and a cut site 125 specific for the second protease 120 connected to another degron 142 of the target protein 140 and an optional association domain 158 of the target protein 140, and wherein the target protein 140 is stabilized by cleavage of both of its cut sites 115, 125.

In some embodiments, the synthetic protein circuit includes a NOR logic gate. In some embodiments, the synthetic protein circuit includes a third protease 130 including: a cut site 115 specific for the first protease 110, a cut site 125 specific for the second protease 120, and an optional association domain 158 of the third protease 130, wherein the third protease 130 is configured to be deactivated by cleavage of either of its cut sites 115, 125; and wherein the target protein 140 includes a cut site 135 specific for the third protease 130 between the degron 141 of the target protein 140 and a part 144 of the target protein 140, wherein the target protein 140 is stabilized by cleavage of its cut site 135 specific for the third protease 130. In some embodiments, the third protease 130 further includes a first domain 138 of the third protease 130 and a second domain 139 of the third protease 130; wherein the first domain 138 of the third protease 130 includes the third protease's 130 cut sites 115, 125 specific for the first and second proteases 110, 120 and the optional association domain 158 of the third protease 130; wherein the second domain 139 the third protease 130 includes another cut site 115 specific for the first protease 110, another cut site 125 specific for the second protease 120, and an optional complementary association domain 159 the third protease 130; and wherein the third protease 130 is configured to be deactivated by cleavage of any of its cut sites 115, 115, 125, 125.

In some embodiments, the synthetic protein circuit includes a NAND logic gate. In some embodiments, the synthetic protein circuit includes a third protease 130 including a cut site 115 specific for the first protease 110, and configured to be deactivated by cleavage of its cut site 115; and a fourth protease 230 including a cut site 125 specific for the second protease 120, and configured to be deactivated by cleavage of its cut site 125; wherein the target protein 140 includes a cut site 135 specific for the third and fourth proteases 130, 230 between the degron 141 of the target protein 140 and a part 144 of the target protein 140, wherein the target protein 140 is stabilized by cleavage of its cut site 135. In some embodiments, the third protease 130 further includes a first domain 138 of the third protease 130, a second domain 139 of the third protease 130, and an optional complementary association domain 159 of the third protease 130; wherein the first domain 138 of the third protease 130 includes the cut site 115 specific for the first protease 110; wherein the second domain 139 of the third protease 130 includes another cut site 115 specific for the first protease 110; wherein the complementary association domain 159 the third protease 130 optionally includes two parts 159*a*, 159*b* of the third protease 130, each part 159*a*, 159*b* the third protease 130 connected to one of the third protease's 130 cut sites 115, 115; and wherein the third protease 130 is configured to be deactivated by cleavage of either of its cut sites 115, 115.

In some embodiments of the synthetic protein circuit, the fourth protease 230 protease further includes a first domain 238 of the fourth protease 230, a second domain 239 of the fourth protease 230, and an optional association domain 158 of the fourth protease 230; wherein the first domain 238 of the fourth protease 230 includes the cut site 125 specific for the second protease 120; wherein the second domain 239 of the fourth protease 230 includes another cut site 125 specific for the second protease 120; wherein the association domain 158 of the fourth protease 230 optionally includes two parts 158*a*, 158*b*, each part 158*a*, 158*b* connected to one of the fourth protease's 230 cut sites 125, 125; and wherein the fourth protease 230 is configured to be deactivated by cleavage of either of its cut sites 125, 125.

In some embodiments, the synthetic protein circuit comprises an IMPLY logic gate. In some embodiments, the synthetic protein circuit includes a third protease 130 including a cut site 125 specific for the second protease 120, and configured to be deactivated by cleavage of its cut site 125; wherein the target protein 140 further includes a cut site 115 specific for the first protease 110 and a cut site 135 specific for the third protease 130 between the degron 141 of the target protein 140 and a part 144 of the target protein 140, and wherein the target protein 140 is stabilized by cleavage of either cut sites 115, 135. In some embodiments, the third protease 130 further includes a first domain 138, a second domain 139, and an optional association domain 158; wherein the first domain 138 of the third protease 130 includes the third protease's cut site 125 specific for the second protease 120; wherein the second domain 139 of the third protease 130 includes another cut site 125 specific for the second protease 120; wherein the association domain 158 of the third protease 130 optionally includes two parts 158*a*, 158*b* of the third protease 130, each part 158*a*, 158*b* of the third protease 130 connected to one of the third protease's 130 cut sites 125, 125; and wherein the third protease 130 is configured to be deactivated by cleavage of either of its cut sites 125, 125.

In some embodiments, the synthetic protein circuit comprises a NIMPLY logic gate. In some embodiments, the synthetic protein circuit includes a third protease 130 including a cut site 115 specific for the first protease 110, and configured to be deactivated by cleavage of its cut site 115; wherein the target protein 140 further includes a cut site 135 specific for the third protease 130 between the degron 141 and a part 144 of the target protein, and a cut site 125 specific for the second protease 120 connected to another degron 142 of the target protein 140 and an optional association domain 158 of the target protein 140, and wherein the target protein 140 is stabilized by cleavage of both of its cut sites 125, 135. In some embodiments, the third protease 130 further includes a first domain 138 of the third protease 130, a second domain 139 of the third protease 130, and an optional complementary association domain 159 of the third protease 130; wherein the first domain 138 of the third protease 130 includes the cut site 115 specific for the first protease 110; wherein the second domain 139 of the third protease 130 includes another cut site 115 specific for the first protease 110; wherein the complementary association domain 159 of the third protease 130 optionally includes two parts 159*a*, 159*b* of the third protease 130, each part 159*a*, 159*b* of the third protease 130 connected to one of the third protease's 130 cut sites 115, 115; and wherein the third protease 130 is configured to be deactivated by cleavage of either of its cut sites 115, 115.

In some embodiments, the synthetic protein circuit comprises an XOR logic gate. In some embodiments, the synthetic protein circuit includes a second target 240 protein including a degron 241 of the second target 240 protein that destabilizes the second target protein 240 when present on the second target protein 240; wherein the target protein 140 further includes a cut site 115 specific for the first protease 110 between its degron 141 and a part 144 of the target protein 140, another degron 142 of the target protein 140, and a cut site 125 specific for the second protease 120 connected to the other degron 142 of the target protein 140, wherein the target protein 140 is destabilized by its first degron 141 unless its cut site 115 specific for the first protease 110 is cleaved by the first protease 110, and wherein the target protein 140 is destabilized by cleavage of its cut site 125 specific for the second protease 120; and wherein the second target protein 240 further includes a cut site 125 specific for the second protease 120 between its degron 241 and the part 244 of the second target protein 240, another degron 242 of the second target protein 240, and a cut site 115 specific for the first protease 110 connected to the other degron 242 of the second target protein 240, wherein the second target protein 240 is destabilized by its first degron 241 unless its cut site 125 specific for the second protease 120 is cleaved by the second protease 120, and wherein the second target protein 240 is destabilized by cleavage of its cut site 115 specific for the first protease 110. In some embodiments, the second target protein 240 further includes a complementary association domain 159 of the second target protein 240 connected at or near the other degron 242 of the second target protein 240 or the second target protein's 240 cut site 115 specific for the first protease 110. In some embodiments, the target protein's 140 other degron 142 includes a masking peptide 146 of the other degron 142 of the target protein 140 connected to the target protein's 140 other degron 142, wherein the masking peptide 146 of the other degron 142 of the target protein 140 prevents the target protein's 140 other degron 142 from destabilizing the target protein 140 when the masking peptide 146 of the other degron 142 of the target protein 140 is present on the target protein 140, wherein the masking peptide 146 of the other degron 142 of the target protein 140 is configured to be cleaved from the target protein 140 when the target protein's 140 cut site 125 specific for the second protease 120 is cleaved by the second protease 120, wherein the target protein 140 is configured to be destabilized by cleavage of its cut site 125 specific for the second protease 120, wherein cleavage of the target protein's 140 cut site 125 specific for the second protease 120 uncovers the target protein's 140 other degron 142 thereby destabilizing the target protein 140. In some embodiments, the second target protein's 240 other degron 242 includes a masking peptide 246 of the other degron 142 of the second target protein 240 connected to the second target protein's 240 other degron 242, wherein the masking peptide 246 of the other degron 142 of the second target protein 240 prevents the second target protein's 240 other degron 242 from destabilizing the second target protein 140 when the masking peptide 246 of the other degron 142 of the second target protein 240 is present on the second target protein 240, wherein the masking peptide 246 of the other degron 142 of the second target protein 240 is configured to be cleaved from the second target protein 240 when the second target protein's 240 cut site 115 specific for the first protease 110 is cleaved by the first protease 110, wherein the second target protein 240 is configured to be destabilized by cleavage of its cut site 115 specific for the first protease 110, wherein cleavage of the second target protein's 240 cut site 115 specific for the first protease 110 uncovers the second target protein's 240 other degron 242 thereby destabilizing the second target protein 240.

In some embodiments, the synthetic protein circuit comprises an XNOR logic gate. In some embodiments, the synthetic protein circuit includes a third protease 130 including a cut site 115 specific for the first protease 110, a cut site 125 specific for the second protease 120, and one or more optional association domains 158, 159 of the third protease 130, wherein the third protease 130 is configured to be deactivated by cleavage of either of its cut sites 115, 125; wherein the target protein 140 further includes a second degron 142 of the target protein, a cut site 115 specific for the first protease 110, a cut site 125 specific for the second protease 120, and two cut sites 135, 135 specific for the third protease 130, and wherein the target protein 140 is stabilized by cleavage of: its cut site 115 specific for the first protease 110 and its cut site 125 specific for the second protease 120, or both of its cut sites 135, 135 specific for the third protease 130. Other combinations may also be included such as follows: 115 and the left 135, or 125 and the right 135.

In some embodiments of the synthetic protein circuit, the third protease 130 further includes a first domain 138 of the third protease 130 and a second domain 139 of the third protease 130; wherein the first domain 138 of the third protease 130 includes the cut sites 115, 125 specific for the first and second proteases 110, 120 and the optional association domain 158 of the third protease 130; wherein the second domain 139 of the third protease 130 includes another cut site 115 specific for the first protease 110, another cut site 125 specific for the second protease 120, and an optional complementary association domain 159 of the third protease 130; and wherein the third protease 130 is configured to be deactivated by cleavage of any of its cut sites 115, 115, 125, 125. In some embodiments, the target protein's 140 cut site 115 specific for the first protease 110 and one of the target protein's 140 two cut sites 135, 135 specific for the third protease 130 separate the target protein's 140 first degron 141 from a part 144 of the target protein 140; and wherein the target protein's 140 cut site 125 specific for the second protease 120 the other of the two cut sites 135 specific for the third protease 130, and the association domain 159 of the target protein 140 separate the target protein's 140 second degron 142 from the part 144 of the target protein 140.

Figure 11A:
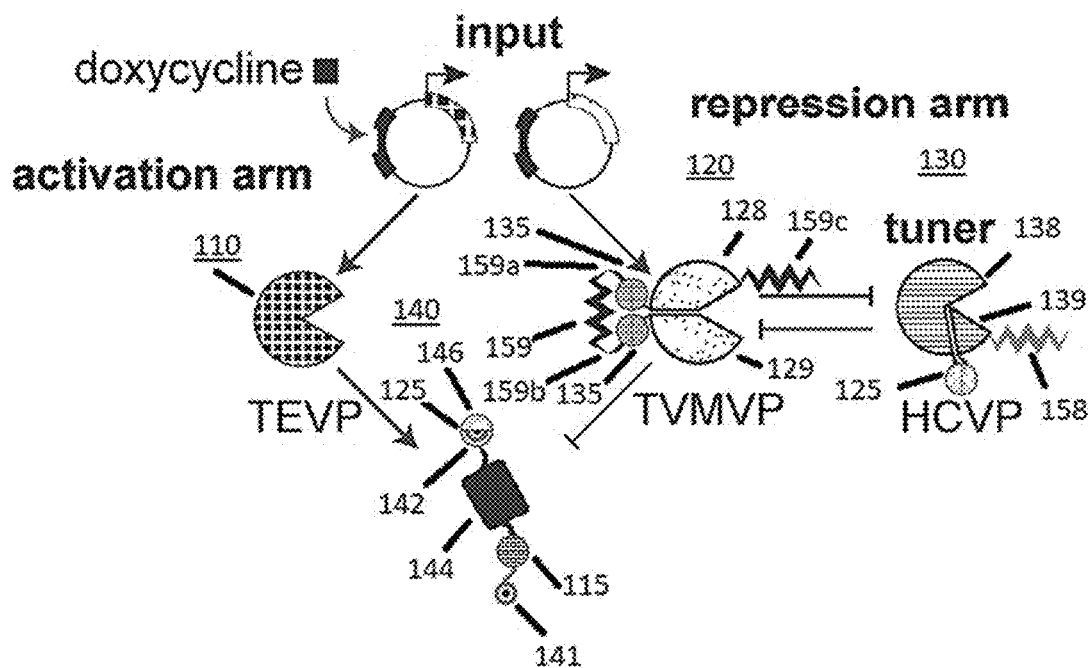
FIGS. 11A-11B show non-limiting exemplary schematic illustrations of bandpass filtering and pulse generation circuits according to some embodiments.
Figure 11B:
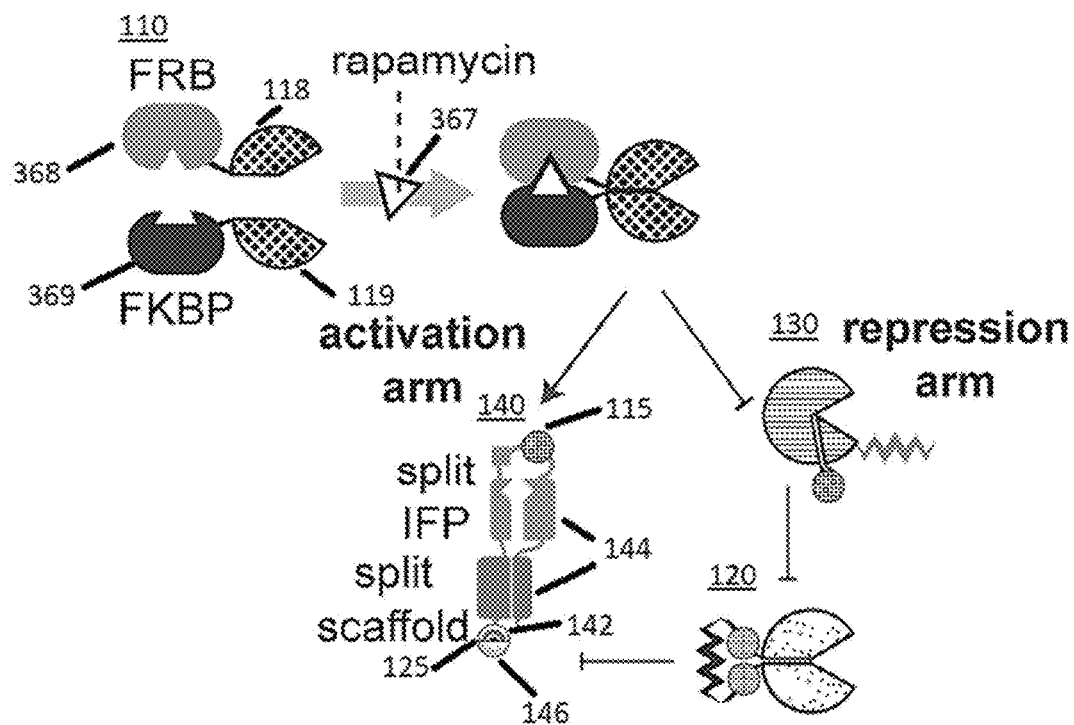

In some embodiments of the synthetic protein circuit, the system or synthetic protein circuit comprises a bandpass circuit or filter, or an adaptive pulse circuit such as is shown, exemplified, or described in FIGS. 11A-11B. In some embodiments of the bandpass circuit or filter, a second protease 120 is tuned by a third protease 130. In other embodiments, a first protease is tuned by a second, third, or fourth protease. In accordance with some embodiments, any protease may tune another protease. Some embodiments include a system such as a synthetic protein circuit, including: a first protease 110; a second protease 120; and target proteins 140 each including: a first degron 141 of the target protein 140 that destabilizes the target protein 140 when present on the target protein 140 by enhancing degradation of the target protein 140, a cut site 115 specific for the first protease 110 between the degron 141 of the target protein 140 and a part 144 of the target protein 140, wherein the target protein 140 is configured to be stabilized by cleavage of its cut site 115 specific for the first protease 110, and a cut site 125 specific for the second protease 120 connected to another degron 142 of the target protein 140, wherein the target protein 140 is configured to be destabilized by cleavage of the cut site 125 specific for the second protease 120 regardless of whether the first degron 141 of the target protein 140 is present on the target protein 140. In some embodiments, the other degron 142 of each target protein 140 includes a conditional N-end degron.

Some embodiments include a third protease 130 including a cut site 125 specific for the second protease 120, wherein the third protease 130 is configured to be deactivated by cleavage of its cut site 125 specific for the second protease 120; and wherein the second protease 120 includes a cut site 135 specific for the third protease 130, wherein the second protease 120 is configured to be deactivated by cleavage of its cut site 135 specific for the third protease 130.

In some embodiments of the synthetic protein circuit, the second protease 120 further includes a first domain 128 of the second protease 120, a second domain 129 of the second protease 120, a first complementary association domain 159, and an optional second complementary association domain 159*c* of the second protease 120 connected to the first or second domain 128, 129 of the second protease 120; wherein the first domain 128 of the second protease 120 includes the cut site 135 specific for the third protease 130; wherein the second domain 129 of the second protease 120 includes another cut site 135 specific for the third protease 130; wherein the first complementary association domain 159 of the second protease 120 optionally includes two parts 159*a*, 159*b* of the complementary association domain 159 of the second protease 120, each part 159*a*, 159*b* of the complementary association domain 159 of the second protease 120 connecting to one of the second protease's 120 cut sites 135 specific for the third protease 130; and wherein the second protease 120 is configured to be deactivated by cleavage of either of its cut sites 135, 135.

In some embodiments of the synthetic protein circuit, the third protease 130 further includes an optional association domain 159 of the third protease 130, and wherein cleavage of the third protease's 130 cut site 125 by the second protease 120 removes at least part of a cleavage domain 139 of the third protease 130, thereby deactivating the third protease 130.

In some embodiments of the synthetic protein circuit, the stability of the target proteins 140 includes an analog behavior that is dependent on a concentration of the first protease 110, wherein a higher concentration of the first protease 110 has a greater stabilizing effect on the target proteins 140 than a lower concentration of the first protease 110. In some embodiments, the stability of the target proteins 140 includes an analog behavior that is dependent on a concentration of the second protease 120, wherein a higher concentration of the second protease 120 has a greater destabilizing effect on the target proteins 140 than a lower concentration of the second protease 120. In some embodiments, the concentration of the second protease 120 is decreased by a higher concentration of the third protease 130 as compared to a lower concentration of the third protease 130, or by a higher amount of a nucleic acid encoding the third protease 130 as compared to a lower amount of a nucleic acid encoding the third protease 130. In some embodiments, the analog behavior of the target protein 140 that is dependent on a concentration of the second protease 120 is more sharp and/or includes a greater threshold for destabilizing the target protein 140 at a higher concentration of the third protease 130 as compared to a lower concentration of the third protease 130, or at a higher amount of a nucleic acid encoding the third protease 130 as compared to a lower amount of a nucleic acid encoding the third protease 130.

In some embodiments of the synthetic protein circuit, the first protease 110 further includes a first domain 118 of the first protease 110 and a second domain 119 of the first protease 110; wherein the first domain 118 of the first protease 110 connects to a first conditional dimerization domain 368 of the first protease 110; wherein the second domain 119 of the first protease 110 connects to a second conditional dimerization domain 369 of the first protease 110; wherein the first and second conditional dimerization domains 368, 369 of the first protease 110 are configured to dimerize with each other upon binding a dimerizing agent 367. In some embodiments, the conditional dimerization domains 368, 369 of the first protease 110 each include one of an FK506 binding protein (FKBP), GyrB, GAI, Snap-tag, eDHFR, BCL-xL, CalcineurinA (CNA), CyP-Fas, FRB domain of mTOR, GID1, HaloTag, TIR1, auxin inducible degron, and/or Fab (AZ1). In some embodiments, the dimerizing agent 367 includes FK1012, FK506, FKCsA, Rapamycin, Coumermycin, Gibberellin, HaXS, TMP-HTag, auxin, or ABT-737. In some embodiments, at least one of the conditional dimerization domains 368, 369 and/or the dimerizing agent 367 include a leucine zipper motif or a complementary leucine zipper motif, a scaffold protein or a fragment thereof, a scaffold-binding motif, an antibody, an epitope, tetratricopeptide repeat, a tetracopeptide repeat-binding motif, a G-protein-coupled receptor, a β-arrestin, and/or a G protein.

Some embodiments relate to a system such as a synthetic protein circuit, including: a first protease 110; a second protease 120; and a target protein 140 including: one or more cut sites specific for a first, second, and/or third protease, and a degron of the target protein 140 configured to stabilize or destabilize the target protein 140 based on its configuration with one or more of the target protein's 140 cut sites specific for the first, second, and/or third proteases. In some embodiments, the first protease 110 further includes a first domain 118 of the first protease 110 and a second domain 119 of the first protease 110; wherein the first domain 118 of the first protease 110 connects to a first conditional dimerization domain 368 of the first protease 110; wherein the second domain 119 of the first protease 110 connects to a second conditional dimerization domain 369 of the first protease 110; wherein the first and second conditional dimerization domains 368, 369 of the first protease 110 are configured to dimerize with each other upon binding a dimerizing agent 367.

In some embodiments of the system or synthetic protein circuit, the analog behavior of the target protein 140 includes a bandpass behavior.

Beyond Boolean logic, analog signal filtering can allow for many cellular functions, such as the ability to selectively respond to specific input concentration ranges. The incoherent feed-forward loop (IFFL) motif, in which an input both activates and inhibits the same target, provides a simple implementation for this function. To parallel IFFL, in some embodiments an activating arm, in which TEVP removes a C-terminal degron, is combined with a repressing arm, in which TVMVP reveals a destabilizing N-end tyrosine (FIG. 11A). In some embodiments, to tune the position and sharpness of the bandpass, a positive feedback loop is introduced based on reciprocal inhibition between HCVP and TVMVP on the repression arm, such that the amount of HCVP expression sets a threshold for TVMVP activity (FIG. 11A).

In some embodiments of the synthetic protein circuits provided herein comprise temporal signal processing, such as adaptation to a change in input. For example, some of the synthetic protein circuits provided herein comprise IFFL, containing the 3-step cascade (FIGS. 9C-9D) to introduce a delay in the repressing arm relative to that of the activating arm. To enable sudden induction, some embodiments comprise rapamycin-induced TEVP used for the logic gates. In some embodiments, to facilitate dynamic readout of circuit output in individual cells, a fluorescent protein is provided (e.g., far-red fluorescent protein (IFP)) that is synthesized in a non-fluorescent state, but can be post-translationally switched on by TEVP. In some embodiments, a conditional N-end degron enables repression by TVMVP (FIG. 11B).

In some embodiments, the entire pulse-generation circuit is encoded as a single open reading frame, with interleaved 2A "self-cleaving" peptides to separate distinct protein components.

Methods

Some embodiments relate to a method, including: providing a reaction solution with a protease or compound protease as described herein, and an enzyme such as a protease or compound protease or an enzyme described herein; and subjecting the reaction solution to a condition that allows the enzyme to cleave the cut site 515 of the compound protease 520. In some embodiments, providing the reaction solution comprises providing a reaction solution in vitro. Some embodiments include providing the reaction solution to a cell or to cells.

Some embodiments relate to a method of activating a signaling pathway in a cell, including providing to the cell a synthetic protein circuit or a nucleic acid encoding the synthetic protein circuit, the synthetic protein circuit including: a protease 410 including a first part 418 of the protease 410 and a second part 419 of the protease 410, the first part 418 of the protease 410 connecting to a signaling protein 471, and the second part 419 of the protease 410 connecting to a binding protein 472 that binds to an activated form of the signaling protein 471, wherein the first part 418 and the second part 419 are configured to form an active protease 410 when the binding protein 472 binds to the activated form of the signaling protein 471; and an effector protein 480 including a cut site 415 specific for the protease 410, wherein the effector protein 480 configured to be activated by cleavage of its cut site 415 specific for the protease 410. In some embodiments, the synthetic protein circuit further includes a second protease 120 that inactivates the first protease 410 and/or the effector protein 480. In some embodiments, the signaling pathway includes a cell death pathway. In some embodiments, the signaling protein 471 includes a signal transduction protein such as Ras or a fragment thereof. In some embodiments, the binding protein 472 includes Raf or a fragment thereof such as a Ras-binding domain (RBD). In some embodiments, the effector protein 480 includes a protease, a cell death protein such as a caspase, an immunomodulatory, or a specific antigen. In some embodiments, the method includes the use of a mutual inhibition motif such as a bandpass filter or adaptive pulse circuit as described herein.

EXAMPLES

Some aspects of the embodiments discussed above are disclosed in further detail in the following examples, which are not in any way intended to limit the scope of the present disclosure.

Example 1

Figure 2A:
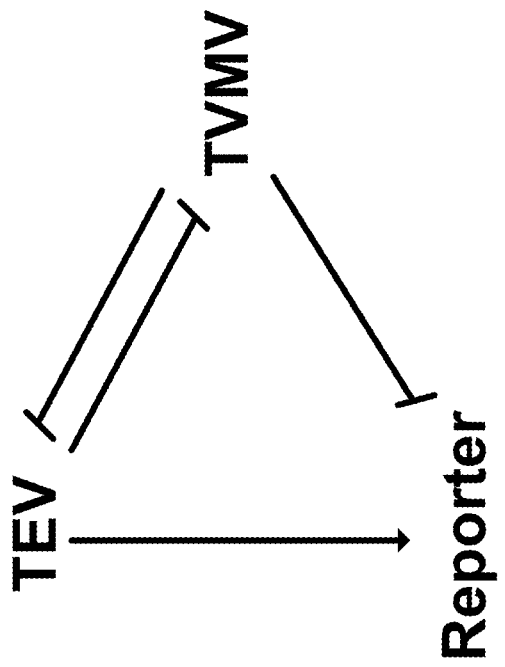
FIG. 2A shows a non-limiting exemplary schematic illustration of 'core' and 'full' synthetic protein circuits provided herein.
Figure 2A:
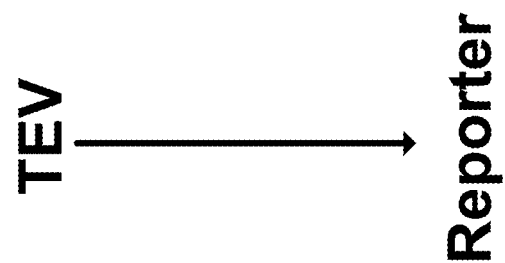
Figure 2B:
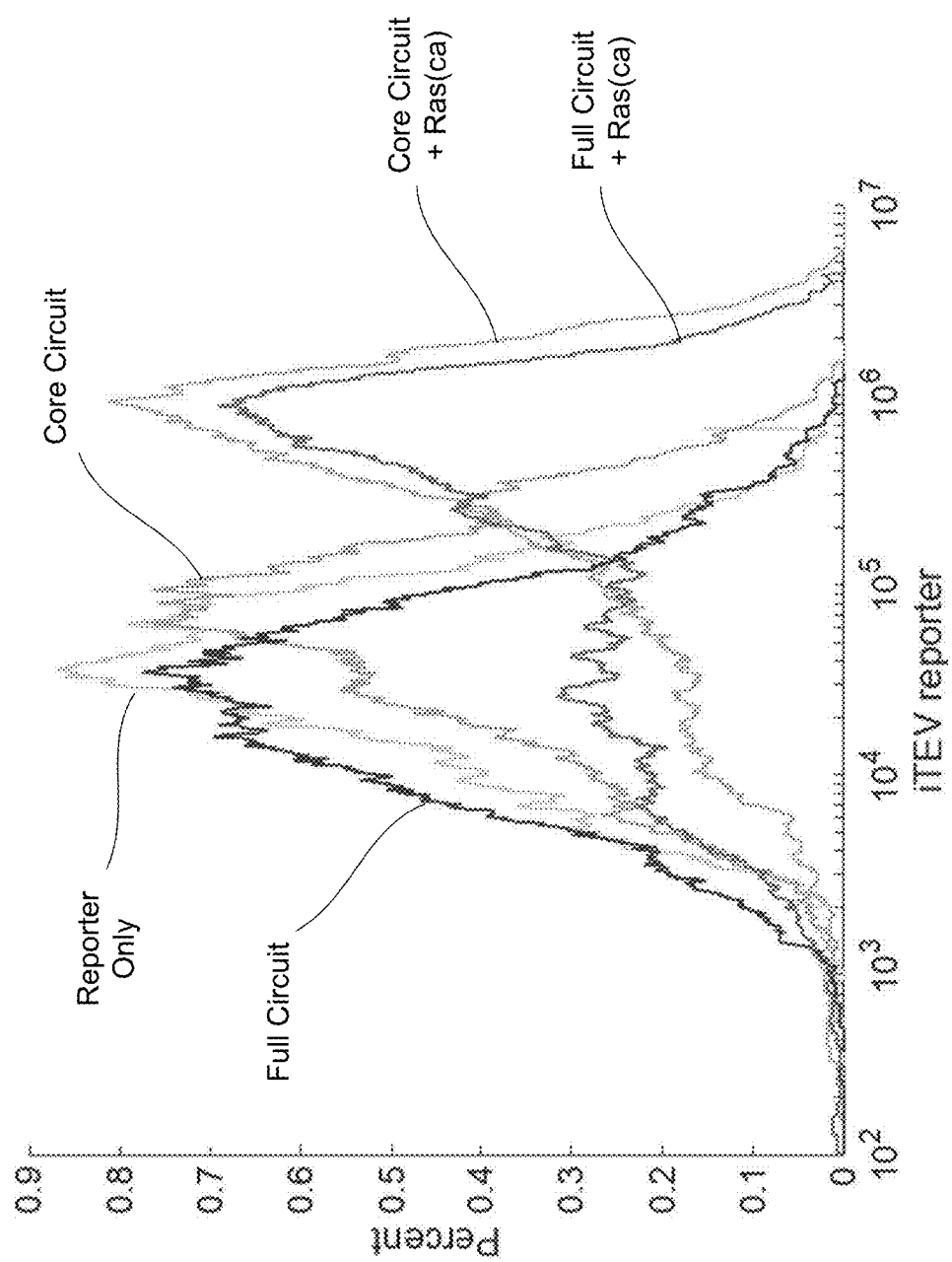
FIGS. 2B-2C depict data related to detection of active Ras signaling with synthetic protein circuits provided herein.
Figure 2C:
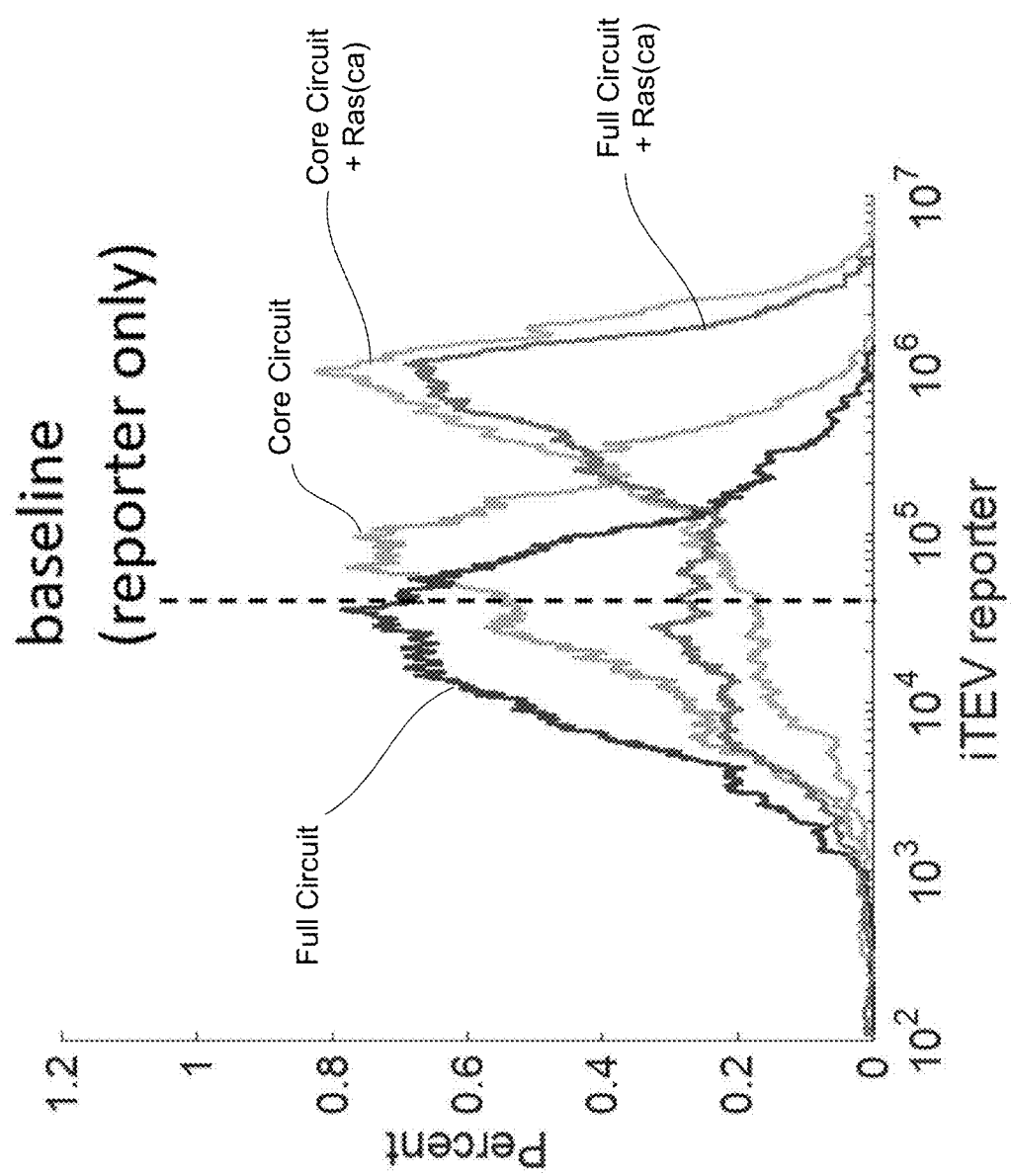
Figure 3A:
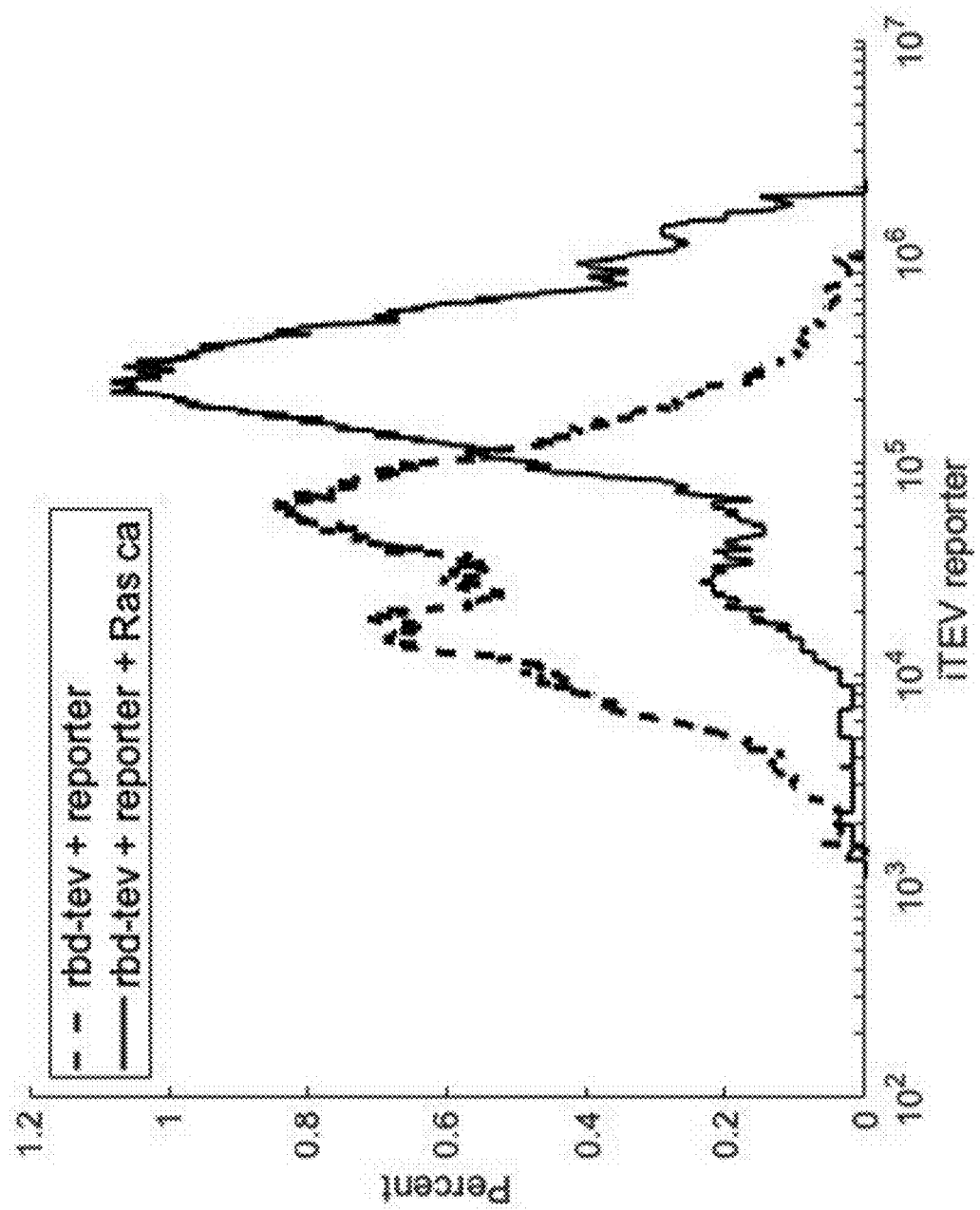
Figure 3B:
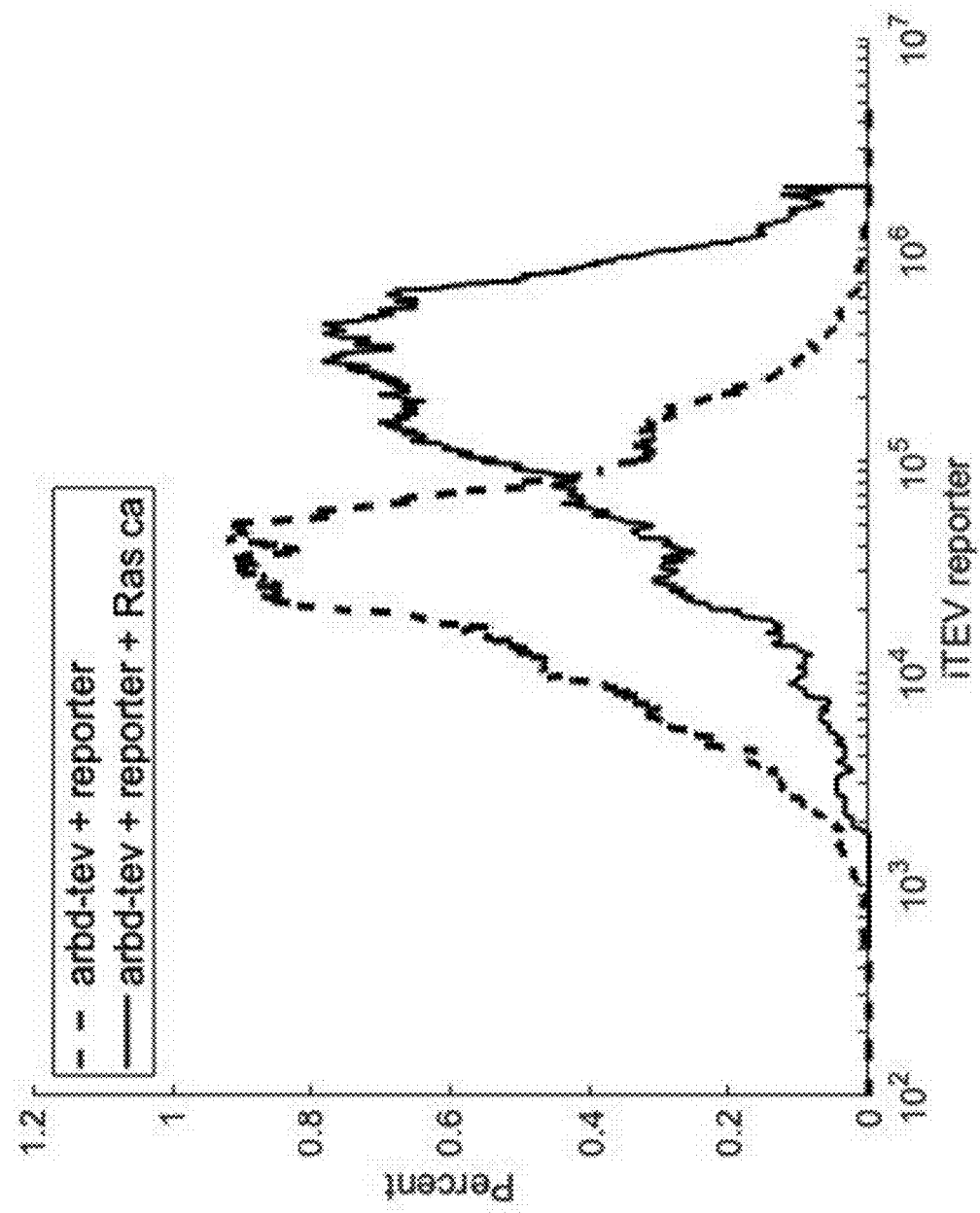
Figure 3C:
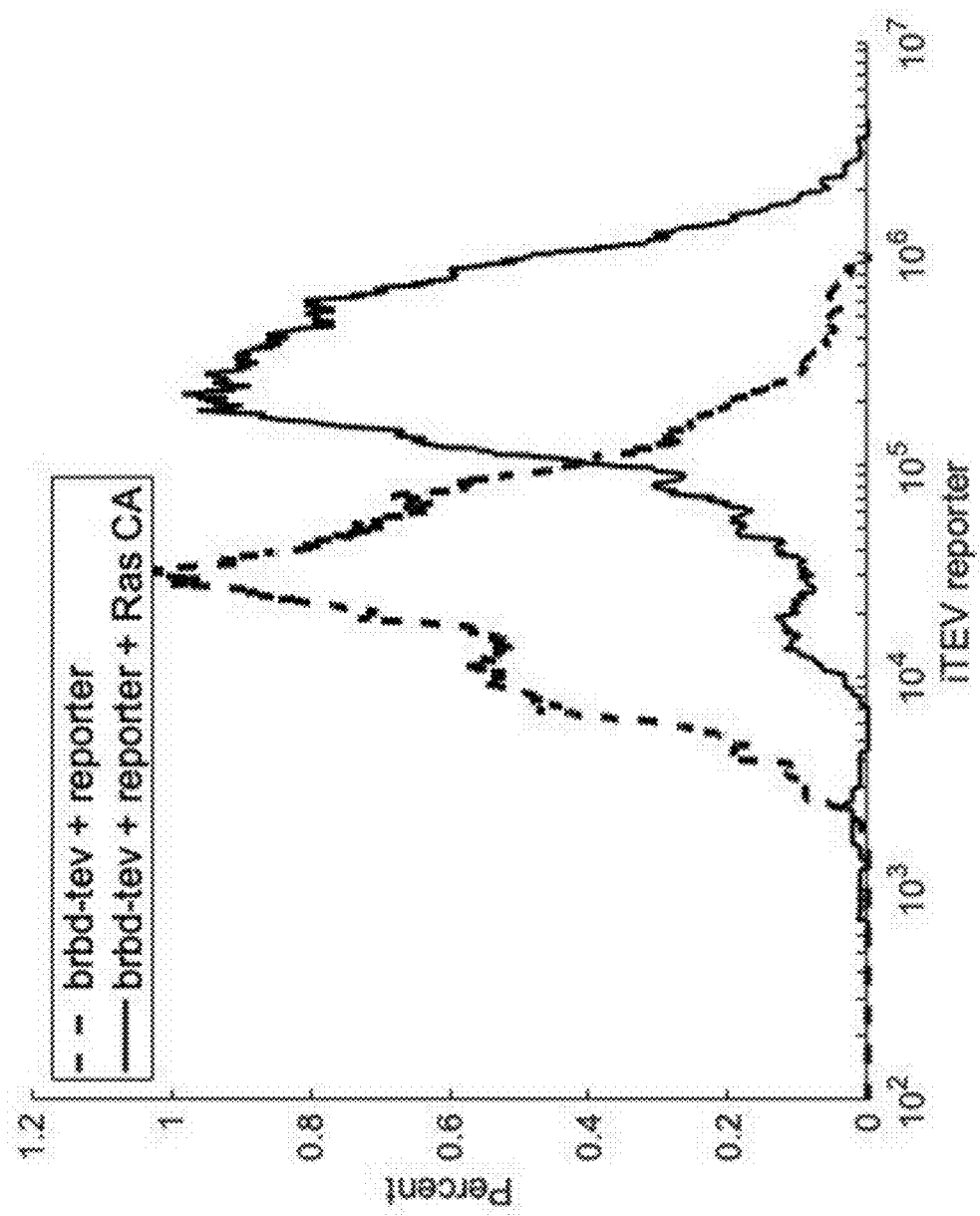
Figure 3D:
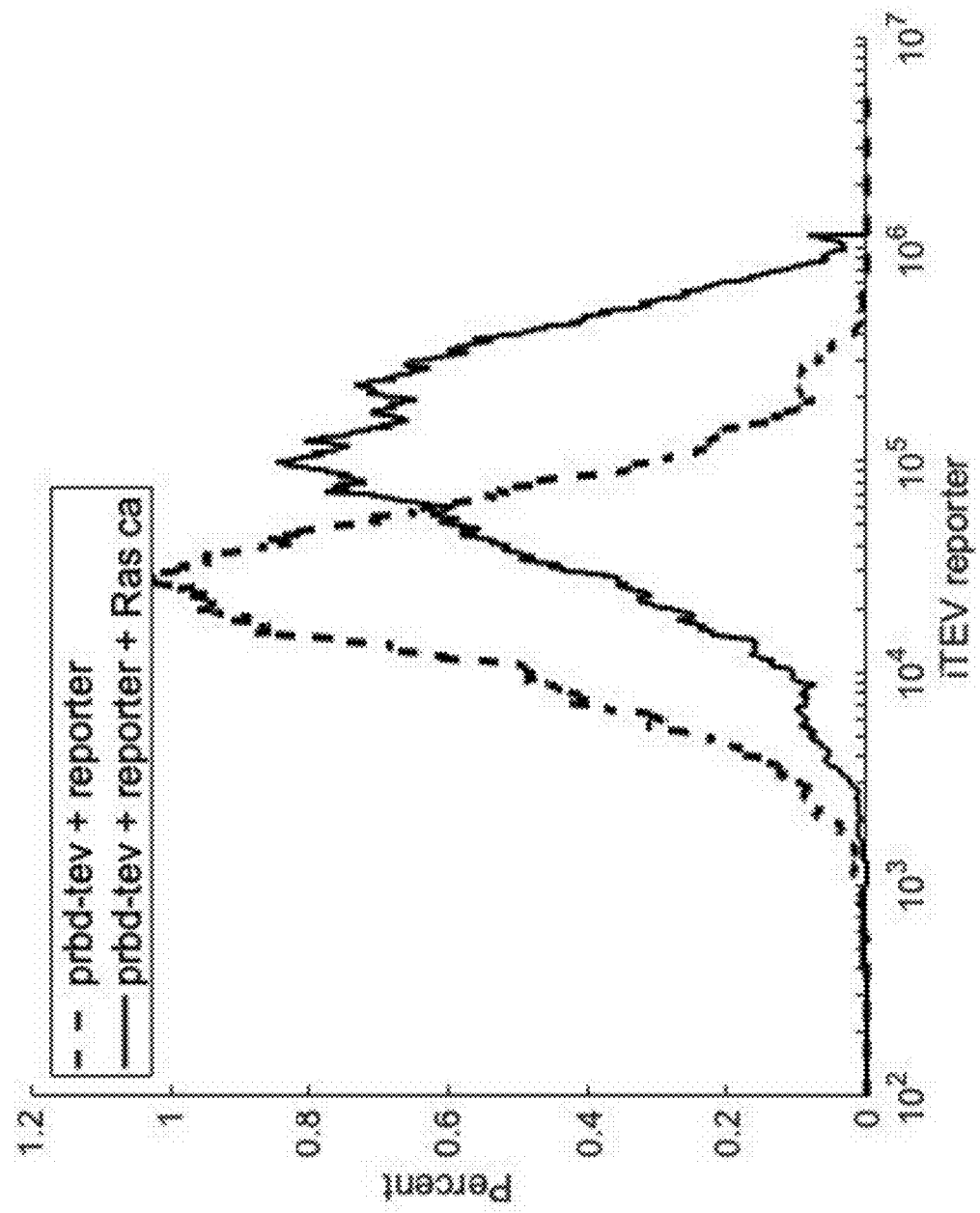

Detecting Active Ras Through Membrane Translocation and Reconstitution of Split TEV Protease This example demonstrates a synthetic protein circuit employing the enrichment through translocation design concept described herein. In this example, the synthetic circuit exploits the recruitment of Ras binding domain (RBD) to the plasma membrane by active Ras. An RBD domain was fused to each half of split TEV protease. Increased Ras activity causes both TEV components to translocate to the plasma membrane, increasing the local concentration of both protease halves, and thereby increasing the concentration of reconstituted protease through weak residual affinity between the halves. A membrane-localized fluorescent marker (TEV protease-activated fluorescence reporter) and constitutively active Ras (Ras ca) were used to validate this scheme in a circuit shown in FIG. 2A. The relationship between the components of the core and full circuits tested in this experiment are depicted in FIG. 2A. Flow cytometry analysis of the TEV protease-activated reporter (FIGS. 2B-2C) demonstrated the detection of active Ras (constitutively active Ras was compared to wildtype Ras) through membrane translocation and reconstitution of split TEV protease. Furthermore, as compared to the core circuit, the full circuit showed an improved signal-to-baseline ratio, thereby validating the "response sharpening" design provided herein. The design concept was further validated by employing additional human homologs of RBD, including arbd (derived from A-Raf), brbd (derived from B-Raf), prbd (derived from PI3Kgamma) and rrbd (derived from Ral-GDS), demonstrating that the design can be generalized within the same type of reactions (FIGS. 3A-3E).

Example 2

Figure 4A:
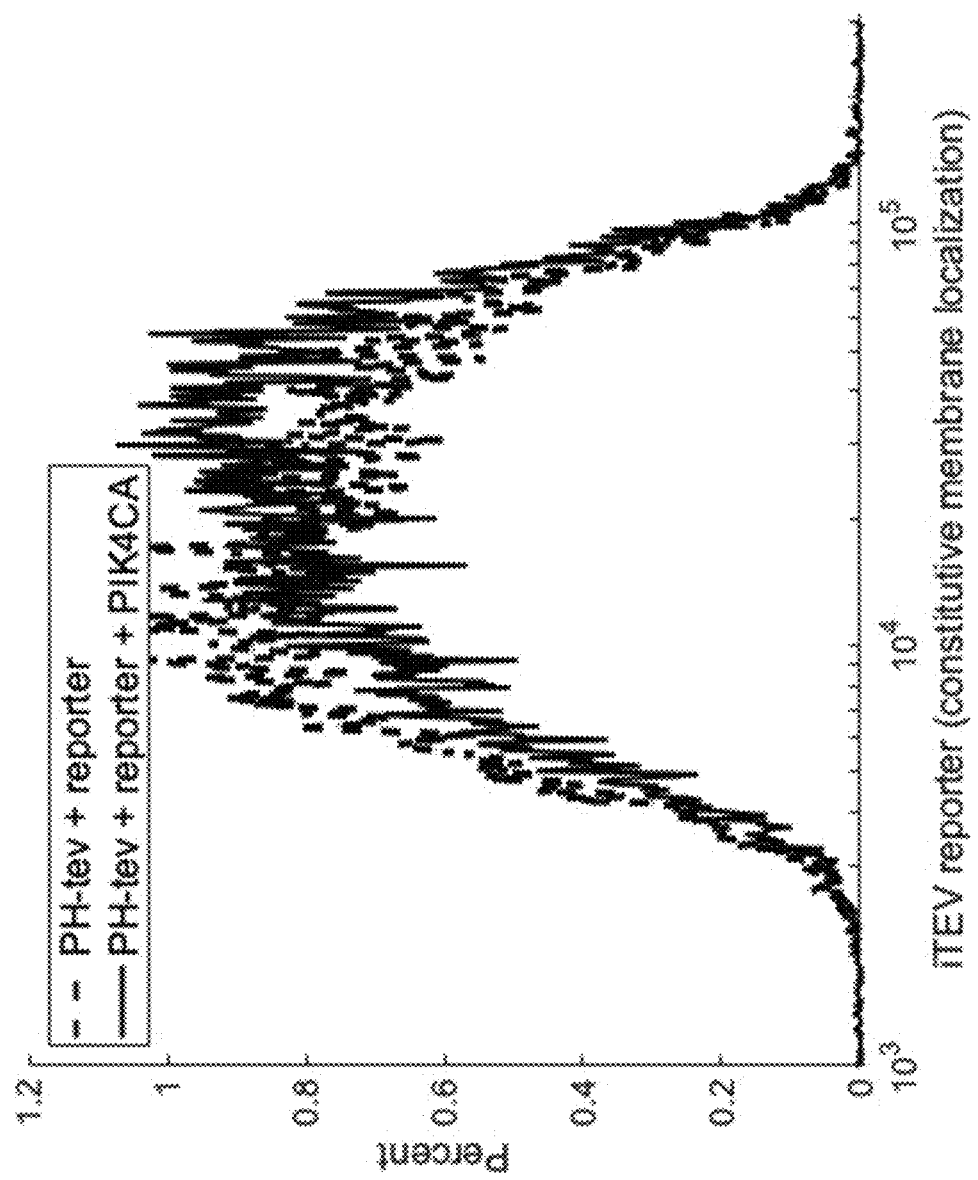
FIGS. 4A-4B depicts data related to detection of active PI3 kinase signaling with synthetic protein circuits provided herein.
Figure 4B:
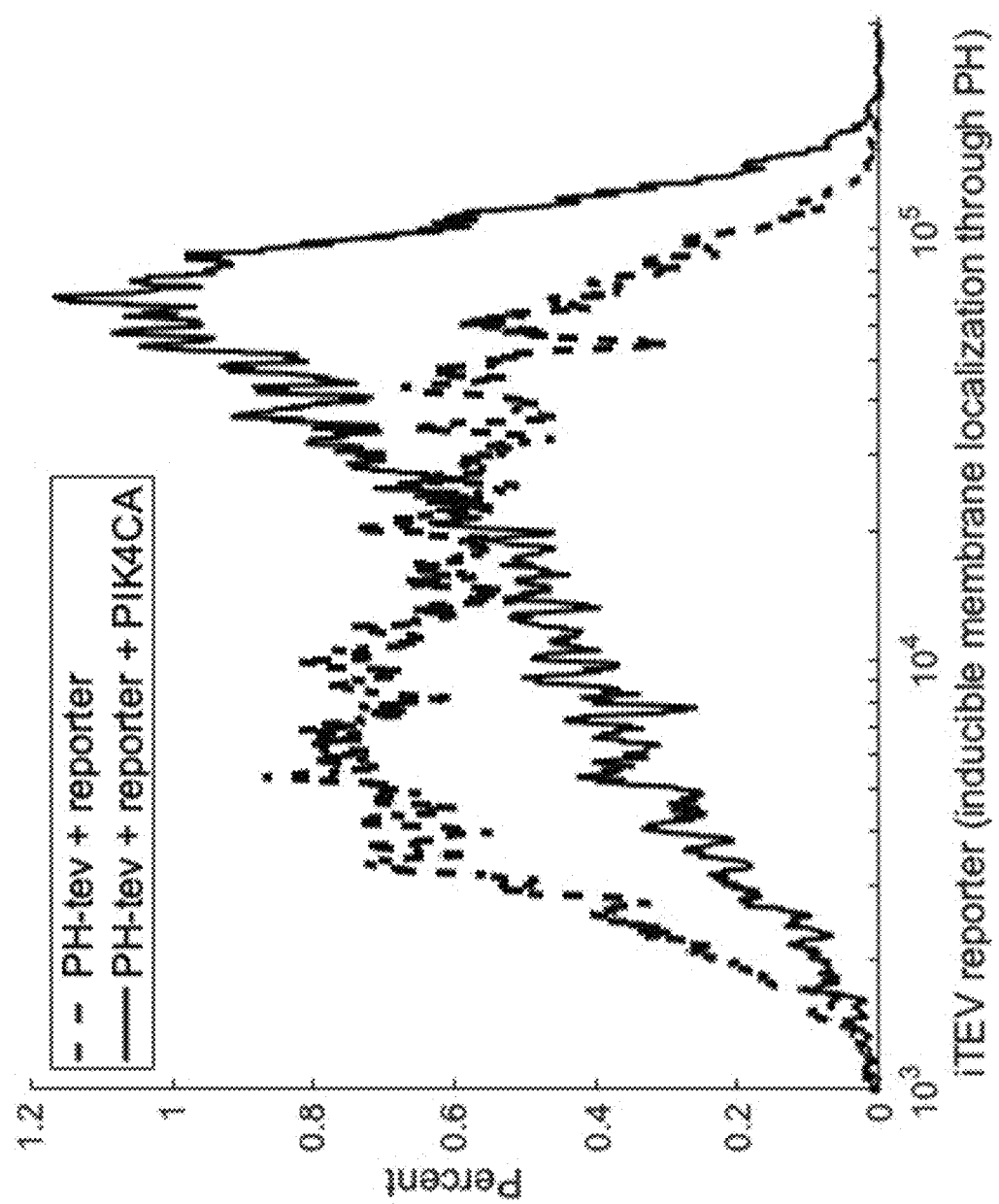

Phosphatidylinositol 3-Phosphate Enriches PH Domain at the Membrane and Reconstitutes TEV Protease This example provides further validation for the enrichment through translocation synthetic protein circuit design concept described herein by showing that it can detect non-protein signal transducers as well as proteinaceous signal transducers. A synthetic protein circuit was designed similar in principle to Example 1, only instead of active Ras, the input is PI3P (produced by transfecting a PI3 kinase) and instead of instead of RBD, the signal transducer binding domain is PH. Versions of the circuit with constitutive localization of the iTEV reporter to the membrane (FIG. 4A), as well as a circuit where the reporter is conditionally translocated to the membrane through a PH domain (FIG. 4B) were validated. An improvement in the dynamic range was observed when the reporter was conditionally translocated to the membrane through the PH domain (FIG. 4B). These results demonstrate that the design principle provided herein can be generalized to different pathways and different type of interactions.

Enumerated Embodiments

1. A synthetic protein circuit, comprising:
  a first polypeptide comprising a first signal transducer binding domain and a first part of a first protease domain, wherein the first signal transducer binding domain is capable of binding a first signal transducer to form a first signal transducer-bound polypeptide;
  a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and
  an effector protein comprising a first cut site the first protease in the first protease active state is capable of cutting.

2. The synthetic protein circuit of claim 1, wherein the first signal transducer binding domain of the first polypeptide and the second signal transducer binding domain of the second polypeptide are identical.

3. The synthetic protein circuit of any one of claims 1-2, wherein the first transducer and the second transducer are identical.

4. The synthetic protein circuit of any one of claims 1-3, wherein the first signal transducer, the second signal transducer, or both, are capable of being localized at the association location.

5. The synthetic protein circuit of any one of claims 1-4, wherein the first signal transducer when in a first signal transducer active state, the second signal transducer when in a second signal transducer active state, or both, are capable of being localized at the association location.

6. The synthetic protein circuit of any one of claims 1-5, wherein the first signal transducer when in a first inactive state, the second signal transducer when in a second inactive state, or both, are capable of being localized at the association location.

7. The synthetic protein circuit of any one of claims 1-6, wherein the first signal transducer binding domain of the first polypeptide is capable of binding to the first signal transducer, wherein the second signal transducer binding domain of the second polypeptide is capable of binding to the second signal transducer, or both.

8. The synthetic protein circuit of any one of claims 1-7, wherein the first signal transducer binding domain of the first polypeptide is capable of binding to the first signal transducer in a first signal transducer active state, wherein the second signal transducer binding domain of the second polypeptide is capable of binding to the second signal transducer in a second signal transducer active state, or both.

9. The synthetic protein circuit of any one of claims 1-8, wherein the first signal transducer binding domain of the first polypeptide is capable of binding to the first signal transducer in a first inactive state, wherein the second signal transducer binding domain of the second polypeptide is capable of binding to the second signal transducer in a second inactive state, or both.

10. The synthetic protein circuit of any one of claims 1-9, wherein the signal transducer binding domain of the first polypeptide is capable of binding the first signal transducer to form the first signal transducer-bound polypeptide at the association location, wherein the signal transducer binding domain of the first polypeptide is capable of binding the first signal transducer to form the first signal transducer-bound polypeptide at the association location, or both.

11. The synthetic protein circuit of any one of claims 1-10, wherein the signal transducer binding domain of the first polypeptide is capable of binding the first signal transducer to form the first signal transducer-bound polypeptide at a first cellular location other than the association location, wherein the signal transducer binding domain of the first polypeptide is capable of binding the first signal transducer to form the first signal transducer-bound polypeptide at a second cellular location other than the association location, or both.

12. The synthetic protein circuit of claim 11, wherein the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

13. The synthetic protein circuit of any one of claims 1-12, wherein the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

14. The synthetic protein circuit of any one of claims 1-13, wherein a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state.

15. The synthetic protein circuit of any one of claims 1-14, wherein a first concentration of the first protease in the first protease active state is at least two-fold higher at the association location as compared a cellular location other than the association location when the first signal transducer is in a first signal transducer active state and/or when the second signal transducer is in a second signal transducer active state.

16. The synthetic protein circuit of any one of claims 1-15, wherein the first part of the first protease domain and the second part of the first protease domain have the weak association affinity when the first signal transducer is in a first signal transducer inactive state and/or the second signal transducer inactive state.

17. The synthetic protein circuit of any one of claims 1-16, wherein the first part of the first protease domain and the second part of the first protease domain are incapable of associating to form the first protease in the first protease active state when the first signal transducer is in a first signal transducer inactive state and/or the second signal transducer is in a second signal transducer inactive state.

18. The synthetic protein circuit of any one of claims 1-17, wherein a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state.

19. The synthetic protein circuit of any one of claims 1-18, wherein a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state.

20. The synthetic protein circuit of any one of claims 1-19, wherein the first part of the first protease domain and the second part of the first protease domain are capable of associating with each other to form the first protease in the first protease active state at a threshold first polypeptide concentration and a threshold second polypeptide concentration at the association location.

21. The synthetic protein circuit of claim 20, wherein the threshold first polypeptide concentration and the threshold second polypeptide concentration at the association location are reached at a threshold signal transducer activation level of the signal transducer.

22. The synthetic protein circuit of any one of claims 1-21, wherein the effector protein changes from an effector inactive state to an effector active state when the first protease in the first protease active state cuts the first cut site of the effector.

23. The synthetic protein circuit of any one of claims 1-22, wherein a level of activation of the effector protein positively correlates with a first level of activation of the first signal transducer and/or a second level of activation of the second signal transducer.

24. The synthetic protein circuit of claim 23, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

25. The synthetic protein circuit of any one of claims 1-23, wherein the effector protein changes from an effector active state to an effector inactive state when the first protease in the first protease active state cuts the first cut site of the effector.

26. The synthetic protein circuit of any one of claims 1-23 and 25, wherein a level of activation of the effector protein negatively correlates with a first level of activation of the first signal transducer and/or a second level of activation of the second signal transducer.

27. The synthetic protein circuit of claim 26, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

28. The synthetic protein circuit of any one of claims 1-27, wherein the effector protein comprises a third signal transducer binding domain, and wherein the third signal transducer binding domain is capable of binding the first signal transducer and/or the second signal transducer.

29. The synthetic protein circuit of any one of claims 1-28, further comprising a repressor protein, wherein the repressor protein comprises a second protease.

30. The synthetic protein circuit of claim 29, wherein the second protease in a second protease active state is capable of cutting a first cut site of the first polypeptide and/or a second cut site of the second polypeptide.

31. The synthetic protein circuit of claim 30, wherein the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide.

32. The synthetic protein circuit of any one of claims 29-31, wherein the repressor protein comprises a cut site the first protease in the first protease active state is capable of cutting.

33. The synthetic protein circuit of claim 32, wherein the repressor protein is changed into a repressor destabilized state, a repressor delocalized state, and/or a repressor inactivate state after the first protease cuts the cut site of the repressor protein.

34. The synthetic protein circuit of any one of claims 29-32, wherein the effector protein comprises a second cut site the second protease in the second protease active state is capable of cutting.

35. The synthetic protein circuit of claim 34, wherein the effector protein is changed into a first effector destabilized state, a first effector delocalized state, and/or a first effector inactivate state after the second protease in the second protease active state cuts the cut site of the effector protein.

36. The synthetic protein circuit of any one of claims 29-35, wherein the effector protein comprises a degron, wherein the second protease in the second protease active state is capable of cutting the second cut site of the effector protein to expose the degron, and wherein the degron of the effector protein being exposed changes the effector protein to an effector destabilized state.

37. The synthetic protein circuit of claim 30, wherein the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide.

38. The synthetic protein circuit of any one of claims 29-30 and 37, wherein the repressor protein comprises a cut site the first protease in the first protease active state is capable of cutting.

39. The synthetic protein circuit of claim 38, wherein the repressor protein is changed into a repressor stabilized state, a repressor localized state, and/or a repressor activate state after the first protease in the first protease active state cuts the first cut site of the repressor protein.

40. The synthetic protein circuit of any one of claims 29-30 and 37-39, wherein the effector protein comprises a second cut site the second protease in the second protease active state is capable of cutting.

41. The synthetic protein circuit of claim 40, wherein the effector protein is changed into a first effector stabilized state, a first effector localized state, and/or a first effector activate state after the second protease in the second protease active state cuts the second cut site of the effector protein.

42. The synthetic protein circuit of any one of claims 29-30 and 37-41, wherein the effector protein comprises a degron, wherein the second protease in the second protease active state is capable of cutting the second cut site of the effector protein to hide the degron, and wherein the degron of the effector protein being hidden changes the effector protein to an effector stabilized state.

43. The synthetic protein circuit of any one of claims 1-42, wherein the effector protein is capable of changing a synthetic protein circuit component of the synthetic protein circuit to a synthetic protein circuit component active state.

44. The synthetic protein circuit of claim 43, wherein the effector protein comprises a third protease domain, and wherein the third protease domain is changes to an effector inactive state after the second protease in the second protease active state cuts the cute site of the effector protein.

45. The synthetic protein circuit of claim 43, wherein the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector.

46. The synthetic protein circuit of any one of claims 1-45, wherein the effector protein in an effector active state is capable of activating an endogenous signal transduction pathway.

47. The synthetic protein circuit of any one of claims 1-45, wherein the effector protein in an effector active state is capable of inactivating an endogenous signal transduction pathway.

48. The synthetic protein circuit of any one of claims 1-47, wherein the effector protein comprises Caspase-3, Caspase 7, Caspase-9, Caspase-8, Bax, Bid, Bad, Bak, BCL2L11, p53, PUMA, Diablo/SMAC, S-TRAIL, or any combination thereof.

49. The synthetic protein circuit of any one of claims 1-46, wherein the effector protein in an effector active state is capable of rendering a resident cell sensitive to a prodrug.

50. The synthetic protein circuit of claim 49, wherein the effector protein comprises cytosine deaminase and uracil phosphoribosyl transferase, and wherein the prodrug is 5-fluorocytosine (5-FC).

51. The synthetic protein circuit of claim 49, wherein the effector protein comprises thymidine kinase (TK), and the wherein the prodrug comprises ganciclovir.

52. The synthetic protein circuit of any one of claims 1-51, wherein two or more of the first signal transducer binding domain, the second signal transducer binding domain, and/or third signal transducer binding domain are identical.

53. The synthetic protein circuit of any one of claims 1-51, wherein two or more of the first signal transducer binding domain, the second signal transducer binding domain, and/or third signal transducer binding domain are different.

54. The synthetic protein circuit of any one of claims 1-53, wherein the first signal transducer binding domain, the second signal transducer binding domain, and/or third signal transducer binding domain each is capable of binding molecules of the first signal transducer and/or the second signal transducer.

55. The synthetic protein circuit of any one of claims 1-54, wherein the third signal transducer binding domain is capable of binding to a third signal transducer at the association location.

56. The synthetic protein circuit of claim 55, wherein the first signal transducer, the second signal transducer, and/or the third signal transducer belongs to a signal transduction pathway.

57. The synthetic protein circuit of any one of claims 1-56, wherein the first signal transducer binding domain, the second signal transducer binding domain, and/or the third signal transducer binding domain comprise a RAS binding domain (RBD) and/or RAS association domain (RAD).

58. The synthetic protein circuit of any one of claims 1-57, wherein the first signal transducer binding domain, the second signal transducer binding domain, and/or the third signal transducer binding domain comprises a lipid binding domain.

59. The synthetic protein circuit of claim 58, wherein the lipid binding domain comprises a Pleckstrin homology (PH) domain.

60. The synthetic protein circuit of any one of claims 1-58, wherein the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

61. The synthetic protein circuit of any one of claims 1-57, wherein the first signal transducer is capable of binding the first signal transducer binding domain and/or the second signal transducer is capable of binding the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof.

62. The synthetic protein circuit of any one of claims 1-61, wherein the first signal transducer, the second signal transducer, or both are endogenous proteins.

63. The synthetic protein circuit of any one of claims 1-62, wherein the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof.

64. The synthetic protein circuit of any one of claims 1-63, wherein the first signal transducer and/or the second signal transducer are capable of regulating cell survival, cell growth, cell proliferation, cell adhesion, cell migration, cell metabolism, cell morphology, cell differentiation, apoptosis, or any combination thereof.

65. The synthetic protein circuit of any one of claims 1-64, wherein the first signal transducer, the second signal transducer, or both comprise a RAS protein.

66. The synthetic protein circuit of claim 65, wherein the RAS protein is KRAS, NRHAS, HRAS, or any combination thereof.

67. The synthetic protein circuit of any one of claims 1-61, wherein the first signal transducer, the second signal transducer, or both are exogenous proteins.

68. The synthetic protein circuit of claim 67, wherein the synthetic protein circuit comprises the first signal transducer, the second signal transducer, or both.

69. The synthetic protein circuit of any one of claims 1-68, wherein the first signal transducer, the second signal transducer, or both comprise a lipid.

70. The synthetic protein circuit of claim 69, wherein the lipid comprises a phospholipid.

71. The synthetic protein circuit of claim 70, wherein the phospholipid is phosphatidylinositol 3-phosphate.

72. The synthetic protein circuit of any one of claims 1-71, wherein the synthetic protein circuit is capable of detecting an activity of the first signal transducer and an activity of the second signal transducer.

73. The synthetic protein circuit of any one of claims 1-72, wherein an activity of the effector protein correlates with an activity of the first signal transducer and/or an activity of the second signal transducer.

74. The synthetic protein circuit of any one of claims 1-73, wherein the synthetic protein circuit is capable of detecting activities of the first signal transducer and activities of the second signal transducer over a period of time.

75. The synthetic protein circuit of any one of claims 1-74, wherein activities of the effector protein correlate with activities of the first signal transducer and activities of the second signal transducer over a period of time.

76. The synthetic protein circuit of any one of claims 1-75, wherein the synthetic protein circuit is capable of detecting an aberrant signaling.

77. The synthetic protein circuit of claim 76, wherein aberrant signaling involves an active signal transducer.

78. The synthetic protein circuit of any one of claims 76-77, wherein the aberrant signaling involves an overactive signal transducer.

79. The synthetic protein circuit of any one of claims 76-78, wherein the aberrant signaling involves a constitutively active signal transducer over a period of time.

80. The synthetic protein circuit of any one of claims 1-79, wherein the synthetic protein circuit is capable of detecting an activity of a signal transducer activator and/or an activity of a signal transducer repressor.

81. The synthetic protein circuit of any one of claims 1-80, wherein the effector protein is capable of detecting an activity of a signal transducer activator and/or an activity of a signal transducer repressor.

82. The synthetic protein circuit of any one of claims 80-81, wherein the synthetic protein circuit comprises one or more circuit components that are capable of increasing a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor.

83. The synthetic protein circuit of any one of claims 80-82, wherein the synthetic protein circuit comprises one or more circuit components that are capable of increasing a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

84. The synthetic protein circuit of any one of claims 80-83, wherein the aberrant signaling involves an active signal transducer repressor and an active signal transducer.

85. The synthetic protein circuit of any one of claims 80-84, wherein the aberrant signaling involves an inactive signal transducer activator and an active signal transducer.

86. The synthetic protein circuit of any one of claims 80-85, wherein the aberrant signaling involves an inactive signal transducer.

87. The synthetic protein circuit of any one of claims 80-86, wherein the aberrant signaling involves an underactive signal transducer.

88. The synthetic protein circuit of any one of claims 80-87, wherein the aberrant signaling involves a constitutively inactive signal transducer over a period of time.

89. The synthetic protein circuit of any one of claims 80-88, wherein the aberrant signaling involves an inactive signal transducer repressor and an inactive signal transducer.

90. The synthetic protein circuit of any one of claims 80-89, wherein the aberrant signaling involves an active signal transducer activator and an inactive signal transducer.

91. The synthetic protein circuit of any one of claims 80-90, wherein the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

92. The synthetic protein circuit of any one of claims 80-91, wherein the synthetic protein circuit is capable of directly or indirectly inducing cell death in the presence of the aberrant signaling.

93. The synthetic protein circuit of any one of claims 80-92, wherein the effector protein is capable of directly or indirectly inducing cell death in the presence of aberrant signaling.

94. The synthetic protein circuit of any one of claims 1-93, wherein the synthetic protein circuit is capable of directly or indirectly inducing cell death when a first level of activation of the first signal transducer is above a first signal transducer activation threshold and/or a second level of activation of the second signal transducer is below a second signal transducer activation threshold.

95. The synthetic protein circuit of any one of claims 1-94, wherein the effector protein is capable of directly or indirectly inducing cell death when a first level of activation of the first signal transducer is above a first signal transducer activation threshold and/or a second level of activation of the second signal transducer is below a second signal transducer activation threshold.

96. A method of treating a disease or disorder characterized by an aberrant signaling of one or more signal transducers comprising:
expressing a synthetic protein circuit in a cell of a subject in need thereof, the synthetic protein circuit comprising:
a first polypeptide comprising a first signal transducer binding domain and a first part of a first protease domain, wherein the first signal transducer binding domain is capable of binding a first signal transducer of the cell to form a first signal transducer-bound polypeptide;
a second polypeptide comprising a second signal transducer binding domain and a second part of the first protease domain, wherein the second signal transducer binding domain is capable of binding a second signal transducer of the cell to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and
an effector protein comprising a first cut site the first protease in the first protease active state is capable of cutting to change the effector protein to an effector active state, or an effector inactive state, which correlates with an aberrant signaling of the first signal transducer and/or the second signal transducer, and wherein the effector protein in the effector active state, or the effector inactive state, is capable of changing a state of the cell, thereby treating a disease or disorder characterized by the aberrant signaling of the first signal transducer and/or the second signal transducer.

97. The method of claim 96, wherein the first signal transducer binding domain of the first polypeptide and the second signal transducer binding domain of the second polypeptide are identical.

98. The method of any one of claims 96-97, wherein the first transducer and the second transducer are identical.

99. The method of any one of claims 96-98, wherein the first signal transducer, the second signal transducer, or both, localize at the association location.

100. The method of any one of claims 96-99, wherein the first signal transducer when in a first signal transducer active state, the second signal transducer when in a second signal transducer active state, or both, localize at the association location.

101. The method of any one of claims 96-100, wherein the first signal transducer when in a first inactive state, the second signal transducer when in a second inactive state, or both, localize at the association location.

102. The method of any one of claims 96-101, wherein the first signal transducer binding domain of the first polypeptide binds to the first signal transducer, wherein the second signal transducer binding domain of the second polypeptide binds to the second signal transducer, or both.

103. The method of any one of claims 96-102, wherein the first signal transducer binding domain of the first polypeptide binds to the first signal transducer in a first signal transducer active state, wherein the second signal transducer binding domain of the second polypeptide binds to the second signal transducer in a second signal transducer active state, or both.

104. The method of any one of claims 96-103, wherein the first signal transducer binding domain of the first polypeptide binds to the first signal transducer in a first inactive state, wherein the second signal transducer binding domain of the second polypeptide binds to the second signal transducer in a second inactive state, or both.

105. The method of any one of claims 96-104, wherein the signal transducer binding domain of the first polypeptide binds the first signal transducer to form the first signal transducer-bound polypeptide at the association location, wherein the signal transducer binding domain of the first polypeptide binds the first signal transducer to form the first signal transducer-bound polypeptide at the association location, or both.

106. The method of any one of claims 96-105, wherein the signal transducer binding domain of the first polypeptide binds the first signal transducer to form the first signal transducer-bound polypeptide at a first cellular location other than the association location, wherein the signal transducer binding domain of the first polypeptide binds the first signal transducer to form the first signal transducer-bound polypeptide at a second cellular location other than the association location, or both.

107. The method of claim 106, wherein the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

108. The method of any one of claims 96-107, wherein the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

109. The method of any one of claims 96-108, wherein a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state.

110. The method of any one of claims 96-109, wherein a first concentration of the first protease in the first protease active state is at least two-fold higher at the association location as compared a cellular location other than the association location when the first signal transducer is in a first signal transducer active state and/or when the second signal transducer is in a second signal transducer active state.

111. The method of any one of claims 96-110, wherein the first part of the first protease domain and the second part of the first protease domain have the weak association affinity when the first signal transducer is in a first signal transducer inactive state and/or the second signal transducer inactive state.

112. The method of any one of claims 96-111, wherein the first part of the first protease domain and the second part of the first protease domain are incapable of associating to form the first protease in the first protease active state when the first signal transducer is in a first signal transducer inactive state and/or the second signal transducer is in a second signal transducer inactive state.

113. The method of any one of claims 96-112, wherein a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state.

114. The method of any one of claims 96-113, wherein a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state.

115. The method of any one of claims 96-114, wherein the first part of the first protease domain and the second part of the first protease domain associate with each other to form the first protease in the first protease active state at a threshold first polypeptide concentration and a threshold second polypeptide concentration at the association location.

116. The method of claim 115, wherein the threshold first polypeptide concentration and the threshold second polypeptide concentration at the association location are reached at a threshold signal transducer activation level of the signal transducer.

117. The method of any one of claims 96-116, wherein the effector protein changes from an effector inactive state to an effector active state when the first protease in the first protease active state cuts the first cut site of the effector.

118. The method of any one of claims 96-117, wherein a level of activation of the effector protein positively correlates with a first level of activation of the first signal transducer and/or a second level of activation of the second signal transducer.

119. The method of claim 118, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

120. The method of any one of claims 96-119, wherein the effector protein changes from an effector active state to an effector inactive state when the first protease in the first protease active state cuts the first cut site of the effector.

121. The method of any one of claims 96-118 and 120, wherein a level of activation of the effector protein negatively correlates with a first level of activation of the first signal transducer and/or a second level of activation of the second signal transducer.

122. The method of claim 121, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

123. The method of any one of claims 96-122, wherein the effector protein comprises a third signal transducer binding domain, and wherein the third signal transducer binding domain binds the first signal transducer and/or the second signal transducer.

124. The method of any one of claims 96-123, wherein the synthetic protein circuit further comprises a repressor protein, wherein the repressor protein comprises a second protease.

125. The method of claim 124, wherein the second protease in a second protease active state cuts a first cut site of the first polypeptide and/or a second cut site of the second polypeptide.

126. The method of claim 125, wherein the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide.

127. The method of any one of claims 124-126, wherein the repressor protein comprises a cut site the first protease in the first protease active state cuts.

128. The method of claim 127, wherein the repressor protein is changed into a repressor destabilized state, a repressor delocalized state, and/or a repressor inactivate state after the first protease cuts the cut site of the repressor protein.

129. The method of any one of claims 124-127, wherein the effector protein comprises a second cut site the second protease in the second protease active state cuts.

130. The method of claim 129, wherein the effector protein is changed into a first effector destabilized state, a first effector delocalized state, and/or a first effector inactivate state after the second protease in the second protease active state cuts the cut site of the effector protein.

131. The method of any one of claims 124-130, wherein the effector protein comprises a degron, wherein the second protease in the second protease active state cuts the second cut site of the effector protein to expose the degron, and wherein the degron of the effector protein being exposed changes the effector protein to an effector destabilized state.

132. The method of claim 125, wherein the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide.

133. The method of any one of claims 124-125 and 132, wherein the repressor protein comprises a cut site the first protease in the first protease active state cuts.

134. The method of claim 133, wherein the repressor protein is changed into a repressor stabilized state, a repressor localized state, and/or a repressor activate state after the first protease in the first protease active state cuts the first cut site of the repressor protein.

135. The method of any one of claims 124-125 and 132-134, wherein the effector protein comprises a second cut site the second protease in the second protease active state cuts.

136. The method of claim 135, wherein the effector protein is changed into a first effector stabilized state, a first effector localized state, and/or a first effector activate state after the second protease in the second protease active state cuts the second cut site of the effector protein.

137. The method of any one of claims 124-125 and 132-136, wherein the effector protein comprises a degron, wherein the second protease in the second protease active state cuts the second cut site of the effector protein to hide the degron, and wherein the degron of the effector protein being hidden changes the effector protein to an effector stabilized state.

138. The method of any one of claims 96-137, wherein the effector protein changes a synthetic protein circuit component of the synthetic protein circuit to a synthetic protein circuit component active state.

139. The method of claim 138, wherein the effector protein comprises a third protease domain, and wherein the third protease domain is changed to an effector inactive state after the second protease in the second protease active state cuts the cute site of the effector protein.

140. The method of claim 138, wherein the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector.

141. The method of any one of claims 96-140, wherein the effector protein in an effector active state activates an endogenous signal transduction pathway.

142. The method of any one of claims 96-140, wherein the effector protein in an effector active state inactivates an endogenous signal transduction pathway.

143. The method of any one of claims 96-142, wherein the effector protein comprises Caspase-3, Caspase 7, Caspase-9, Caspase-8, Bax, Bid, Bad, Bak, BCL2L11, p53, PUMA, Diablo/SMAC, S-TRAIL, or any combination thereof.

144. The method of any one of claims 1-142, wherein the effector protein in an effector active state renders a resident cell sensitive to a prodrug.

145. The method of claim 144, wherein the effector protein comprises cytosine deaminase and uracil phosphoribosyl transferase, and wherein the prodrug is 5-fluorocytosine (5-FC).

146. The method of claim 144, wherein the effector protein comprises thymidine kinase (TK), and the wherein the prodrug comprises ganciclovir.

147. The method of any one of claims 96-146, wherein two or more of the first signal transducer binding domain, the second signal transducer binding domain, and/or third signal transducer binding domain are identical.

148. The method of any one of claims 96-146, wherein two or more of the first signal transducer binding domain, the second signal transducer binding domain, and/or third signal transducer binding domain are different.

149. The method of any one of claims 96-148, wherein the first signal transducer binding domain, the second signal transducer binding domain, and/or third signal transducer binding domain each bind molecules of the first signal transducer and/or the second signal transducer.

150. The method of any one of claims 96-147, wherein the third signal transducer binding domain binds to a third signal transducer at the association location.

151. The method of claim 150, wherein the first signal transducer, the second signal transducer, and/or the third signal transducer belongs to a signal transduction pathway.

152. The method of any one of claims 96-151, wherein the first signal transducer binding domain, the second signal transducer binding domain, and/or the third signal transducer binding domain comprise a RAS binding domain (RBD) and/or RAS association domain (RAD).

153. The method of any one of claims 96-152, wherein the first signal transducer binding domain, the second signal transducer binding domain, and/or the third signal transducer binding domain comprises a lipid binding domain.

154. The method of claim 153, wherein the lipid binding domain comprises a Pleckstrin homology (PH) domain.

155. The method of any one of claims 96-153, wherein the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

156. The method of any one of claims 96-152, wherein the first signal transducer binds the first signal transducer binding domain and/or the second signal transducer binds the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof.

157. The method of any one of claims 96-156, wherein the first signal transducer, the second signal transducer, or both are endogenous proteins.

158. The method of any one of claims 96-157, wherein the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof.

159. The method of any one of claims 96-158, wherein the first signal transducer and/or the second signal transducer regulate cell survival, cell growth, cell proliferation, cell adhesion, cell migration, cell metabolism, cell morphology, cell differentiation, apoptosis, or any combination thereof.

160. The method of any one of claims 96-159, wherein the first signal transducer, the second signal transducer, or both comprise a RAS protein.

161. The method of claim 160, wherein the RAS protein is KRAS, NRHAS, HRAS, or any combination thereof.

162. The method of any one of claims 96-156, wherein the first signal transducer, the second signal transducer, or both are exogenous proteins.

163. The method of claim 162, wherein the synthetic protein circuit comprises the first signal transducer, the second signal transducer, or both.

164. The method of any one of claims 96-163, wherein the first signal transducer, the second signal transducer, or both comprise a lipid.

165. The method of claim 164, wherein the lipid comprises a phospholipid.

166. The method of claim 165, wherein the phospholipid is phosphatidylinositol 3-phosphate.

167. The method of any one of claims 96-166, wherein the synthetic protein circuit detects an activity of the first signal transducer and an activity of the second signal transducer.

168. The method of any one of claims 96-167, wherein an activity of the effector protein correlates with an activity of the first signal transducer and/or an activity of the second signal transducer.

169. The method of any one of claims 96-168, wherein the synthetic protein circuit detects activities of the first signal transducer and activities of the second signal transducer over a period of time.

170. The method of any one of claims 96-169, wherein activities of the effector protein correlate with activities of the first signal transducer and activities of the second signal transducer over a period of time.

171. The method of any one of claims 96-170, wherein the synthetic protein circuit detects an aberrant signaling.

172. The method of claim 171, wherein aberrant signaling involves an active signal transducer.

173. The method of any one of claims 171-172, wherein the aberrant signaling involves an overactive signal transducer.

174. The method of any one of claims 171-173, wherein the aberrant signaling involves a constitutively active signal transducer over a period of time.

175. The method of any one of claims 96-174, wherein the synthetic protein circuit detects an activity of a signal transducer activator and/or an activity of a signal transducer repressor.

176. The method of any one of claims 96-175, wherein the effector protein detects an activity of a signal transducer activator and/or an activity of a signal transducer repressor.

177. The method of any one of claims 175-176, wherein the synthetic protein circuit comprises one or more circuit components that increase a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor.

178. The method of any one of claims 175-177, wherein the synthetic protein circuit comprises one or more circuit components that increase a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

179. The method of any one of claims 175-178, wherein the aberrant signaling involves an active signal transducer repressor and an active signal transducer.

180. The method of any one of claims 175-179, wherein the aberrant signaling involves an inactive signal transducer activator and an active signal transducer.

181. The method of any one of claims 175-180, wherein the aberrant signaling involves an inactive signal transducer.

182. The method of any one of claims 175-181, wherein the aberrant signaling involves an underactive signal transducer.

183. The method of any one of claims 175-182, wherein the aberrant signaling involves a constitutively inactive signal transducer over a period of time.

184. The method of any one of claims 175-183, wherein the aberrant signaling involves an inactive signal transducer repressor and an inactive signal transducer.

185. The method of any one of claims 175-184, wherein the aberrant signaling involves an active signal transducer activator and an inactive signal transducer.

186. The method of any one of claims 175-185, wherein the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

187. The method of any one of claims 175-186, wherein the synthetic protein circuit directly or indirectly induces cell death in the presence of the aberrant signaling.

188. The method of any one of claims 175-187, wherein the effector protein directly or indirectly induces cell death in the presence of aberrant signaling.

189. The method of any one of claims 175-188, wherein the synthetic protein circuit directly or indirectly induces cell death when a first level of activation of the first signal transducer is above a first signal transducer activation threshold and/or a second level of activation of the second signal transducer is below a second signal transducer activation threshold.

190. The method of any one of claims 96-189, wherein the effector protein directly or indirectly induces cell death when a first level of activation of the first signal transducer is above a first signal transducer activation threshold and/or a second level of activation of the second signal transducer is below a second signal transducer activation threshold.

191. The method of any one of claims 96-190, wherein the disease or disorder is characterized by an aberrant signaling of the first transducer.

192. The method of any one of claims 96-190, wherein the disease or disorder is characterized by an aberrant signaling of the first transducer and an aberrant signaling of the second transducer, and wherein the first transducer and the second transducer are identical.

193. The method of any one of claims 96-190, wherein the disease or disorder is characterized by an aberrant signaling of the first transducer and an aberrant signaling of the second transducer, and wherein the first transducer and the second transducer are different.

194. The method of any one of claims 96-193, wherein the disease or disorder is characterized by an aberrant signaling of a RAS protein.

195. The method of any one of claims 96-194, wherein the disease or disorder is a cancer.

196. The method of any one of claims 96-194, wherein the disease or disorder is a RASopathy selected from the group comprising Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, Legius syndrome, or any combination thereof.

197. The method of any one of claims 96-194, wherein the disease is a neurological disease or a neurodegenerative disease.

198. The method of any one of claims 96-194, wherein the disease is an autoimmune disease 199. The method of any one of claims 96-194, wherein the disease is infectious disease.

200. The method of any one of claims 96-199, further comprising administering a prodrug.

201. The method of claim 200, wherein the prodrug is 5-fluorocytosine (5-FC) or ganciclovir.

202. The method of any one of claims 96-201, wherein the expressing comprises administering a nucleic acid encoding the synthetic protein circuit.

203. The method of any one of claims 96-201, wherein the expressing comprises administering two or more nucleic acids, wherein the two or more nucleic acids encode the synthetic protein circuit.

204. The method of any one of claims 202-203, wherein the nucleic acid comprises at least one regulatory element for expression of the synthetic protein circuit.

205. The method of any one of claims 202-204, wherein the nucleic acid comprises a vector.

206. The method of claim 205, wherein the vector comprises a adenovirus vector, an adeno-associated virus vector, an Epstein-Barr virus vector, a Herpes virus vector, an attenuated HIV vector, a retroviral vector, a vaccinia virus vector, or any combination thereof.

207. The method of any one of claims 205-206, wherein the vector comprises an RNA viral vector.

208. The method of any one of claims 205-207, wherein the vector is derived from one or more negative-strand RNA viruses of the order Mononegavirales.

209. The method of any one of claims 205-208, wherein the vector is a rabies viral vector. 210. The method of any one of claims 200-209, wherein the administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof.

211. A method of measuring a level of activation of one or more signal transducers comprising:
    expressing a synthetic protein circuit in a cell of a subject in need thereof, the synthetic protein circuit comprising:
        a first polypeptide comprising a first signal transducer binding domain and a first part of a first protease domain, wherein the first signal transducer binding domain is capable of binding a first signal transducer to form a first signal transducer-bound polypeptide;

a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and an effector protein comprising a first cut site the first protease in the first protease active state is capable of cutting, wherein a level of activation of the effector protein indicates a first level of activation of the first signal transducer and/or a second level of activation of the second signal transducer.

212. The method of claim 211, wherein the first signal transducer binding domain of the first polypeptide and the second signal transducer binding domain of the second polypeptide are identical.

213. The method of any one of claims 211-212, wherein the first transducer and the second transducer are identical.

214. The method of any one of claims 211-213, wherein the first signal transducer, the second signal transducer, or both, localize at the association location.

215. The method of any one of claims 211-214, wherein the first signal transducer when in a first signal transducer active state, the second signal transducer when in a second signal transducer active state, or both, localize at the association location.

216. The method of any one of claims 211-215, wherein the first signal transducer when in a first inactive state, the second signal transducer when in a second inactive state, or both, localize at the association location.

217. The method of any one of claims 211-216, wherein the first signal transducer binding domain of the first polypeptide binds to the first signal transducer, wherein the second signal transducer binding domain of the second polypeptide binds to the second signal transducer, or both.

218. The method of any one of claims 211-217, wherein the first signal transducer binding domain of the first polypeptide binds to the first signal transducer in a first signal transducer active state, wherein the second signal transducer binding domain of the second polypeptide binds to the second signal transducer in a second signal transducer active state, or both.

219. The method of any one of claims 211-218, wherein the first signal transducer binding domain of the first polypeptide binds to the first signal transducer in a first inactive state, wherein the second signal transducer binding domain of the second polypeptide binds to the second signal transducer in a second inactive state, or both.

220. The method of any one of claims 211-219, wherein the signal transducer binding domain of the first polypeptide binds the first signal transducer to form the first signal transducer-bound polypeptide at the association location, wherein the signal transducer binding domain of the first polypeptide binds the first signal transducer to form the first signal transducer-bound polypeptide at the association location, or both.

221. The method of any one of claims 211-220, wherein the signal transducer binding domain of the first polypeptide binds the first signal transducer to form the first signal transducer-bound polypeptide at a first cellular location other than the association location, wherein the signal transducer binding domain of the first polypeptide binds the first signal transducer to form the first signal transducer-bound polypeptide at a second cellular location other than the association location, or both.

222. The method of claim 221, wherein the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

223. The method of any one of claims 211-222, wherein the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

224. The method of any one of claims 211-223, wherein a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state.

225. The method of any one of claims 211-224, wherein a first concentration of the first protease in the first protease active state is at least two-fold higher at the association location as compared a cellular location other than the association location when the first signal transducer is in a first signal transducer active state and/or when the second signal transducer is in a second signal transducer active state.

226. The method of any one of claims 211-225, wherein the first part of the first protease domain and the second part of the first protease domain have the weak association affinity when the first signal transducer is in a first signal transducer inactive state and/or the second signal transducer inactive state.

227. The method of any one of claims 211-226, wherein the first part of the first protease domain and the second part of the first protease domain are incapable of associating to form the first protease in the first protease active state when the first signal transducer is in a first signal transducer inactive state and/or the second signal transducer is in a second signal transducer inactive state.

228. The method of any one of claims 211-227, wherein a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state.

229. The method of any one of claims 211-228, wherein a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state.

230. The method of any one of claims 211-229, wherein the first part of the first protease domain and the second part of the first protease domain associate with each other to form the first protease in the first protease active state at a threshold first polypeptide concentration and a threshold second polypeptide concentration at the association location.

231. The method of claim 230, wherein the threshold first polypeptide concentration and the threshold second polypeptide concentration at the association location are reached at a threshold signal transducer activation level of the signal transducer.

232. The method of any one of claims 211-231, wherein the effector protein changes from an effector inactive state to an effector active state when the first protease in the first protease active state cuts the first cut site of the effector.

233. The method of any one of claims 211-232, wherein a level of activation of the effector protein positively correlates with a first level of activation of the first signal transducer and/or a second level of activation of the second signal transducer.

234. The method of claim 233, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

235. The method of any one of claims 211-234, wherein the effector protein changes from an effector active state to an effector inactive state when the first protease in the first protease active state cuts the first cut site of the effector.

236. The method of any one of claims 211-233 and 235, wherein a level of activation of the effector protein negatively correlates with a first level of activation of the first signal transducer and/or a second level of activation of the second signal transducer.

237. The method of claim 236, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

238. The method of any one of claims 211-237, wherein the effector protein comprises a third signal transducer binding domain, and wherein the third signal transducer binding domain binds the first signal transducer and/or the second signal transducer.

239. The method of any one of claims 211-238, wherein the synthetic protein circuit further comprises a repressor protein, wherein the repressor protein comprises a second protease.

240. The method of claim 239, wherein the second protease in a second protease active state cuts a first cut site of the first polypeptide and/or a second cut site of the second polypeptide.

241. The method of claim 240, wherein the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide.

242. The method of any one of claims 239-241, wherein the repressor protein comprises a cut site the first protease in the first protease active state cuts.

243. The method of claim 242, wherein the repressor protein is changed into a repressor destabilized state, a repressor delocalized state, and/or a repressor inactivate state after the first protease cuts the cut site of the repressor protein.

244. The method of any one of claims 124-242, wherein the effector protein comprises a second cut site the second protease in the second protease active state cuts.

245. The method of claim 244, wherein the effector protein is changed into a first effector destabilized state, a first effector delocalized state, and/or a first effector inactivate state after the second protease in the second protease active state cuts the cut site of the effector protein.

246. The method of any one of claims 239-245, wherein the effector protein comprises a degron, wherein the second protease in the second protease active state cuts the second cut site of the effector protein to expose the degron, and wherein the degron of the effector protein being exposed changes the effector protein to an effector destabilized state.

247. The method of claim 240, wherein the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide.

248. The method of any one of claims 239-240 and 247, wherein the repressor protein comprises a cut site the first protease in the first protease active state cuts.

249. The method of claim 248, wherein the repressor protein is changed into a repressor stabilized state, a repressor localized state, and/or a repressor activate state after the first protease in the first protease active state cuts the first cut site of the repressor protein.

250. The method of any one of claims 239-240 and 247-249, wherein the effector protein comprises a second cut site the second protease in the second protease active state cuts.

251. The method of claim 250, wherein the effector protein is changed into a first effector stabilized state, a first effector localized state, and/or a first effector activate state after the second protease in the second protease active state cuts the second cut site of the effector protein.

252. The method of any one of claims 239-240 and 247-251, wherein the effector protein comprises a degron, wherein the second protease in the second protease active state cuts the second cut site of the effector protein to hide the degron, and wherein the degron of the effector protein being hidden changes the effector protein to an effector stabilized state.

253. The method of any one of claims 211-252, wherein the effector protein changes a synthetic protein circuit component of the synthetic protein circuit to a synthetic protein circuit component active state.

254. The method of claim 253, wherein the effector protein comprises a third protease domain, and wherein the third protease domain is changed to an effector inactive state after the second protease in the second protease active state cuts the cute site of the effector protein.

255. The method of claim 253, wherein the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector.

256. The method of any one of claims 211-255, wherein two or more of the first signal transducer binding domain, the second signal transducer binding domain, and/or third signal transducer binding domain are identical.

257. The method of any one of claims 211-255, wherein two or more of the first signal transducer binding domain, the second signal transducer binding domain, and/or third signal transducer binding domain are different.

258. The method of any one of claims 211-257, wherein the first signal transducer binding domain, the second signal transducer binding domain, and/or third signal transducer binding domain each bind molecules of the first signal transducer and/or the second signal transducer.

259. The method of any one of claims 211-256, wherein the third signal transducer binding domain binds to a third signal transducer at the association location.

260. The method of claim 259, wherein the first signal transducer, the second signal transducer, and/or the third signal transducer belongs to a signal transduction pathway.

261. The method of any one of claims 211-260, wherein the first signal transducer binding domain, the second signal transducer binding domain, and/or the third signal transducer binding domain comprise a RAS binding domain (RBD) and/or RAS association domain (RAD).

262. The method of any one of claims 211-261, wherein the first signal transducer binding domain, the second signal transducer binding domain, and/or the third signal transducer binding domain comprises a lipid binding domain.

263. The method of claim 262, wherein the lipid binding domain comprises a Pleckstrin homology (PH) domain.

264. The method of any one of claims 211-263, wherein the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

265. The method of any one of claims 211-264, wherein the first signal transducer binds the first signal transducer binding domain and/or the second signal transducer binds the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof.

266. The method of any one of claims 211-265, wherein the first signal transducer, the second signal transducer, or both are endogenous proteins.

267. The method of any one of claims 211-266, wherein the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof.

268. The method of any one of claims 211-267, wherein the first signal transducer and/or the second signal transducer regulate cell survival, cell growth, cell proliferation, cell adhesion, cell migration, cell metabolism, cell morphology, cell differentiation, apoptosis, or any combination thereof.

269. The method of any one of claims 211-268, wherein the first signal transducer, the second signal transducer, or both comprise a RAS protein.

270. The method of claim 269, wherein the RAS protein is KRAS, NRHAS, HRAS, or any combination thereof.

271. The method of any one of claims 211-265, wherein the first signal transducer, the second signal transducer, or both are exogenous proteins.

272. The method of claim 271, wherein the synthetic protein circuit comprises the first signal transducer, the second signal transducer, or both.

273. The method of any one of claims 211-272, wherein the first signal transducer, the second signal transducer, or both comprise a lipid.

274. The method of claim 273, wherein the lipid comprises a phospholipid.

275. The method of claim 274, wherein the phospholipid is phosphatidylinositol 3-phosphate.

276. The method of any one of claims 211-275, wherein the synthetic protein circuit detects an activity of the first signal transducer and an activity of the second signal transducer.

277. The method of any one of claims 211-276, wherein an activity of the effector protein correlates with an activity of the first signal transducer and/or an activity of the second signal transducer.

278. The method of any one of claims 211-277, wherein the synthetic protein circuit detects activities of the first signal transducer and activities of the second signal transducer over a period of time.

279. The method of any one of claims 211-278, wherein activities of the effector protein correlate with activities of the first signal transducer and activities of the second signal transducer over a period of time.

280. The method of any one of claims 211-279, wherein the synthetic protein circuit detects an activity of a signal transducer activator and/or an activity of a signal transducer repressor.

281. The method of any one of claims 211-280, wherein the effector protein detects an activity of a signal transducer activator and/or an activity of a signal transducer repressor.

282. The method of any one of claims 280-281, wherein the synthetic protein circuit comprises one or more circuit components that increase a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor.

283. The method of any one of claims 280-282, wherein the synthetic protein circuit comprises one or more circuit components that increase a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

284. The method of any one of claims 211-283, wherein the effector protein in an effector active state is capable of generating a first detectable signal.

285. The method of any one of claims 211-284, wherein the effector protein in an effector inactive state is capable of generating a second detectable signal.

286. The method of any one of claims 284-285, wherein the fluorescence emission intensity, fluorescence lifetime, excitation wavelength, and/or emission wavelength of the first detectable signal and second detectable signal are different.

287. The method of any one of claims 284-286, further comprising detecting the first detectable signal and/or second detectable signal.

288. The method of claim 287, wherein detecting the first detectable signal and/or second detectable signal comprises illumination of the effector protein.

289. The method of any one of claims 211-288, wherein the effector protein comprises all or a portion of a fluorescent protein, a luminescent protein, a phosphorescent protein, or any combination thereof.

290. The method of any one of claims 211-289, wherein the effector protein comprises all or a portion of Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, ZsYellow1, DsRed2, AsRed2, and HcRed1, or any combination thereof.

291. The method of any one of claims 284-290, wherein one or more of the fluorescence emission intensity, fluorescence lifetime, excitation wavelength, and/or emission wavelength of the first detectable signal positively correlates with a level of activation of the effector protein.

292. The method of any one of claims 284-291, wherein one or more of the fluorescence emission intensity, fluorescence lifetime, excitation wavelength, and/or emission wavelength of the first detectable signal and/or second detectable signal positively correlates with a first level of activation of the first signal transducer and/or a second level of activation of the second signal transducer.

293. The method of any one of claims 284-292, wherein the first detectable signal and/or second detectable signal can indicate and/or quantify aberrant signaling.

294. The method of claim 293, wherein aberrant signaling involves an active signal transducer.

295. The method of any one of claims 293-294, wherein the aberrant signaling involves an overactive signal transducer.

296. The method of any one of claims 293-295, wherein the aberrant signaling involves a constitutively active signal transducer over a period of time.

297. The method of any one of claims 293-296, wherein the aberrant signaling involves an active signal transducer repressor and an active signal transducer.

298. The method of any one of claims 293-297, wherein the aberrant signaling involves an inactive signal transducer activator and an active signal transducer.

299. The method of any one of claims 293-298, wherein the aberrant signaling involves an inactive signal transducer.

300. The method of any one of claims 293-299, wherein the aberrant signaling involves an underactive signal transducer.

301. The method of any one of claims 293-300, wherein the aberrant signaling involves a constitutively inactive signal transducer over a period of time.

302. The method of any one of claims 293-301, wherein the aberrant signaling involves an inactive signal transducer repressor and an inactive signal transducer.

303. The method of any one of claims 293-302, wherein the aberrant signaling involves an active signal transducer activator and an inactive signal transducer.

304. The method of any one of claims 293-303, wherein the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

305. The method of any one of claims 211-304, wherein the expressing comprises administering a nucleic acid encoding the synthetic protein circuit.

306. The method of any one of claims 211-305, wherein the expressing comprises administering two or more nucleic acids, wherein the two or more nucleic acids encode the synthetic protein circuit.

307. The method of any one of claims 293-306, wherein the nucleic acid comprises at least one regulatory element for expression of the synthetic protein circuit.

308. The method of any one of claims 293-307, wherein the nucleic acid comprises a vector.

309. The method of claim 308, wherein the vector comprises a adenovirus vector, an adeno-associated virus vector, an Epstein-Barr virus vector, a Herpes virus vector, an attenuated HIV vector, a retroviral vector, a vaccinia virus vector, or any combination thereof.

310. The method of any one of claims 308-309, wherein the vector comprises an RNA viral vector.

311. The method of any one of claims 308-310, wherein the vector is derived from one or more negative-strand RNA viruses of the order Mononegavirales.

312. The method of any one of claims 308-311, wherein the vector is a rabies viral vector.

313. The method of any one of claims 293-312, wherein the administering comprises aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof.

314. A nucleic acid encoding a synthetic protein circuit comprising:
   a first polypeptide comprising a first signal transducer binding domain and a first part of a first protease domain, wherein the first signal transducer binding domain is capable of binding a first signal transducer to form a first signal transducer-bound polypeptide;
   a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and
   an effector protein comprising a first cut site the first protease in the first protease active state is capable of cutting.

315. The nucleic acid of claim 314, wherein the first signal transducer binding domain of the first polypeptide and the second signal transducer binding domain of the second polypeptide are identical.

316. The nucleic acid of any one of claims 314-315, wherein the first transducer and the second transducer are identical.

317. The nucleic acid of any one of claims 314-316, wherein the first signal transducer, the second signal transducer, or both, are capable of being localized at the association location.

318. The nucleic acid of any one of claims 314-317, wherein the first signal transducer when in a first signal transducer active state, the second signal transducer when in a second signal transducer active state, or both, are capable of being localized at the association location.

319. The nucleic acid of any one of claims 314-318, wherein the first signal transducer when in a first inactive state, the second signal transducer when in a second inactive state, or both, are capable of being localized at the association location.

320. The nucleic acid of any one of claims 314-319, wherein the first signal transducer binding domain of the first polypeptide is capable of binding to the first signal transducer, wherein the second signal transducer binding domain of the second polypeptide is capable of binding to the second signal transducer, or both.

321. The nucleic acid of any one of claims 314-320, wherein the first signal transducer binding domain of the first polypeptide is capable of binding to the first signal transducer in a first signal transducer active state, wherein the second signal transducer binding domain of the second polypeptide is capable of binding to the second signal transducer in a second signal transducer active state, or both.

322. The nucleic acid of any one of claims 314-321, wherein the first signal transducer binding domain of the first polypeptide is capable of binding to the first signal transducer in a first inactive state, wherein the second signal transducer binding domain of the second polypeptide is capable of binding to the second signal transducer in a second inactive state, or both.

323. The nucleic acid of any one of claims 314-322, wherein the signal transducer binding domain of the first polypeptide is capable of binding the first signal transducer to form the first signal transducer-bound polypeptide at the association location, wherein the signal transducer binding domain of the first polypeptide is capable of binding the first signal transducer to form the first signal transducer-bound polypeptide at the association location, or both.

324. The nucleic acid of any one of claims 314-323, wherein the signal transducer binding domain of the first polypeptide is capable of binding the first signal transducer to form the first signal transducer-bound polypeptide at a first cellular location other than the association location, wherein the signal transducer binding domain of the first polypeptide is capable of binding the first signal transducer to form the first signal transducer-bound polypeptide at a second cellular location other than the association location, or both.

325. The nucleic acid of claim 324, wherein the first cellular location, the second cellular location, or both comprise one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

326. The nucleic acid of any one of claims 314-325, wherein the association location comprises one or more of a cell membrane, lipid raft, mitochondrion, peroxisome, cytosol, vesicle, lysosome, plasma membrane, nucleus, nucleolus, inner mitochondrial matrix, inner mitochondrial membrane, intermembrane space, outer mitochondrial membrane, secretory vesicle, endoplasmic reticulum, Golgi body, phagosome, endosome, exosome, microtubule, microfilament, intermediate filament, filopodium, ruffle, lamellipodium, sarcomere, focal contact, podosome, ribosome, microsome, plasma membrane, nuclear membrane, chloroplast, cell wall, or any combination thereof.

327. The nucleic acid of any one of claims 314-326, wherein a first concentration of the first signal transducer-bound polypeptide is at least two-fold higher at the association location as compared a first cellular location other than the association location when the first signal transducer is a first signal transducer active state, and/or wherein a second concentration of the second signal transducer-bound polypeptide is at least two-fold higher at the association location as compared a second cellular location other than the association location when the second signal transducer is a second signal transducer active state.

328. The nucleic acid of any one of claims 314-327, wherein a first concentration of the first protease in the first protease active state is at least two-fold higher at the association location as compared a cellular location other than the association location when the first signal transducer is in a first signal transducer active state and/or when the second signal transducer is in a second signal transducer active state.

329. The nucleic acid of any one of claims 314-328, wherein the first part of the first protease domain and the second part of the first protease domain have the weak association affinity when the first signal transducer is in a first signal transducer inactive state and/or the second signal transducer inactive state.

330. The nucleic acid of any one of claims 314-329, wherein the first part of the first protease domain and the second part of the first protease domain are incapable of associating to form the first protease in the first protease active state when the first signal transducer is in a first signal transducer inactive state and/or the second signal transducer is in a second signal transducer inactive state.

331. The nucleic acid of any one of claims 314-330, wherein a first concentration of the first signal transducer-bound polypeptide and a second concentration of the second signal transducer-bound polypeptide at the association location are insufficient for the first part of the first protease domain and the second part of the first protease domain to form an active first protease when the first signal transducer is in a first signal transducer inactive state and/or the second signal transducer is in a second signal transducer inactive state.

332. The nucleic acid of any one of claims 314-331, wherein a first concentration of the first signal transducer-bound polypeptide at the association location is comparable to a first cellular location other than the association location when the first signal transducer is in a first signal transducer inactive state, and/or wherein a second concentration of the second signal transducer-bound polypeptide at the association location is comparable to a second cellular location other than the association location when the second signal transducer is in a second signal transducer inactive state.

333. The nucleic acid of any one of claims 314-332, wherein the first part of the first protease domain and the second part of the first protease domain are capable of associating with each other to form the first protease in the first protease active state at a threshold first polypeptide concentration and a threshold second polypeptide concentration at the association location.

334. The nucleic acid of claim 333, wherein the threshold first polypeptide concentration and the threshold second polypeptide concentration at the association location are reached at a threshold signal transducer activation level of the signal transducer.

335. The nucleic acid of any one of claims 314-334, wherein the effector protein changes from an effector inactive state to an effector active state when the first protease in the first protease active state cuts the first cut site of the effector.

336. The nucleic acid of any one of claims 314-335, wherein a level of activation of the effector protein positively correlates with a first level of activation of the first signal transducer and/or a second level of activation of the second signal transducer.

337. The nucleic acid of claim 336, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

338. The nucleic acid of any one of claims 314-337, wherein the effector protein changes from an effector active state to an effector inactive state when the first protease in the first protease active state cuts the first cut site of the effector.

339. The nucleic acid of any one of claims 314-336 and 338, wherein a level of activation of the effector protein negatively correlates with a first level of activation of the first signal transducer and/or a second level of activation of the second signal transducer.

340. The nucleic acid of claim 339, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

341. The nucleic acid of any one of claims 314-340, wherein the effector protein comprises a third signal transducer binding domain, and wherein the third signal transducer binding domain is capable of binding the first signal transducer and/or the second signal transducer.

342. The nucleic acid of any one of claims 314-341, further comprising a repressor protein, wherein the repressor protein comprises a second protease.

343. The nucleic acid of claim 343, wherein the second protease in a second protease active state is capable of cutting a first cut site of the first polypeptide and/or a second cut site of the second polypeptide.

344. The nucleic acid of claim 344, wherein the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide.

345. The nucleic acid of any one of claims 342-344, wherein the repressor protein comprises a cut site the first protease in the first protease active state is capable of cutting.

346. The nucleic acid of claim 345, wherein the repressor protein is changed into a repressor destabilized state, a repressor delocalized state, and/or a repressor inactivate state after the first protease cuts the cut site of the repressor protein.

347. The nucleic acid of any one of claims 342-344, wherein the effector protein comprises a second cut site the second protease in the second protease active state is capable of cutting.

348. The nucleic acid of claim 347, wherein the effector protein is changed into a first effector destabilized state, a first effector delocalized state, and/or a first effector inactivate state after the second protease in the second protease active state cuts the cut site of the effector protein.

349. The nucleic acid of any one of claims 342-348, wherein the effector protein comprises a degron, wherein the second protease in the second protease active state is capable of cutting the second cut site of the effector protein to expose the degron, and wherein the degron of the effector protein being exposed changes the effector protein to an effector destabilized state.

350. The nucleic acid of claim 343, wherein the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide is changed into a second polypeptide stabilized state, a second polypeptide localized state, and/or a second polypeptide activate state after the second protease in the second protease active state cuts the second cut site of the second polypeptide.

351. The nucleic acid of any one of claims 342-343 and 350, wherein the repressor protein comprises a cut site the first protease in the first protease active state is capable of cutting.

352. The nucleic acid of claim 351, wherein the repressor protein is changed into a repressor stabilized state, a repressor localized state, and/or a repressor activate state after the first protease in the first protease active state cuts the first cut site of the repressor protein.

353. The nucleic acid of any one of claims 342-343 and 350-352, wherein the effector protein comprises a second cut site the second protease in the second protease active state is capable of cutting.

354. The nucleic acid of claim 353, wherein the effector protein is changed into a first effector stabilized state, a first effector localized state, and/or a first effector activate state after the second protease in the second protease active state cuts the second cut site of the effector protein.

355. The nucleic acid of any one of claims 342-343 and 350-354, wherein the effector protein comprises a degron, wherein the second protease in the second protease active state is capable of cutting the second cut site of the effector protein to hide the degron, and wherein the degron of the effector protein being hidden changes the effector protein to an effector stabilized state.

356. The nucleic acid of any one of claims 314-355, wherein the effector protein is capable of changing a synthetic protein circuit component of the synthetic protein circuit to a synthetic protein circuit component active state.

357. The nucleic acid of claim 356, wherein the effector protein comprises a third protease domain, and wherein the third protease domain is changes to an effector inactive state after the second protease in the second protease active state cuts the cute site of the effector protein.

358. The nucleic acid of claim 356, wherein the effector protein comprises a third protease domain, wherein the effector protein is changed to an effector active state or an effector stabilized state after the first protease in the first protease active state cuts the first cut site of the effector protein, and wherein the effector protein changes to an effector inactive state or an effector destabilized state after the second protease in the second protease active state cuts the second cut site of the effector.

359. The nucleic acid of any one of claims 314-358, wherein the effector protein in an effector active state is capable of activating an endogenous signal transduction pathway.

360. The nucleic acid of any one of claims 314-359, wherein the effector protein in an effector active state is capable of inactivating an endogenous signal transduction pathway.

361. The nucleic acid of any one of claims 314-360, wherein the effector protein comprises Caspase-3, Caspase 7, Caspase-9, Caspase-8, Bax, Bid, Bad, Bak, BCL2L11, p53, PUMA, Diablo/SMAC, S-TRAIL, or any combination thereof.

362. The nucleic acid of any one of claims 314-361, wherein the effector protein in an effector active state is capable of rendering a resident cell sensitive to a prodrug.

363. The nucleic acid of claim 362, wherein the effector protein comprises cytosine deaminase and uracil phosphoribosyl transferase, and wherein the prodrug is 5-fluorocytosine (5-FC).

364. The nucleic acid of claim 362, wherein the effector protein comprises thymidine kinase (TK), and the wherein the prodrug comprises ganciclovir.

365. The nucleic acid of any one of claims 314-364, wherein two or more of the first signal transducer binding domain, the second signal transducer binding domain, and/or third signal transducer binding domain are identical.

366. The nucleic acid of any one of claims 314-364, wherein two or more of the first signal transducer binding domain, the second signal transducer binding domain, and/or third signal transducer binding domain are different.

367. The nucleic acid of any one of claims 314-366, wherein the first signal transducer binding domain, the second signal transducer binding domain, and/or third signal transducer binding domain each is capable of binding molecules of the first signal transducer and/or the second signal transducer.

368. The nucleic acid of any one of claims 314-365, wherein the third signal transducer binding domain is capable of binding to a third signal transducer at the association location.

369. The nucleic acid of claim 368, wherein the first signal transducer, the second signal transducer, and/or the third signal transducer belongs to a signal transduction pathway.

370. The nucleic acid of any one of claims 314-369, wherein the first signal transducer binding domain, the second signal transducer binding domain, and/or the third signal transducer binding domain comprise a RAS binding domain (RBD) and/or RAS association domain (RAD).

371. The nucleic acid of any one of claims 314-370, wherein the first signal transducer binding domain, the second signal transducer binding domain, and/or the third signal transducer binding domain comprises a lipid binding domain.

372. The nucleic acid of claim 371, wherein the lipid binding domain comprises a Pleckstrin homology (PH) domain.

373. The nucleic acid of any one of claims 314-372, wherein the first signal transducer binding domain, the second signal transducer binding domain, and/or the third signal transducer binding domain comprises a nanobody, a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), single-domain antibody (sdAb), or any combination thereof.

374. The nucleic acid of any one of claims 314-373, wherein the first signal transducer is capable of binding the first signal transducer binding domain and/or the second signal transducer is capable of binding the second signal transducer binding domain following a modification selected from the group comprising phosphorylation, dephosphorylation, acetylation, methylation, acylation, glycosylation, glycosylphosphatidylinositol (GPI) anchoring, sulfation, disulfide bond formation, deamidation, ubiquitination, sumoylation, nitration of tyrosine, hydrolysis of ATP or GTP, binding of ATP or GTP, cleavage, or any combination thereof.

375. The nucleic acid of any one of claims 314-374, wherein the first signal transducer, the second signal transducer, or both are endogenous proteins.

376. The nucleic acid of any one of claims 314-375, wherein the first signal transducer, the second signal transducer, or both comprise AKT, PI3K, MAPK, p44/42 MAP kinase, TYK2, p38 MAP kinase, PKC, PKA, SAPK, ELK, JNK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof.

377. The nucleic acid of any one of 314-376, wherein the first signal transducer and/or the second signal transducer are capable of regulating cell survival, cell growth, cell proliferation, cell adhesion, cell migration, cell metabolism, cell morphology, cell differentiation, apoptosis, or any combination thereof.

378. The nucleic acid of any one of claims 314-377, wherein the first signal transducer, the second signal transducer, or both comprise a RAS protein.

379. The nucleic acid of claim 378, wherein the RAS protein is KRAS, NRHAS, HRAS, or any combination thereof.

380. The nucleic acid of any one of claims 314-374, wherein the first signal transducer, the second signal transducer, or both are exogenous proteins.

381. The nucleic acid of claim 380, wherein the synthetic protein circuit comprises the first signal transducer, the second signal transducer, or both.

382. The nucleic acid of any one of claims 314-381, wherein the first signal transducer, the second signal transducer, or both comprise a lipid.

383. The nucleic acid of claim 382, wherein the lipid comprises a phospholipid. 384. The nucleic acid of claim 383, wherein the phospholipid is phosphatidylinositol 3-phosphate.

385. The nucleic acid of any one of claims 314-384, wherein the synthetic protein circuit is capable of detecting an activity of the first signal transducer and an activity of the second signal transducer.

386. The nucleic acid of any one of claims 314-385, wherein an activity of the effector protein correlates with an activity of the first signal transducer and/or an activity of the second signal transducer.

387. The nucleic acid of any one of claims 314-386, wherein the synthetic protein circuit is capable of detecting activities of the first signal transducer and activities of the second signal transducer over a period of time.

388. The nucleic acid of any one of claims 314-387, wherein activities of the effector protein correlate with activities of the first signal transducer and activities of the second signal transducer over a period of time.

389. The nucleic acid of any one of claims 314-388, wherein the synthetic protein circuit is capable of detecting an aberrant signaling.

390. The nucleic acid of claim 389, wherein aberrant signaling involves an active signal transducer.

391. The nucleic acid of any one of claims 389-390, wherein the aberrant signaling involves an overactive signal transducer.

392. The nucleic acid of any one of claims 389-391, wherein the aberrant signaling involves a constitutively active signal transducer over a period of time.

393. The nucleic acid of any one of claims 314-392, wherein the synthetic protein circuit is capable of detecting an activity of a signal transducer activator and/or an activity of a signal transducer repressor.

394. The nucleic acid of any one of claims 314-393, wherein the effector protein is capable of detecting an activity of a signal transducer activator and/or an activity of a signal transducer repressor.

395. The nucleic acid of any one of claims 393-394, wherein the synthetic protein circuit comprises one or more circuit components that are capable of increasing a stability of the effector protein, decreasing the stability of the effector protein, increasing a level of activation of the effector protein, decreasing the level of activation of the effector protein, or any combination thereof, in response to the activity of a signal transducer activator and/or a signal transducer repressor.

396. The nucleic acid of any one of claims 393-395, wherein the synthetic protein circuit comprises one or more circuit components that are capable of increasing a stability of the repressor protein, decreasing the stability of the repressor protein, increasing the level of activation of the repressor protein, decreasing the level of activation of the repressor protein, or any combination thereof, in response to the activity of a signal transducer activator and/or a signal transducer repressor.

397. The nucleic acid of any one of claims 393-396, wherein the aberrant signaling involves an active signal transducer repressor and an active signal transducer.

398. The nucleic acid of any one of claims 393-397, wherein the aberrant signaling involves an inactive signal transducer activator and an active signal transducer.

399. The nucleic acid of any one of claims 393-398, wherein the aberrant signaling involves an inactive signal transducer.

400. The nucleic acid of any one of claims 393-399, wherein the aberrant signaling involves an underactive signal transducer.

401. The nucleic acid of any one of claims 393-400, wherein the aberrant signaling involves a constitutively inactive signal transducer over a period of time.

402. The nucleic acid of any one of claims 393-401, wherein the aberrant signaling involves an inactive signal transducer repressor and an inactive signal transducer.

403. The nucleic acid of any one of claims 393-402, wherein the aberrant signaling involves an active signal transducer activator and an inactive signal transducer.

404. The nucleic acid of any one of claims 393-403, wherein the aberrant signaling involves an active signal transducer, and wherein the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof.

405. The nucleic acid of any one of claims 393-404, wherein the synthetic protein circuit is capable of directly or indirectly inducing cell death in the presence of the aberrant signaling.

406. The nucleic acid of any one of claims 393-405, wherein the effector protein is capable of directly or indirectly inducing cell death in the presence of aberrant signaling.

407. The nucleic acid of any one of claims 314-406, wherein the synthetic protein circuit is capable of directly or indirectly inducing cell death when a first level of activation of the first signal transducer is above a first signal transducer activation threshold and/or a second level of activation of the second signal transducer is below a second signal transducer activation threshold.

408. The nucleic acid of any one of claims 314-407, wherein the effector protein is capable of directly or indirectly inducing cell death when a first level of activation of the first signal transducer is above a first signal transducer activation threshold and/or a second level of activation of the second signal transducer is below a second signal transducer activation threshold.

409. The nucleic acid of any one of claims 314-408, wherein the first polypeptide, the second polypeptide, the effector protein, and/or the repressor protein are encoded on a single open reading frame, and wherein two or more of the first polypeptide, the second polypeptide, the effector protein, and repressor protein are separated by one or more self-cleaving peptides.

410. The nucleic acid of any one of claims 314-409, wherein the first polypeptide, the second polypeptide, the effector protein, and/or the repressor protein are encoded on a single transcript, and wherein translations of the first polypeptide, the second polypeptide, the effector protein, and/or the repressor protein are each driven by a separate internal ribosome entry site.

411. The nucleic acid of claim 410, wherein the sequences of the internal ribosome entry sites are identical.

412. The nucleic acid of claim 410, wherein the sequences of the internal ribosome entry sites are different.

413. The nucleic acid of any one of claims 314-412, wherein the nucleic acid comprises a vector.

414. The nucleic acid of claim 413, wherein the vector comprises a adenovirus vector, an adeno-associated virus vector, an Epstein-Barr virus vector, a Herpes virus vector, an attenuated HIV vector, a retroviral vector, a vaccinia virus vector, or any combination thereof.

415. The nucleic acid of any one of claims 413-414, wherein the vector comprises an RNA viral vector.

416. The nucleic acid of any one of claims 413-415, wherein the vector is derived from one or more negative-strand RNA viruses of the order Mononegavirales.

417. The nucleic acid of any one of claims 413-416, wherein the vector is a rabies viral vector.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A synthetic protein circuit, comprising:
a first polypeptide comprising a first signal transducer binding domain and a first part of a first protease domain, wherein the first signal transducer binding domain is capable of binding a first signal transducer to form a first signal transducer-bound polypeptide;
a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location; and
an effector protein comprising a first cut site the first protease in the first protease active state is capable of cutting.

2. The synthetic protein circuit of claim 1, wherein the first signal transducer binding domain of the first polypeptide and the second signal transducer binding domain of the second polypeptide are identical, and/or wherein the first signal transducer and the second signal transducer are identical.

3. The synthetic protein circuit of claim 1,
wherein the first signal transducer binding domain of the first polypeptide is capable of binding to the first signal transducer in a first signal transducer active state and/or wherein the second signal transducer binding domain of the second polypeptide is capable of binding to the second signal transducer in a second signal transducer active state,
wherein the first signal transducer binding domain of the first polypeptide is capable of binding to the first signal transducer in a first signal transducer inactive state, and/or wherein the second signal transducer binding domain of the second polypeptide is capable of binding to the second signal transducer in a second signal transducer inactive state,
wherein the signal transducer binding domain of the first polypeptide is capable of binding the first signal transducer to form the first signal transducer-bound polypeptide at the association location and/or wherein the signal transducer binding domain of the second polypeptide is capable of binding the second signal transducer to form the second signal transducer-bound polypeptide at the association location, and/or
wherein the signal transducer binding domain of the first polypeptide is capable of binding the first signal transducer to form the first signal transducer-bound polypeptide at a first cellular location other than the association location, wherein the signal transducer binding domain of the second polypeptide is capable of binding the second signal transducer to form the second signal transducer-bound polypeptide at a second cellular location other than the association location, or both.

4. The synthetic protein circuit of claim 1, wherein the first signal transducer, the second signal transducer, or both belong to a signal transduction pathway, wherein the first signal transducer, the second signal transducer, or both are endogenous proteins, wherein the first signal transducer and/or the second signal transducer are capable of regulating cell survival, cell growth, cell proliferation, cell adhesion, cell migration, cell metabolism, cell morphology, cell differentiation, apoptosis, or any combination thereof.

5. The synthetic protein circuit of claim 1,
wherein the first signal transducer, the second signal transducer, or both, are capable of being localized at the association location,
wherein the first signal transducer when in a first signal transducer active state, the second signal transducer when in a second signal transducer active state, or both, are capable of being localized at the association location, and/or
wherein the first signal transducer when in a first inactive state, the second signal transducer when in a second inactive state, or both, are capable of being localized at the association location.

6. The synthetic protein circuit of claim 1, wherein the first part of the first protease domain and the second part of the first protease domain have the weak association affinity when the first signal transducer is in a first signal transducer inactive state and/or the second signal transducer inactive state, and/or wherein the first part of the first protease domain and the second part of the first protease domain are incapable of associating to form the first protease in the first protease active state when the first signal transducer is in a first signal transducer inactive state and/or the second signal transducer is in a second signal transducer inactive state.

7. The synthetic protein circuit of claim 1, wherein the first part of the first protease domain and the second part of the first protease domain are capable of associating with each other to form the first protease in the first protease active state at a threshold first polypeptide concentration and a threshold second polypeptide concentration at the association location, wherein the threshold first polypeptide concentration and the threshold second polypeptide concentration at the association location are reached at a threshold signal transducer activation level of the first signal transducer and a threshold signal transducer activation level of the second signal transducer.

8. The synthetic protein circuit of claim 1, wherein the effector protein is capable of changing a synthetic protein circuit component of the synthetic protein circuit to a synthetic protein circuit component active state.

9. The synthetic protein circuit of claim 1, wherein the effector protein changes from an effector active state to an effector inactive state when the first protease in the first protease active state cuts the first cut site of the effector protein, wherein the effector protein in an effector active state is capable of activating or inactivating an endogenous signal transduction pathway, and/or wherein the effector protein in an effector active state is capable of inactivating an endogenous signal transduction pathway.

10. The synthetic protein circuit of claim 1, wherein the effector protein changes from an effector inactive state to an effector active state when the first protease in the first protease active state cuts the first cut site of the effector.

11. The synthetic protein circuit of claim 10, wherein a level of activation of the effector protein positively correlates with a first level of activation of the first signal transducer and/or a second level of activation of the second signal transducer,
wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

12. The synthetic protein circuit of claim 1, wherein the effector protein changes from an effector active state to an effector inactive state when the first protease in the first protease active state cuts the first cut site of the effector protein, wherein a level of activation of the effector protein negatively correlates with a first level of activation of the first signal transducer and/or a second level of activation of the second signal transducer, wherein the level of activation of the effector protein is related to a number of molecules of the effector protein in an effector active state, wherein the first level of activation of the first signal transducer is related to a number of molecules of the first signal transducer in a first transducer active state, and/or wherein the second level of activation of the second signal transducer is related to a number of molecules of the second signal transducer in a second transducer active state.

13. The synthetic protein circuit of claim 1, further comprising a repressor protein, wherein the repressor protein comprises a cut site the first protease in the first protease active state is capable of cutting, wherein the repressor protein is changed into a repressor destabilized state, a repressor delocalized state, and/or a repressor inactivate state after the first protease cuts the cut site of the repressor protein.

14. The synthetic protein circuit of claim 1, further comprising a repressor protein, wherein the repressor protein comprises a cut site the first protease in the first protease active state is capable of cutting, wherein the repressor protein is changed into a repressor stabilized state, a repressor localized state, and/or a repressor activate state after the first protease in the first protease active state cuts the first cut site of the repressor protein.

15. The synthetic protein circuit of claim 1, further comprising a repressor protein, wherein the repressor protein comprises a second protease, wherein the effector protein further comprises a second cut site the second protease in the second protease active state is capable of cutting, wherein the effector protein is changed into a first effector destabilized state, a first effector delocalized state, and/or a first effector inactivate state after the second protease in the second protease active state cuts the cut site of the effector protein.

16. The synthetic protein circuit of claim 1, further comprising a repressor protein, wherein the repressor protein comprises a second protease, wherein the effector protein further comprises a second cut site the second protease in the second protease active state is capable of cutting, wherein the effector protein is changed into a first effector stabilized state, a first effector localized state, and/or a first effector activate state after the second protease in the second protease active state cuts the second cut site of the effector protein.

17. The synthetic protein circuit of claim 1, further comprising a repressor protein, wherein the repressor protein comprises a second protease, wherein the effector protein further comprises a second cut site the second protease in the second protease active state is capable of cutting, wherein the effector protein further comprises a degron, wherein the second protease in the second protease active state is capable of cutting the second cut site of the effector protein to hide the degron, and wherein the degron of the effector protein being hidden changes the effector protein to an effector stabilized state.

18. The synthetic protein circuit of claim 1, further comprising a repressor protein, wherein the repressor protein comprises a second protease, wherein the effector protein further comprises a second cut site the second protease in the second protease active state is capable of cutting, wherein the effector protein further comprises a degron, wherein the second protease in the second protease active state is capable of cutting the second cut site of the effector protein to expose the degron, and wherein the degron of the effector protein being exposed changes the effector protein to an effector destabilized state, wherein the first polypeptide further comprises a first cut site the second protease in the second protease active state is capable of cutting, wherein the first polypeptide is changed into a first polypeptide stabilized state, a first polypeptide localized state, and/or a first polypeptide activate state after the second protease in the second protease active state cuts the first cut site of the first polypeptide, and/or wherein the second polypeptide further comprises a second cut site the second protease in the second protease active state is capable of cutting, wherein the second polypeptide is changed into a second polypeptide stabilized state, a second polypeptide localized state, and/or a second polypeptide activate state after the second protease in the second protease active state cuts the second cut site of the second polypeptide.

19. The synthetic protein circuit of claim 1, further comprising a repressor protein, wherein the repressor protein comprises a second protease, wherein the first polypeptide further comprises a first cut site the second protease in the second protease active state is capable of cutting, wherein the second polypeptide further comprises a second cut site the second protease in the second protease active state is capable of cutting, wherein the first polypeptide is changed into a first polypeptide destabilized state, a first polypeptide delocalized state, and/or a first polypeptide inactivate state after the second protease in the second protease active state cuts the first cut site of the first polypeptide, and/or wherein the second polypeptide is changed into a second polypeptide destabilized state, a second polypeptide delocalized state, and/or a second polypeptide inactivate state after the second protease in the second protease active state cuts the second cut site of the second polypeptide.

20. A method of treating a disease or disorder characterized by an aberrant signaling of one or more signal transducers comprising:

expressing a synthetic protein circuit in a cell of a subject in need thereof, the synthetic protein circuit comprising:

a first polypeptide comprising a first signal transducer binding domain and a first part of a first protease domain, wherein the first signal transducer binding domain is capable of binding a first signal transducer of the cell to form a first signal transducer-bound polypeptide;

a second polypeptide comprising a second signal transducer binding domain and a second part of the first protease domain, wherein the second signal transducer binding domain is capable of binding a second signal transducer of the cell to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location, and wherein the first signal transducer when in a first signal transducer active state, the second signal transducer when in a second signal transducer active state, or both, are capable of being localized at the association location; and an effector protein comprising a first cut site the first protease in the first protease active state is capable of cutting to change the effector protein to an effector active state, or an effector inactive state, which correlates with an aberrant signaling of the first signal transducer and/or the second signal transducer, and wherein the effector protein in the effector active state, or the effector inactive state, is capable of changing a state of the cell, thereby treating a disease or disorder characterized by the aberrant signaling of the first signal transducer and/or the second signal transducer.

21. A method of measuring a level of activation of one or more signal transducers comprising:

expressing a synthetic protein circuit in a cell of a subject in need thereof, the synthetic protein circuit comprising:

a first polypeptide comprising a first signal transducer binding domain and a first part of a first protease domain, wherein the first signal transducer binding domain is capable of binding a first signal transducer to form a first signal transducer-bound polypeptide;

a second polypeptide comprising a second signal transducer binding domain and a second part of the first protease domain, wherein the second signal transducer binding domain is capable of binding a second signal transducer to form a second signal transducer-bound polypeptide, wherein the first part of the first protease domain and the second part of the first protease domain have weak association affinity, and wherein the first part of the first protease domain and the second part of the first protease domain are capable of associating with each other to constitute a first protease capable of being in a first protease active state when the first signal transducer and the second signal transducer are in close proximity at an association location, and wherein the first signal transducer when in a first signal transducer active state, the second signal transducer when in a second signal transducer active state, or both, are capable of being localized at the association location; and an effector protein comprising a first cut site the first protease in the first protease active state is capable of cutting, wherein the effector protein changes from an effector inactive state to an effector active state when the first protease in the first protease active state cuts the first cut site of the effector protein, wherein a level of activation of the effector protein indicates a first level of activation of the first signal transducer and/or a second level of activation of the second signal transducer.

22. A nucleic acid encoding a synthetic protein circuit of claim 1, wherein the nucleic acid is an expression vector configured for expression of each of the first polypeptide, the second polypeptide, and the effector protein.

* * * * *